(12) United States Patent
Brant et al.

(10) Patent No.: US 7,279,536 B2
(45) Date of Patent: Oct. 9, 2007

(54) POLYMER PRODUCTION AT SUPERCRITICAL CONDITIONS

(75) Inventors: Patrick Brant, Seabrook, TX (US); Francis Charles Rix, League City, TX (US); Gabor Kiss, Hampton, NJ (US); Robert P. Reynolds, Clinton, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 11/510,871

(22) Filed: Aug. 25, 2006

(65) Prior Publication Data

US 2006/0293474 A1    Dec. 28, 2006

Related U.S. Application Data

(63) Continuation-in-part of application No. 11/177,004, filed on Jul. 8, 2005, now abandoned, and a continuation-in-part of application No. 10/667,585, filed on Sep. 22, 2003, and a continuation-in-part of application No. 10/667,586, filed on Sep. 22, 2003.

(60) Provisional application No. 60/586,465, filed on Jul. 8, 2004, provisional application No. 60/412,541, filed on Sep. 20, 2002, provisional application No. 60/431,077, filed on Dec. 5, 2002.

(51) Int. Cl.
   *C08F 4/6592* (2006.01)
   *C08F 2/02* (2006.01)

(52) U.S. Cl. ............ 526/160; 526/134; 526/170; 526/943; 502/117; 502/152

(58) Field of Classification Search ............ 526/134, 526/160, 170, 943; 502/117, 152
   See application file for complete search history.

(56) References Cited

U.S. PATENT DOCUMENTS

| | | | |
|---|---|---|---|
| 2,153,553 A | 4/1939 | Fawcett et al. | |
| 2,852,501 A | 9/1958 | Richard, Jr. et al. | |
| 3,294,772 A | 12/1966 | Cottle | |
| 3,725,378 A | 4/1973 | Chamberlin | |
| 4,135,044 A | 1/1979 | Beals | |
| 4,153,774 A | 5/1979 | Boettcher et al. | |
| 4,530,914 A | 7/1985 | Ewen et al. | |
| 4,740,550 A | 4/1988 | Foster | |
| 4,774,051 A | 9/1988 | Peehs et al. | |
| 4,794,004 A | 12/1988 | Pfleger et al. | |
| 4,962,262 A | 10/1990 | Winter et al. | |
| 5,026,798 A | 6/1991 | Canich | |
| 5,081,322 A | 1/1992 | Winter et al. | |
| 5,084,534 A | 1/1992 | Welborn, Jr. et al. | |
| 5,096,867 A | 3/1992 | Canich | |
| 5,272,236 A | 12/1993 | Lai et al. | |
| 5,324,799 A | 6/1994 | Yano et al. | |
| 5,324,800 A | 6/1994 | Welborn, Jr. et al. | |
| 5,326,835 A | 7/1994 | Ahvenainen et al. | |
| 5,382,630 A | 1/1995 | Stehling et al. | |
| 5,382,631 A | 1/1995 | Stehling et al. | |
| 5,391,654 A | 2/1995 | Ahvenainen et al. | |
| 5,408,017 A | 4/1995 | Turner et al. | |
| 5,416,153 A | 5/1995 | Winter et al. | |
| 5,455,365 A | 10/1995 | Winter et al. | |
| 5,514,761 A | 5/1996 | Etherton et al. | |
| 5,635,373 A | 6/1997 | Wozney et al. | |
| 5,652,308 A | 7/1997 | Merrill et al. | |
| 5,693,730 A | 12/1997 | Kuber et al. | |
| 5,723,560 A | 3/1998 | Canich | |
| 5,723,705 A | 3/1998 | Herrmann et al. | |
| 5,756,608 A | 5/1998 | Langhauser et al. | |
| 5,840,644 A | 11/1998 | Kuber et al. | |
| 5,866,663 A | 2/1999 | Brookhart et al. | |
| 5,882,750 A | 3/1999 | Mink et al. | |
| 5,936,053 A | 8/1999 | Fukuoka et al. | |
| 5,962,719 A | 10/1999 | Winter et al. | |
| 5,965,674 A | 10/1999 | Moen et al. | |
| 5,969,062 A | 10/1999 | Moll et al. | |
| 5,998,547 A | 12/1999 | Hohner | |

(Continued)

FOREIGN PATENT DOCUMENTS

CA    2 118 711    3/1993

(Continued)

OTHER PUBLICATIONS

Abstract, P. Lehmus et al., "Metallocene-PP produced under supercritical polymerization conditions", and list of posters, 1st BlueSky Conference on Catalytic Olefin Polymerization, Jun. 17-20, 2002, Sorrento, Italy.

(Continued)

*Primary Examiner*—Roberto Rabago
(74) *Attorney, Agent, or Firm*—Michael Kerns

(57) ABSTRACT

Process to polymerize olefins comprising contacting, in a polymerization system, olefins having three or more carbon atoms with a catalyst compound, activator, optionally comonomer, and optionally diluent or solvent, at a temperature above the cloud point temperature of the polymerization system and a pressure no lower than 10 MPa below the cloud point pressure of the polymerization system, where the polymerization system comprises any comonomer present, any diluent or solvent present, the polymer product, where the olefins having three or more carbon atoms are present at 40 weigh % or more.

69 Claims, 3 Drawing Sheets

U.S. PATENT DOCUMENTS

| | | |
|---|---|---|
| 6,034,022 A | 3/2000 | McAdon et al. |
| 6,051,522 A | 4/2000 | Rohrmann et al. |
| 6,057,408 A | 5/2000 | Winter et al. |
| 6,084,041 A | 7/2000 | Andtsjo et al. |
| 6,084,115 A | 7/2000 | Chen et al. |
| 6,143,682 A | 11/2000 | Fisher |
| 6,143,686 A | 11/2000 | Vizzini et al. |
| 6,160,072 A | 12/2000 | Ewen |
| 6,218,488 B1 | 4/2001 | Schiffino et al. |
| 6,225,432 B1 | 5/2001 | Weng et al. |
| 6,228,795 B1 | 5/2001 | Vizzini |
| 6,255,410 B1 | 7/2001 | Shigekauzu et al. |
| 6,268,444 B1 | 7/2001 | Klosin et al. |
| 6,300,451 B1 | 10/2001 | Mehta et al. |
| 6,355,741 B1 | 3/2002 | Marechal |
| 6,469,188 B1 | 10/2002 | Miller et al. |
| 6,479,424 B1 | 11/2002 | Ernst et al. |
| 6,492,473 B1 | 12/2002 | Canich et al. |
| 6,525,157 B2 | 2/2003 | Cozewith et al. |
| 6,562,914 B1 | 5/2003 | Andtsjo et al. |
| 6,576,306 B2 | 6/2003 | Mehta et al. |
| 6,583,277 B2 | 6/2003 | Luo et al. |
| 6,689,847 B2 | 2/2004 | Mawson et al. |
| 2002/0004575 A1 | 1/2002 | Cozewith et al. |
| 2002/0013440 A1 | 1/2002 | Agarwal et al. |
| 2004/0024146 A1 | 2/2004 | Friedersdorf |
| 2004/0127654 A1 | 7/2004 | Brant et al. |
| 2004/0132935 A1 | 7/2004 | Ariunan et al. |
| 2004/0158010 A1 | 8/2004 | Lehmus et al. |

FOREIGN PATENT DOCUMENTS

| | | |
|---|---|---|
| CA | 2 103 694 | 3/1994 |
| DE | 41 30 299 | 3/1993 |
| DE | 44 26 569 | 2/1995 |
| DE | 19823168 | 11/1999 |
| EP | 0 129 368 | 12/1984 |
| EP | 0 480 190 | 4/1992 |
| EP | 0 517 183 | 12/1992 |
| EP | 0 552 945 | 7/1993 |
| EP | 0 603 232 | 6/1994 |
| EP | 0 645 401 | 3/1995 |
| EP | 0 667 359 | 8/1995 |
| EP | 0 714 923 | 6/1996 |
| EP | 0 718 324 | 6/1996 |
| EP | 0 742 227 | 11/1996 |
| EP | 0 806 436 | 11/1997 |
| EP | 0 846 696 | 6/1998 |
| EP | 0 887 380 | 12/1998 |
| EP | 0 943 017 | 9/1999 |
| EP | 0 987 279 | 3/2000 |
| EP | 1 008 607 | 6/2000 |
| EP | 1 138 687 | 10/2001 |
| EP | 1 195 391 | 4/2002 |
| JP | 06-025357 | 10/1991 |
| JP | 96-208535 | 8/1996 |
| JP | 02-16916 | 8/1997 |
| JP | 342 1202 | 4/1998 |
| JP | 1998-110003 | 4/1998 |
| WO | WO88/02376 | 4/1988 |
| WO | WO88/04672 | 6/1988 |
| WO | WO92/114766 | 9/1992 |
| WO | WO93/05082 | 3/1993 |
| WO | WO93/11171 | 6/1993 |
| WO | WO94/14856 | 7/1994 |
| WO | WO96/00246 | 1/1996 |
| WO | WO96/12744 | 5/1996 |
| WO | WO96/18662 | 6/1996 |
| WO | WO96/34023 | 10/1996 |
| WO | WO97/03124 | 1/1997 |
| WO | WO97/11098 | 3/1997 |
| WO | WO97/13790 | 4/1997 |
| WO | WO97/45434 | 12/1997 |
| WO | WO97/48737 | 12/1997 |
| WO | WO98/13393 | 4/1998 |
| WO | WO98/33823 | 8/1998 |
| WO | WO98/49229 | 11/1998 |
| WO | WO99/02540 | 1/1999 |
| WO | WO99/29749 | 6/1999 |
| WO | WO99/32226 | 7/1999 |
| WO | WO99/40129 | 8/1999 |
| WO | WO99/43717 | 9/1999 |
| WO | WO 00/06621 | 2/2000 |
| WO | WO 00/12565 | 3/2000 |
| WO | WO 00/12572 | 3/2000 |
| WO | WO 00/23822 | 4/2000 |
| WO | WO 00/24613 | 5/2000 |
| WO | WO 00/25916 | 5/2000 |
| WO | WO 00/26266 | 5/2000 |
| WO | WO 00/37514 | 6/2000 |
| WO | WO 00/40625 | 7/2000 |
| WO | WO 00/50475 | 8/2000 |
| WO | WO 00/64952 | 11/2000 |
| WO | WO 01/44318 | 6/2001 |
| WO | WO 01/46273 | 6/2001 |
| WO | WO 02/01745 | 1/2002 |
| WO | WO 02/44260 | 6/2002 |
| WO | WO 02/50145 | 6/2002 |
| WO | WO 02/070572 | 9/2002 |
| WO | WO 02/083753 | 10/2002 |
| WO | WO 02/090399 | 11/2002 |
| WO | WO 2004/026921 | 4/2004 |
| WO | WO 2004/050724 | 6/2004 |

OTHER PUBLICATIONS

Abstract, Borealis publications, Lofgren et al., "*Metallocene-PP produced under supercritical conditions*", 1st BlueSky Conference on Catalytic Olefin Polymerization, Jun. 17-20, 2002, Sorrento, Italy (2002).

Abstract, Zowade et al., PL 159518, "*Manufacturing Low-molecular-weight Isotactic Polypropylene*", Sep. 1, 1989.

Alt, H.G. et al., "*Effect of the Nature of Metallocene Complexes of Group IV Metals on Their Performance in Catalytic Ethylene and Propylene Polymerization*", Chem. Rev. 100, 2000, pp. 1205-1221.

Akimoto, A., et al., "*New Developments in the Production of Metallocene LLDPE by High Pressure Polymerization*", Tosoh Corp., Metallocene-Based Polyolefins 2000 (conference proceedings), pp. 287-308 (John Wiley & Sons Ltd.).

Barnhart, R.W. et al., "*Synthesis of Branched Polyolefins Using a Combination of Homogeneous Metallocene Mimics*", J. Am. Chem. Soc. 1998, vol. 120, pp. 1082-1083.

Bergemann, C., R. et al., "*Copolymerization of Ethylene and 1,5-hexadiene under High Pressure Catalyzed by a Metallocene*", J. Mol. Catal. A: Chemical 116, 1997, pp. 317-322 (Elsevier).

Britovsek, G.J.P. et al., "*The Search for New-Generation Olefin Polymerization Catalysts: Life Beyond Metallocenes*", Chemie Intl. Edn., 1999, vol. 38, pp. 428-447.

Bujadoux, G.K., "*Use of Bridged and Non-Bridged Metallocene Catalysis in High Pressure/High Temperature Ethylene/α-Olefin Copolymerization*", Metallocenes 95 Intl. Congr, Metallocene Polym. 1995, pp. 375-402, Schotland Bus. Rsrch. Publ.

Chen, E. Y-X. et al., "*Cocatalysts for Metal-Catalyzed Olefin Polymerization: Activators, Activation Processes, and Structure-Activity Relationships*", Chem. Rev. 2000, vol. 100, pp. 1391-1434.

Coates, G.W., "*Precise Control of Polyolefin Stereochemistry Using Single Site Metal Catalysts*", Chem. Rev. 100, 2000, pp. 1223-1252.

Cottom, W.P., "*Waxes*", in Encyclo. Chem. Tech., vol. 25, pp. 614-626, Fourth edition, 1991.

Eckstein A. et al., "*Determination of Plateau Moduli and Entanglement Molecular Weights of Isotactic Syndiotactic, and Atactic Polypropylenes Synthesized with Metallocene Catalysts*", Macromolecules 31, 1998, pp. 1335-1340.

Ewen, J.A. et al., "*Syndiospecific Propylene Polymerizations with Group 4 Metallocenes*", J. Am. Chem. Soc., 1988, vol. 110, pp. 6255-6256.

Gotz, C. et al., "*MAO-Free Metallocene Based Catalysis in High Pressure Polymerization of Ethylene and 1-Hexene*", Chem. Eng. Technol., 21, 1998, pp. 954-957 (Wiley-VCH Verlag GmbH).

Hauptman, E. et al., "*Stereoblock Polypropylene: Ligand Effects on the stereospecificity of 2-Arylindene Zirconocene Catalysts*", J. Am. Chem. Soc. 1995, vol. 117, pp. 11586-11587.

Ittel, S.D. et al., "*Late Metal Catalysts for Ethylene Homo- and Copolymerization*", Chem. Rev. 2000, vol. 100, pp. 1169-1203.

Janiak, C.; "*Metallocene Catalysts for Olefin Polymerization*", Metallocenes: Synthesis, Reactivity, and Applications, vol. 2, Wiley-VCH, 1998, pp. 547-614, A. Togni and R.L. Halterman, editors.

Resconi, L. et al., "*Selectivity in Propene Polymerization with Metallocene Catalysts*", Chem. Rev. 2000, vol. 100, pp. 1253-1345.

Schaverien, C.J. et al., "*Ethylene Bis(2-indenyl) Zirconocenes: A New Class of Diastereomeric Metallocenes for the (Co)Polymerization of α-Olefins*", Organometallics 2001, vol. 20, No. 16, pp. 3436-3452, (ACI.

Scollard, J.D. et al., "*Polymerization of α-Olefins by Chelating Diamide Complexes of Titanium*", Macromolecules, 1996, vol. 29, pp. 5241-5243.

Smith, B.D. et al., "*Thermodynamic Data for Pure Compounds Part A, Hydrocarbons and Ketones Physical Sciences Data*", vol. 25, Elsevier, New York, 1986, pp. 308-309.

Stephenson R.M. et al., "*Handbook of the Thermodynamics of Organic Compounds*", Elsevier Science Publ. NY, p. 75, 1987.

Stratton, A.W., "*Waxes*", in Encyclo. Polymer Science and Eng., vol. 17, pp. 784-795, Second Edition, 1985.

Suzuki, N. et al., "*Olefin Polymerization Using Highly Congested Ansa-Metallocences Under High Pressure: Formation Of Superhigh Molecular Weight Polyolefins*", Macromolecules, 2000, vol. 33, No. 3, pp. 754-759.

Yano, A., et al., "*Homo- and Copolymerization of Ethylene at High Temperature with Cationic Zirconocene Catalysts*", Macromol. Chem. Phys. 200, No. 4, pp. 917-923 (Wiley-VCH Verlag GmbH, 1999).

Yano, A., et al., "*Homo- and Copolymerization of Ethylene by Cationic Hafnocene Catalysts based on Tetrakis(pentafluorophenyl)*", Macromol. Chem. Phys. 200, No. 4, 1999, pp. 924-932, (Wiley-VDH Verlag.

Yano, A., et al., "*Novel Zirconocene Catalysts for the Production of High molecular Weight LLDPE in High Temperature Polymerization*", Macromol. Chem. Phys. 200, No. 4, 1999, pp. 933-941, (Wiley-VCH Verlag.

Walther, D. et al.; "Metallocent Catalyzed Polymerisation in Supercritical Propylene", High Pressure In Venice, Sep. 22-25, 2002, Venice-Italy.

Chart 20. Chain Microstructure Defects Generated by Isolated Secondary (2,1) Insertion: *erythro* (*meso*), *threo* (*racemic*) Secondary Units and 3,1 Unit[a]

2,1-erythro (e)

2,1-threo (t)

3,1-insertion (i)

FIG. 3

Table 2. $^{13}$C NMR Chemical Shifts and Carbon Numbering of Common Polypropene Chain End Groups

| C | n-propyl | isobutyl | 2,3-dimethyl-butyl | allyl | vinylidene | isobutenyl | cis-2-butenyl |
|---|----------|----------|--------------------|-------|------------|------------|---------------|
| 1 | 14.47 | 22.61 | 17.76 | 115.57 | 111.38 | 18.01 | 12.91 |
| 2 | 20.12 | 25.79 | 31.93 | 137.67 | 144.87 | 129.23 | 124.48 |
| 3 | 39.68 | 23.83 | 20.56 | 41.38 | 22.6 | 25.7 | 129.66 |
| 4 | 30.50 | 47.50 | 36.47 | 30.80 | | 132.30 | 34.37 |
| 5 | 20.81 | ? | 16.30 | 20.64 | | 30.61 | 31.37 |
| 6 | 45.98 | 21.13 | 43.05 | 45.33 | | | ? |
| 7 | | | | ? | | | 45.54 |
| 8 | | | | 21.43 | | | |

POLYMER PRODUCTION AT SUPERCRITICAL CONDITIONS

CROSS REFERENCE TO RELATED APPLICATIONS

This application is a continuation-in-part of U.S. Ser. No. 11/177,004, filed on Jul. 8, 2005 now abandoned which claims the benefit of U.S. Ser. No. 60/586,465, filed Jul. 8, 2004. U.S. Ser. No. 11/177,004 is a continuation in part of U.S. Ser. No. 10/667,585, filed Sep. 22, 2003, which claims the benefit of U.S. Ser. No. 60/412,541, filed Sep. 20, 2002, and claims the benefit of U.S. Ser. No. 60/431,077, filed Dec. 5, 2002. U.S. Ser. No. 11/177,004, is also a continuation-in-part of U.S. Ser. No. 10/667,586, filed Sep. 22, 2003, which claims the benefit of U.S. Ser. No. 60/412,541, filed Sep. 20, 2002, and claims the benefit of U.S. Ser. No. 60/431,077, filed Dec. 5, 2002.

FIELD OF THE INVENTION

This invention relates to polymerization of olefin monomers having three or more carbon atoms under supercritical conditions using certain metallocene catalyst compounds.

BACKGROUND OF THE INVENTION

Since the mid-1980s metallocene catalysts have been used in high-pressure reactors—mainly for producing ethylene-backbone polymers including ethylene copolymers with monomers of one or more of propylene, butene, and hexene, along with other specialty monomers such as 4-methyl-1,5-hexadiene. For example, U.S. Pat. No. 5,756,608 to Langhausen et al., reports a process for polymerizing $C_2$ to $C_{10}$ 1-alkenes using bridged metallocene catalysts. Polypropylene production in high pressure conditions has, however, been seen as impractical and unworkable at temperatures much above the propylene critical point. A process to produce commercially useful polypropylene in a high pressure system would provide advantages, such as increased reactivity, or increased catalyst productivity, or higher throughput, or shorter residence times, etc. Likewise new polypropylene polymers are also in constant need for the preparation of new and improved products. Thus there is a need in the art to develop new processes capable of greater efficiency and manufacture of new polypropylene polymers.

In addition there is also a need for polymerization processes that are flexible enough to be used with other monomers. For example, a high pressure process to make polybutene or polyhexene is also desirable.

U.S. Pat. No. 6,084,041, granted to Andtsjö et al., discloses supercritical propylene polymerization under relatively mild conditions (90-100° C. and less than 6.89 MPa pressure) using supported Ziegler-Natta and metallocene catalysts. This patent does not relate to propylene copolymerization at temperatures or pressures much higher than described above. It also does not specifically disclose bulk propylene polymerization using soluble, unsupported metallocene catalysts.

U.S. Pat. No. 5,969,062 granted to Mole et al., describes a process for preparing ethylene copolymers with α-olefins in which polymerization is carried out at a pressure between 100-350 MPa and at a temperature from 200-280° C. The catalyst is based on a tetramethylcyclopentadienyl titanium complex.

U.S. Pat. No. 5,408,017 describes an olefin polymerization catalyst for use at polymerization temperatures of 140° C.-160° C., or greater. Mainly, temperatures exceeding the melting point temperature and approaching the polymer decomposition temperature are said to yield high productivity.

WO 93/11171 discloses a polyolefin production process that comprises continuously feeding olefin monomer and a metallocene catalyst system into a reactor. The monomer is continuously polymerized to provide a monomer-polymer mixture. Reaction conditions keep this mixture at a pressure below the system's cloud-point pressure. These conditions create a polymer-rich and a monomer-rich phase and maintain the mixture's temperature above the polymer's melting point.

U.S. Pat. No. 6,355,741 discloses a process for producing polyolefins having a bimodal molecular weight distribution. The process comprises producing a first polyolefin fraction in a first loop reactor. The process couples this first loop reactor to a second loop reactor that prepares a second polyolefin fraction. At least one of the loops uses supercritical conditions.

WO 92/14766 describes a process comprising the steps of (a) continuously feeding olefinic monomer and a catalyst system, with a metallocene component and a cocatalyst component, to the reactor; (b) continuously polymerizing that monomer in a polymerization zone reactor under elevated pressure; (c) continuously removing the polymer/monomer mixture from the reactor; (d) continuously separating monomer from molten polymer; (e) reducing pressure to form a monomer-rich and a polymer-rich phase; and (f) separating monomer from the reactor.

U.S. Pat. No. 5,326,835 describes bimodal polyethylene production. This invention's first reactor stage is a loop reactor in which polymerization occurs in an inert, low-boiling hydrocarbon. After the loop reactor, the reaction medium transits into a gas-phase reactor where gas-phase ethylene polymerization occurs. The polymer produced appears to have a bimodal molecular weight distribution.

CA 2,118,711 (equivalent to DE 4,130,299) describes propylene polymerization at 149° C. and 1510 bar using $(CH_3)_2C$(fluorenyl)(cyclopentadienyl) zirconium dichloride complex, methylalumoxane and trimethylaluminum. Catalyst activity is reported to be 8380 gPP/g Ic' h. The $M_w$ is reported to be 2,000. CA 2,118,711 also describes propylene polymerization with ethylene at 190° C. and 1508 bar using $(CH_3)_2C$(fluorenyl)(cyclopentadienyl)zirconium dichloride complex, methylalumoxane and trimethylaluminum. Catalyst activity is reported to be 24358 g Polymer/gIc' hr. The $M_w$ is reported to be 10,000.

WO 2004/026921 discloses a process to polymerize olefins comprising contacting, in a polymerization system, olefins having three or more carbon atoms with a catalyst compound (such as a metallocene), activator, optionally comonomer, and optionally diluent or solvent, at a temperature above the cloud point temperature of the polymerization system and a pressure no lower than 10 MPa below the cloud point pressure of the polymerization system, where the polymerization system comprises any comonomer present, any diluent or solvent present, the polymer product, where the olefins having three or more carbon atoms are present at 40 weight % or more.

Furthermore, various processes and catalysts exist for the homopolymerization or copolymerization of unsaturated monomers, particularly the polymerization of olefins. For many applications, it is desirable for a polyolefin to have a high weight average molecular weight while having a relatively narrow molecular weight distribution. Chiral bis-indenyl metallocene catalysts have been used to prepare highly crystalline isotatic polypropylene and copolymers of propylene and other monomers (Resconi, L. Chem. Rev. 2000, 100, 1253). Non-chiral metallocene catalysts have also been prepared which yield atactic polypropylene and copolymers (Resconi, L. in Metallocene Based Polyolefins, Eds. J. Schiers, W. Kaminsky; Wiley; NY, 2000; 467). While there are chiral catalysts which operate between these extremes, yielding polypropylene with crystallinity less than highly crystalline and more than amorphous, generally these chiral catalysts give low molecular weight polymer. This is also true for copolymers prepared from propylene and other monomers, using such systems.

U.S. Pat. No. 6,051,522 describes bridged chiral metallocenes as catalysts useful for olefin polymerization. WO 2002/01745, U.S. 2002/0004575A1, WO 2002/083753A1, and U.S. Pat. No. 6,525,157 disclose processes for the preparation of a propylene/ethylene copolymer containing tacticity within the propylene sequences using the chiral metallocene rac-Me$_2$Si(1-indenyl)$_2$HfMe$_2$ and an ionizing activator. U.S. Pat. No. 6,057,408 discloses a process for the preparation of high molecular weight propylene/ethylene copolymers with high crystallinity in the propylene sequences using chiral bis-indenyl metallocenes. The catalyst that yielded the highest molecular weight copolymer was rac-Me$_2$Si(2-Me-4-(1-napthyl)-1-indenyl)$_2$ZrCl$_2$.

S. Collins and coworkers reported (Organometallics 1992, 11, 2115) a study of the effect of substituents in the 5,6-positions on a series of chiral ethylene bridged metallocenes, rac-(CH$_2$CH$_2$)(5,6-X$_2$-1-indenyl)$_2$ZrCl$_2$, on solution ethylene and propylene polymerizations. In comparing X=H and X=Me, similar molecular weights were found for the preparation of polyethylene (X=H, Mn=145 kg/mol; X=Me, Mn=127 kg/mol) and polypropylene (X=H, Mn=15.7 kg/mol; X=Me, Mn=16 kg/mol). Likewise, in U.S. Pat. No. 5,455,365, chiral bis-indenyl metallocenes containing methyl groups in the 5 and 6 positions and metallocenes containing a phenyl group in the 5 or 6 position are disclosed. Polymerizations at 70° C. in liquid propylene gave moderately crystalline polypropylene, as evidenced by polymer melting points between 132 and 147° C. The molecular weights (Mw) of these materials are between 100 and 200 kg/mol. Copolymerization of propylene with ethylene, using rac-Me$_2$Si(2,5,6-Me$_3$-1-indenyl)ZrCl$_2$/MAO, yielded a 2.8 wt % ethylene, 97.2 wt % propylene copolymer with a significantly lower molecular weight as evidenced by a drop in intrinsic viscosity from 155 mL/g (Mw=143 kg/mol) to 98 mL/g (Mw not recorded). This copolymerization also gave a decrease in melting point from 132 to 123° C.

In U.S. Pat. No. 6,084,115, a chiral bis-indenyl metallocene containing an annulated tetramethylated cyclohexyl ring attached at the 5 and 6 positions is disclosed. This metallocene, rac-Me$_2$Si(5,6,7,8-tetrahydro-2,5,5,8,8-pentamethyl-benz[f]indenyl)$_2$Zr(1,4-diphenylbutadiene), is reported to be in the +2 oxidation state. Propylene polymerization behavior was reported in alkane solution (24 wt % propylene) under a partial pressure of hydrogen at 70° C. Molecular weights obtained were ca. 60 kg/mol and polymer melting points were 144.8-147° C. These molecular weights were lower than the analogous complex with H in the 5 and 6 positions, rac-Me$_2$Si(2-Me-1-indenyl)Zr(1,4-diphenylbutadiene), Mw=79 kg/mol. Similar results were observed in ethylene/octene polymerizations with these two catalysts. No H$_2$-free solution polymerizations were reported. Supported catalysts were also examined in U.S. Pat. No. 6,084, 115, however broad molecular weight distributions (>3.5) make comparisons between catalysts difficult. These results indicate that a molecular weight advantage is not expected for catalysts with large groups in the 5 and 6 positions. Thus, no meaningful increase in polymer molecular weight can be ascribed to these previous substitutions.

WO 2004/050724 discloses polymerization of butene with methylalumoxane and dimethylsilyl bis[2-methyl-5,6 (tetramethyl-cyclotrimethylen)indenyl]zirconium dichloride and also described certain indenyl type compounds with annulated six membered rings; however, WO 2004/050724 does not obtain higher molecular weights at higher temperatures.

Thus there is a need in the art to provide catalyst systems that can provide polymers having high molecular weight as well as good crystallinity preferably prepared at higher temperatures and productivities than otherwise possible.

U.S. Pat. No. 6,479,424 discloses the preparation of unbridged species bis(2-(3,5-di-t-butylphenyl)-5,5,8,8-tetramethyl-5,6,7,8-tetrahydrobenz(f)indenyl) hafnium dichloride, bis(2-(3,5-di-t-butylphenyl)-5,5,8,8-tetramethyl-5,6,7, 8-tetrahydrobenz(f)indenyl) zirconium dichloride, bis(2-(4-t-butylphenyl)-5,5,8,8-tetramethyl-5,6,7,8-tetrahydrobenz (f)indenyl) hafnium dichloride, and bis(2-(4-t-butylphenyl)-5,5,8,8-tetramethyl-5,6,7,8-tetrahydrobenz(f)indenyl) zirconium dichloride which are used to produce propylene polymers.

Other references of interest include: 1) U.S. Pat. No. 6,034,022, (particularly example 17); 2) U.S. Pat. No. 6,268, 444, (particularly example 2); 3) U.S. Pat. No. 6,469,188; and 4) EP 1 138 687, (particularly examples 8 and 9), and *Olefin Polymerization Using Highly Congested ansa-Metallocenes under High Pressure: Formation of Superhigh Molecular Weight Polyolefins*, Suzuki, et al., Macromolecules, 2000, 33, 754-759, EP 1 123 226, WO 00 12572, WO 00 37514, EP 1 195 391, U.S. Pat. No. 6,355,741, and *Ethylene Bis(Indenyl) Zirconocenes* . . . , Schaverien, C. J. et al., Organometallics, ACS, Columbus Ohio, vol 20, no. 16, August 2001, pg 3436-3452, WO 96/34023, WO 97/11098, U.S. Pat. Nos. 5,084,534, 2,852,501, WO 93/05082, EP 129 368 B1, WO 97/45434, JP 96-208535 199660807, U.S. Pat. No. 5,096,867, WO 96/12744, U.S. Pat. Nos. 5,408,017, 5,084,534, 6,225,432, WO 02/090399, EP 1 195 391, WO 02/50145, U.S. 2002 013440, WO 01/46273, EP 1 008 607, JP-1998-110003A, U.S. Pat. No. 6,562,914, and JP-1998-341202B2.

Another item of interest is an abstract obtained from the Borealis website that states:

> Barbo Loefgren, E. Kokko, L. Huhtanen, M Lahelin, Petri Lehmus, Udo Stehling. "Metallocene-PP produced under supercritical conditions." 1st Blue Sky Conference on Catalytic Olefin Polymerization, 17.- 20.6.2002, Sorrento, Italy, 2002. "mPP produced in bulk conditions (100% propylene), especially at elevated temperature and under supercritical conditions, shows rheological behaviour indicative for small amounts of LCB in the polymer. This is a feature that can be utilized to produce mPP with enhanced melt strength under industrially meaningful conditions."

SUMMARY OF THE INVENTION

This invention relates to a process to polymerize olefins comprising contacting, in a polymerization system, olefin monomers having three or more carbon atoms with a metallocene catalyst compound, an activator, optionally comonomer, and optionally diluent or solvent, at a temperature above the cloud point temperature of the polymerization system and a pressure no lower than 10 MPa below the cloud point pressure of the polymerization system and less than 1000 MPa, where the polymerization system comprises the monomers, any comonomer present, any diluent or solvent present, the polymer product, and where the olefin monomers having three or more carbon atoms are present at 40 weight % or more, where the metallocene catalyst compound is represented by the formula 1:

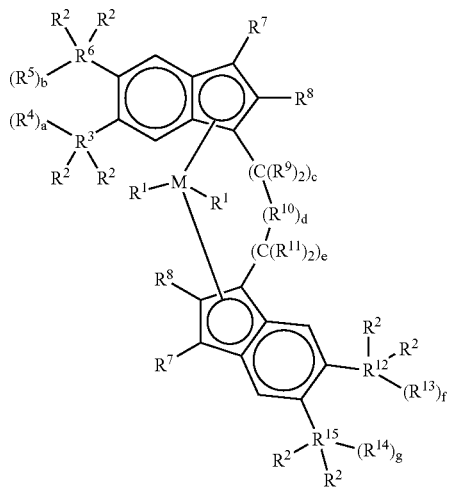

where

M is a transition metal selected from group 4 of the periodic table;

each $R^1$ is independently selected from the group consisting of hydrogen, hydrocarbyl, substituted hydrocarbyl and functional group, and any two $R^1$ may be linked;

each $R^2$ is independently selected from the group consisting of hydrogen, hydrocarbyl, substituted hydrocarbyl or functional group, and two or more $R^2$ groups may be linked together to form an aliphatic or aromatic ring;

$R^3$ is carbon or silicon;

$R^4$ is hydrogen, hydrocarbyl, substituted hydrocarbyl or a functional group;

a is 0, 1, or 2;

$R^5$ is hydrogen, hydrocarbyl, substituted hydrocarbyl or a functional group, $R^4$ and $R^5$ may be bound together to form a ring, and $R^5$ and $R^3$ may be bound together to form a ring;

b is 0, 1, or 2;

$R^6$ is carbon or silicon; and $R^4$ and $R^6$ may be bound together to form a ring;

each $R^7$ is independently selected from the group consisting of hydrogen, hydrocarbyl, substituted hydrocarbyl and a functional group;

each $R^8$ is independently selected from the group consisting of hydrogen, hydrocarbyl, substituted hydrocarbyl and a functional group, and $R^7$ and $R^8$ may be linked together to form an aliphatic or aromatic ring;

each $R^9$ is independently selected from the group consisting of hydrogen, hydrocarbyl, substituted hydrocarbyl and a functional group, and two $R^9$ groups may be linked together to form a ring, $R^9$ and $R^8$ may be linked together to form a ring, $R^9$ and $R^{16}$ may be linked together to form a ring, $R^9$ and $R^{11}$ may be linked together to form a ring;

c is 0,1 or 2;

$R^{10}$ is $-M^2(R^{16})_h$-where $M^2$ is B, Al, N, P, Si or Ge, h is an integer from 1 to 2, such that the valence of $M^2$ is filled, and $R^{16}$ is hydrogen, hydrocarbyl, substituted hydrocarbyl or a functional group, and two $R^{16}$ groups may be linked together to form a ring;

d is 0, 1, or 2;

each $R^{11}$ is independently selected from the group consisting of hydrogen, hydrocarbyl, substituted hydrocarbyl and a functional group, and two $R^{11}$ groups may be linked together to form a ring, and $R^{11}$ and $R^8$ may be linked together to form a ring, and $R^{11}$ and $R^{16}$ may be linked together to form a ring;

e is 0, 1, or 2;

where the sum of c, d, and e is 1, 2 or 3;

$R^{12}$ is carbon or silicon;

$R^{13}$ is hydrogen, hydrocarbyl, substituted hydrocarbyl or a functional group, and $R^{13}$ and $R^{14}$ may be bound together to form a ring, and $R^{13}$ and $R^{15}$ may be bound together to form a ring, when g is 0;

f is 0, 1, or 2;

$R^{14}$ is hydrogen, hydrocarbyl, substituted hydrocarbyl or a functional group, and $R^{14}$ and $R^{12}$ may be bound together to form a ring, when f is 0;

g is 0, 1, or 2; and $R^{15}$ is carbon or silicon;

provided that if the two $R^1$ groups are linked, then they do not form a butadiene group when M is Zr.

BRIEF DESCRIPTION OF THE FIGURES

FIG. 3 shows a table of the chemical shift offsets for resonances associated with a variety of chain end groups.

DEFINITIONS OF THE INVENTION

Figure 1:
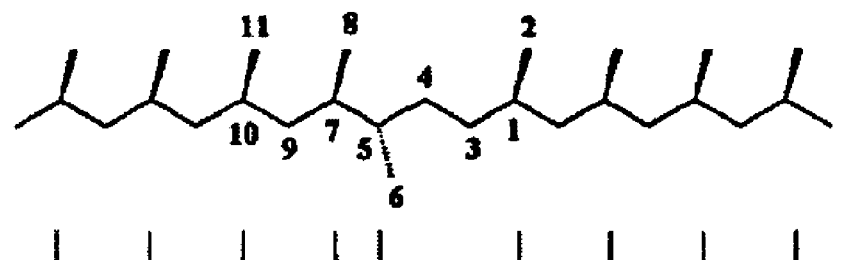
FIG. 1 shows the numbering scheme and structures for the different chain defects.
Figure 1:
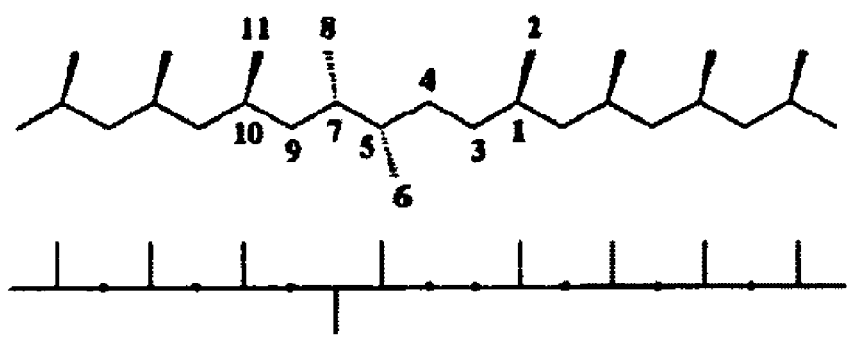
Figure 1:
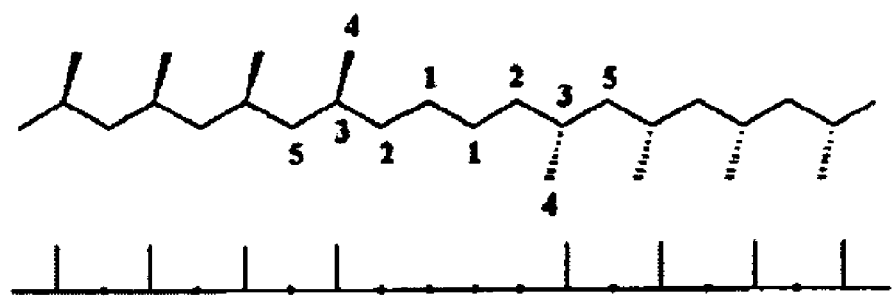
Figure 2:
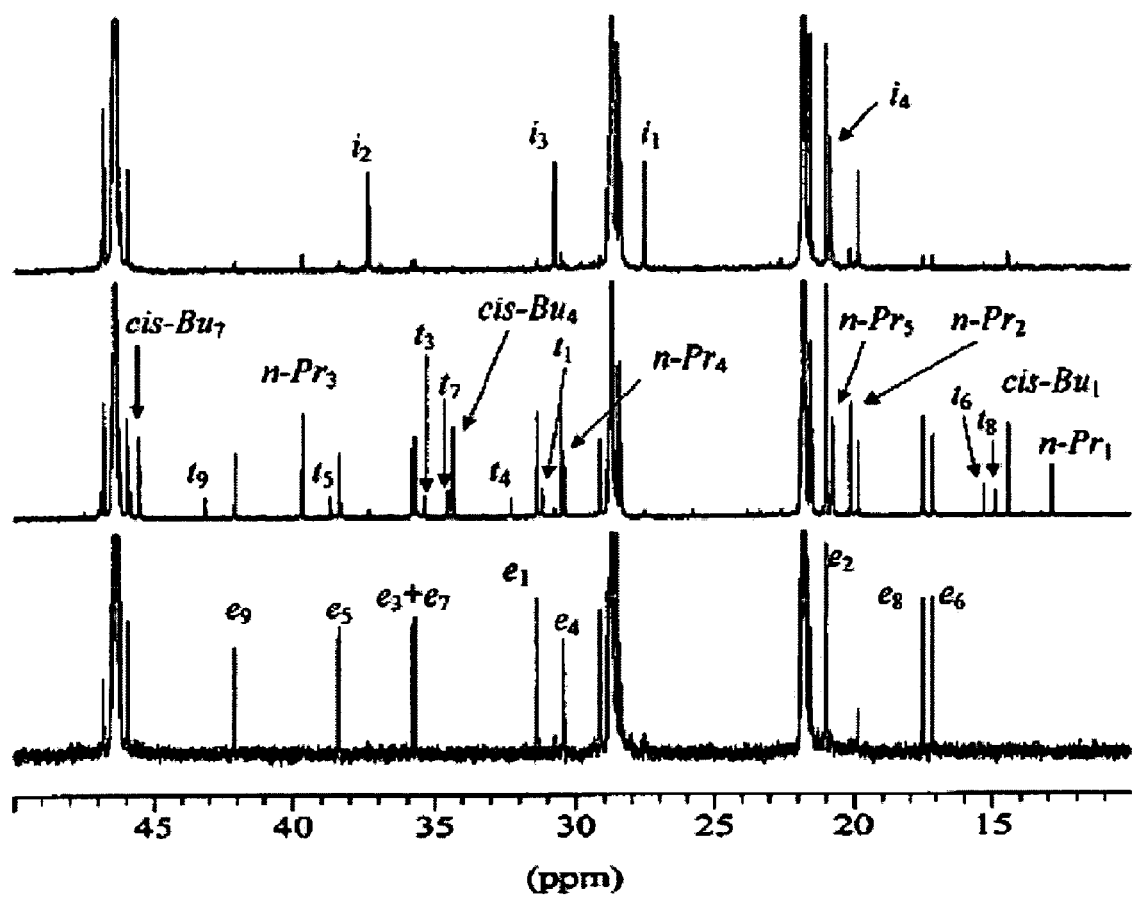
FIG. 2 shows the appearance of the various defects in a $^{13}C$ NMR spectrum.

For purposes of this invention and the claims thereto:
1. A catalyst system is defined to be the combination of a catalyst compound and an activator.
2. The cloud point is the pressure below which, at a given temperature, the polymerization system becomes turbid as described in J. Vladimir Oliveira, C. Dariva and J. C. Pinto, Ind. Eng, Chem. Res. 29, 2000, 4627. For purposes of this invention and the claims thereto, the cloud point is measured by shining a helium laser through the selected polymerization system in a cloud point cell onto a photocell and recording the pressure at the onset of light scattering for a given temperature.
3. A higher α-olefin is defined to be an olefin having 4 or more carbon atoms.
4. Use of the term "polymerization" encompasses any polymerization reaction such as homopolymerization and copolymerization.
5. A copolymerization encompasses any polymerization reaction of two or more monomers.
6. The new numbering scheme for the Periodic Table Groups is used as published in CHEMICAL AND ENGINEERING NEWS, 63(5), 27 (1985).
7. When a polymer is referred to as comprising an olefin, the olefin present in the polymer is the polymerized form of the olefin.
8. An oligomer is defined to be compositions having 2-75 mer units.
9. A polymer is defined to be compositions having 76 or more mer units.

10. The following abbreviations are used: Me is methyl, Ph is phenyl, Et is ethyl, Pr is propyl, iPr is isopropyl, n-Pr is normal propyl, Bu is butyl, iBu is isobutyl, tBu is tertiary butyl, p-tBu is para-tertiary butyl, TMS is trimethylsilyl, TIBA is trisobutylaluminum, MAO is methylalumoxane, pMe is para-methyl, flu is fluorenyl, cp is cyclopentadienyl.

As used herein, the term "slurry polymerization" means a polymerization process that involves at least two phases, e.g., in which particulate, solid polymer (e.g., granular) is formed in a liquid, supercritical, or vapor polymerization medium, or in a liquid/vapor polymerization medium.

As used herein, the term "bulk polymerization" means a polymerization process in which the polymerization medium is predominantly monomer and contains less than 60 wt % of solvent or diluent.

As used herein the term continuous means a system that operates (or is intended to operate) without interruption or cessation. For example, a continuous process to produce a polymer would be one where the reactants are continually introduced into one or more reactors and polymer product is continually withdrawn.

DETAILED DESCRIPTION OF THE INVENTION

This invention relates to a process to polymerize olefins comprising contacting, in a polymerization system, olefin monomers having three or more carbon atoms (preferably propylene) with a metallocene catalyst compound, an activator, optionally comonomer (preferably ethylene, butene, hexene or octene), and optionally diluent or solvent, at a temperature above the cloud point temperature of the polymerization system (preferably 100° C. or more, preferably 105° C. or more, preferably 110° C. or more and a pressure no lower than 10 MPa below the cloud point pressure of the polymerization system and less than 1000 MPa, (preferably 27.5 MPa or more, preferably 40.0 MPa or more) where the polymerization system comprises the monomers, any comonomer present, any diluent or solvent present, the polymer product, and where the olefin monomers are present in the polymerization system at 40 weight % or more, wherein the metallocene catalyst compound is represented by the formula:

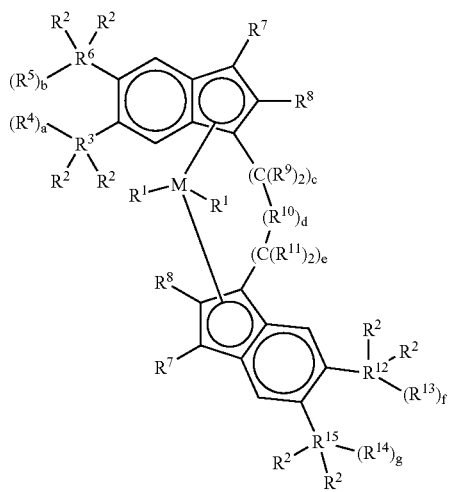

where

M is a transition metal selected from group 4 of the periodic table;

each $R^1$ is independently selected from the group consisting of hydrogen, hydrocarbyl, substituted hydrocarbyl and functional group, and any two $R^1$ groups may be linked, provided that if the two $R^1$ groups are linked, then they do not form a butadiene group when M is Zr;

each $R^2$ is independently selected from the group consisting of hydrogen, hydrocarbyl, substituted hydrocarbyl or a functional group, and two or more $R^2$ groups may be linked together to form an aliphatic or aromatic ring;

$R^3$ is carbon or silicon;

$R^4$ is hydrogen, hydrocarbyl, substituted hydrocarbyl or a functional group;

a is 0, 1, or 2;

$R^5$ is hydrogen, hydrocarbyl, substituted hydrocarbyl or a functional group, $R^4$ and $R^5$ may be bound together to form a ring, and $R^5$ and $R^3$ may be bound together to form a ring;

b is 0, 1, or 2;

$R^6$ is carbon or silicon; and $R^4$ and $R^6$ may be bound together to form a ring;

each $R^7$ is independently selected from the group consisting of hydrogen, hydrocarbyl, substituted hydrocarbyl and a functional group;

each $R^8$ is independently selected from the group consisting of hydrogen, hydrocarbyl, substituted hydrocarbyl and a functional group, and $R^7$ and $R^8$ may be linked together to form an aliphatic or aromatic ring;

each $R^9$ is independently selected from the group consisting of hydrogen, hydrocarbyl, substituted hydrocarbyl and a functional group, and two $R^9$ groups may be linked together to form a ring, $R^9$ and $R^8$ may be linked together to form a ring, $R^9$ and $R^{16}$ may be linked together to form a ring, R9 and $R^{11}$ may be linked together to form a ring;

c is 0, 1 or 2;

$R^{10}$ is -$M^2(R^{16})_h$-where $M^2$ is B, Al, N, P, Si or Ge, h is an integer from 1 to 2, such that the valence of $M^2$ is filled, and $R^{16}$ is hydrogen, hydrocarbyl, substituted hydrocarbyl or a functional group, and two $R^{16}$ groups may be linked together to form a ring;

d is 0, 1, or 2;

each $R^1$ is independently selected from the group consisting of hydrogen, hydrocarbyl, substituted hydrocarbyl and a functional group, and two $R^{11}$ groups may be linked together to form a ring. $R^{11}$ and $R^8$ may be linked together to form a ring. $R^{11}$ and $R^{16}$ may be linked together to form a ring;

e is 0, 1, or 2;

where the sum of c, d, and e is 1, 2 or 3;

$R^{12}$ is carbon or silicon;

$R^{13}$ is hydrogen, hydrocarbyl, substituted hydrocarbyl or a functional group, and $R^{13}$ and $R^{14}$ may be bound together to form a ring, and $R^{13}$ and $R^{15}$ may be bound together to form a ring, when g is 0;

f is 0, 1, or 2;

$R^{14}$ is hydrogen, hydrocarbyl, substituted hydrocarbyl or a functional group, and $R^{14}$ and $R^{12}$ may be bound together to form a ring, when f is 0;

g is 0, 1, or 2; and $R^{15}$ is carbon or silicon.

In an alternate embodiment,

M is a transition metal selected form group 4 of the periodic table, preferably Zr or Hf, most preferably Hf;

each $R^1$ is independently selected from the group consisting of hydrogen, hydrocarbyl, substituted hydrocarbyl and a functional group, preferably, $R^1$ is hydrogen, a hydrocarbon or a halide, preferably $R^1$ is a hydride, even more preferably $R^1$ is selected from the group consisting of methyl, ethyl, trimethylsilylmethyl, trimethylsilyl, phenyl, naphthyl, allyl, and benzyl; even more preferably, $R^1$ is methyl, and $R^1$ may be linked, and the $R^1$ groups may be the same or different;

each $R^2$ is independently selected from the group consisting of methyl, ethyl, propyl, butyl, pentyl, hexyl and the isomers thereof, provided that when $R^3$ and $R^6$ and or $R^{12}$ and $R^{15}$ form a 5 carbon ring, then each $R^2$ is independently selected from the group consisting of ethyl, propyl, butyl, pentyl, hexyl and the isomers thereof, preferably $R^2$ is methyl, ethyl or propyl, more preferably, $R^2$ is methyl, and the $R^2$ groups may be the same or different;

$R^3$ is carbon or silicon;

$R^4$ is hydrogen, hydrocarbyl, substituted hydrocarbyl or a functional group, preferably $R^4$ is $CH_2$, and $R^4$ and $R^5$ may be bound together to form a ring, and or $R^4$ and $R^6$ may be bound together to form a ring;

a is an integer that is equal to 0, 1, or 2;

$R^5$ is hydrogen, hydrocarbyl, substituted hydrocarbyl or a functional group, preferably $R^5$ is $CH_2$, and $R^5$ and $R^3$ may be bound together to form a ring;

b is an integer that is equal to 0, 1, or 2;

$R^6$ is carbon or silicon;

each $R^7$ hydrogen;

each $R^8$ is independently selected from the group consisting of hydrogen, methyl, ethyl, propyl, butyl, pentyl, hexyl and the isomers thereof, preferably $R^8$ is hydrogen, methyl, ethyl or propyl, more preferably $R^8$ is hydrogen or methyl, and the $R^8$ groups may be the same or different;

each $R^9$ is independently selected from the group consisting of hydrogen, hydrocarbyl, substituted hydrocarbyl and a functional group, preferably $R^9$ is hydrogen, methyl, ethyl, propyl or phenyl, more preferably $R^9$ is hydrogen, and the $R^9$ groups may be the same or different, and any two $R^9$ groups may be linked together to form a ring, and $R^9$ and $R^8$ may be linked together to form a ring, and $R^9$ and $R^{16}$ may be linked together to form a ring, and $R^9$ and $R^{11}$ may be linked together to form a ring;

$R^{10}$ is -$M^2(R^{16})_h$-where $M^2$ is B, Al, N, P, Si or Ge, h is an integer from 1 to 2, such that the valence of $M^2$ is filled, and $R^{16}$ is hydrogen, hydrocarbyl, substituted hydrocarbyl or a functional group, preferably an arene, and each $R^{16}$ group may be the same or different, and any two $R^{16}$ groups may be linked together to form a ring, preferably, $R^{10}$ is $SiMe_2$, $Si(CH_2)_2$, $Si(CH_2)_3$, $SiPh_2$, $Si(biphenyl)_1$, $Si(biphenyl)_2$, $Si(o-tolyl)_2$, more preferably $R^{10}$ is $SiMe_2$ or $SiPh_2$;

each $R^{11}$ is independently selected from the group consisting of hydrogen, hydrocarbyl, substituted hydrocarbyl and a functional group, preferably $R^{11}$ is hydrogen, methyl, ethyl, propyl or phenyl, more preferably $R^{11}$ is hydrogen, and the $R^{11}$ groups may be the same or different, and the $R^{11}$ groups may be linked together to form a ring, and $R^{11}$ and $R^8$ may be linked together to form a ring, and $R^{11}$ and $R^{16}$ may be linked together to form a ring;

c is an integer=0, 1, or 2;

d is an integer=0, 1, or 2;

e is an integer=0, 1, or 2;

The sum of c, d, and e is 1, 2 or 3, preferably the sum of c, d, and e is 1 or 2, more preferably, the sum of c, d, and e is 1;

$R^{12}$ is carbon or silicon;

$R^{13}$ is hydrogen, hydrocarbyl, substituted hydrocarbyl or a functional group, preferably $CH_2$, and $R^{13}$ and $R^{14}$ may be bound together to form a ring, and $R^{13}$ and $R^{15}$ may be bound together to form a ring, when g is 0;

$R^{14}$ is hydrogen, hydrocarbyl, substituted hydrocarbyl or a functional group, preferably $CH_2$, and $R^{14}$ and $R^{12}$ may be bound together to form a ring when f is 0;

$R^{15}$ is carbon or silicon;

f is an integer that is equal to 0, 1, or 2;

g is an integer that is equal to 0, 1, or 2, provided that if the two $R^1$ groups are linked, then they do not form a butadiene group when M is Zr.

In a preferred embodiment, $R^3$ and $R^6$ do not form a 5 carbon ring. In an alternate embodiment, and or $R^{12}$ and $R^{15}$ do not form a 5 carbon ring. In an alternate embodiment $R^3$ and $R^6$ and $R^{12}$ and $R^{15}$ do not form a 5 carbon ring.

In a preferred embodiment, $R^3$ and $R^6$ do not form a 5 carbon ring when M is Zr. In an alternate embodiment, and or $R^{12}$ and $R^{15}$ do not form a 5 carbon ring when M is Zr. In an alternate embodiment $R^3$ and $R^6$ and $R^{12}$ and $R^{15}$ do not form a 5 carbon ring when M is Zr.

In a preferred embodiment when M is Hf, $R^3$ and $R^6$ form a 5 carbon ring and at least one $R^2$ group attached to the 5 carbon ring is not methyl, preferably at least two $R^2$ groups are not methyl, preferably at three $R^2$ groups are not methyl, preferably all four $R^2$ groups attached to the 5 carbon ring are not methyl.

In an alternate embodiment, when M is Hf, $R^{12}$ and $R^{15}$ form a 5 carbon ring and at least one $R^2$ group attached to the 5 carbon ring is not methyl, preferably at least two $R^2$ groups are not methyl, preferably at three $R^2$ groups are not methyl, preferably all four $R^2$ groups attached to the 5 carbon ring are not methyl.

In another preferred embodiment, M is Hf, and both $R^1$ groups are methyl.

For purposes of this invention and the claims thereto polymerization system is defined to be monomer(s) plus comonomers plus solvent/diluent plus polymer.

In a preferred embodiment, the polymerization system comprises less than 20 wt % aromatic hydrocarbons. Preferably less than 20 wt % toluene.

Preferably, the temperature of the polymerization system is between 100° C. and 250° C., preferably 105 and 225° C., preferably 110 and 220° C., preferably 110 and 190° C., preferably 115 and 170° C., preferably 120 and 150° C., preferably 120 to 140° C. In other embodiments, the temperature is preferably from 100 to 200° C., preferably 105 to 180° C., preferably 110 to 170° C.

Preferably the pressure of the polymerization system is no lower than 10 MPa below the cloud point pressure of the polymerization system, preferably no lower than 5 MPa below the cloud point pressure, preferably above the cloud point pressure, preferably 5 MPa or more above the cloud point pressure, preferably 25 MPa or more, preferably 50 MPa or more, preferably 100 MPa or more. Preferably the pressure is 5 MPa or more, preferably 10 MPa or more, more preferably 25 MPa or more, preferably 27.5 or more, preferably 28.5 or more, preferably 30 MPa or more, more preferably from 5 MPa to 350 MPa. Even more preferably the pressure is between 15 and 200 MPa, preferably 20 and 150 MPa, preferably 25 and 100 MPa, preferably 30 and 75 MPa, most preferably between 25 and 50 MPa.

Preferably solvent and or diluent is present in the polymerization system at 0 to 60 wt %, preferably 0 to 25 wt %, preferably 0 to 20, preferably 0 to 15 preferably 0 to 10 preferably 0 to 5, preferably, 0 to 4, preferably 0 to 3, preferably 0 to 2, preferably 0 to 1 wt %. In another embodiment, the solvent and or diluent is present at 10 weight % or less, preferably less than 7.5 weight %, preferably less than 5 weight %, preferably less than 3 weight %, preferably less than 2 weight %, preferably less than 1 weight %, more preferably less than 0.5 weight %, based upon the weight of all solvent of diluent present. It is expected that in some embodiments, even if no solvent or diluent is added to the reactor some solvent or diluent may enter with the catalyst solution feed.

In a preferred embodiment the olefin monomers are present in the polymerization system at 45 wt % or more, preferably 50 wt % or more, preferably at 55 wt % or more, preferably 60 wt % or more, preferably at 65 wt % or more, preferably 70 wt % or more, preferably at 75 wt % or more, preferably 80 wt % or more, preferably at 85 wt % or more.

In a preferred embodiment propylene is present in the polymerization system at 45 wt % or more, preferably 50 wt % or more, preferably at 55 wt % or more, preferably 60 wt % or more, preferably at 65 wt % or more, preferably 70 wt % or more, preferably at 75 wt % or more, preferably 80 wt % or more, preferably at 85 wt % or more.

In a preferred embodiment propylene and up to 30 mol % of one or more comonomers are present in the polymerization system at 45 wt % or more, preferably 50 wt % or more, preferably at 55 wt % or more, preferably 60 wt % or more, preferably at 65 wt % or more, preferably 70 wt % or more, preferably at 75 wt % or more, preferably 80 wt % or more, preferably at 85 wt % or more.

In particularly preferred embodiments the temperature of the polymerization system is 100° C. or more (preferably between 100 and 170° C.) and the pressure of the polymerization system is 27.5 MPa or more (preferably between 27.5 and 250 MPa). In further particularly preferred embodiments the temperature of the polymerization system is 105° C. or more (preferably between 105 and 170° C.) and the pressure of the polymerization system is 27.5 MPa or more (preferably between 28.5 and 250 MPa). In further particularly preferred embodiments the temperature of the polymerization system is 110° C. or more (preferably between 110 and 170° C.) and the pressure is of the polymerization system is 28.5 MPa or more (preferably between 30 and 220 MPa). In further particularly preferred embodiments the temperature of the polymerization system is between 120 and 160° C. and the pressure of the polymerization system is between 30 and 2000 MPa.

The processes of this invention occur in a supercritical polymerization medium, preferably above the cloud point of the medium. A supercritical state exists for a substance when the substance's temperature and pressure are above its critical point. When the pressure and temperature exceeds the critical state, the fluid is in its supercritical state. The critical pressure and critical temperature of a fluid may be altered by combining it with another fluid, such as a diluent or anther monomer. Thus, for the purposes of this invention and the claims thereto a supercritical polymerization medium is the state where the polymerization medium is present at a temperature above the critical temperature and critical pressure of the medium.

For purposes of this invention and the claims thereto, the critical temperatures (Tc) and critical pressures (Pc) are found in the Handbook of Chemistry and Physics, David R. Lide, Editor-in-Chief, 82nd edition 2001-2002, CRC Press, LLC. New York, 2001. In particular the Tc and Pc of various molecules are defined to be:

| Name | Tc (K) | Pc (MPa) | Name | Tc (K) | Pc (MPa) |
| --- | --- | --- | --- | --- | --- |
| Hexane | 507.6 | 3.025 | Propane | 369.8 | 4.248 |
| Isobutane | 407.8 | 3.640 | Toluene | 591.8 | 4.11 |
| Ethane | 305.3 | 4.872 | Methane | 190.56 | 4.599 |
| Cyclobutane | 460.0 | 4.98 | Butane | 425.12 | 3.796 |
| Cyclopentane | 511.7 | 4.51 | Ethylene | 282.34 | 5.041 |
| 1-butene | 419.5 | 4.02 | Propylene | 364.9 | 4.60 |
| 1-pentene | 464.8 | 3.56 | Cyclopentene | 506.5 | 4.80 |
| Pentane | 469.7 | 3.370 | Isopentane | 460.4 | 3.38 |
| Benzene | 562.05 | 4.895 | Cyclohexane | 553.8 | 4.08 |
| 1-hexene | 504.0 | 3.21 | Heptane | 540.2 | 2.74 |

273.2 K = 0° C.

In a preferred embodiment, the combined amount of monomer(s) and solvent/diluent comprises at least 50 wt % of neat monomer, preferably at least 60 vol % neat monomer, more preferably at least 70 vol %, more preferably at least 80 vol %, more preferably at least 90 vol %, more preferably at least 95 vol %.

In another embodiment, under steady state conditions (as calculated using the mass balance technique), the neat monomer(s)are present at least 40 weight %, where the solvent may be present at 0 to 60 weight %, and the polymer is present at 0.1 to 60 weight %, based upon the weight of the polymer, monomer and solvent/diluent. By steady state conditions is meant that the reactor operates at a constant temperature and pressure (i.e. plus or minus 5° C. and plus or minus 0.5 MPa) for at least 80% of the polymerization residence time (preferably at least 85%, preferably at least 90%, more preferably at least 95%). Total reactor content at steady state is equal to Diluent+Monomer(s)+Polymer, preferably the weight % of each should be 0 to 40, 60 to 100, and 0.01 to 50, respectively, where the total is equal to 100.

In some embodiments, optional comonomer, diluents or other fluids are present in the polymerization medium along with the monomer. Diluents, comonomers and other fluids each modify the media's critical point; and hence, alter the pressure-temperature regime within which a particular medium is in a supercritical state. Diluents, comonomers and other fluids each also modify the phase behavior of the polymerization medium; and hence, alter the pressure-temperature regime within which a particular medium is single phased. Consequently, a two component reaction medium can have two phases above its critical point.

While this disclosure speaks of two phases for neat propylene with dissolved polypropylene converting to a single phase above the reaction mixture's cloud point, the reality is that the phase behavior is more complicated, especially when the reaction medium is more complicated than neat propylene. This added complication can show up anytime the reaction medium contains an additional component, such as a diluent.

The terms "two-phase polymerization system" or "two-phase polymerization medium" mean a system having two and, preferably, only two phases. In certain embodiments, the two phases are referenced as a "first phase" and a "second phase." In certain embodiments, the first phase is or includes a "monomer phase," which includes monomers and may also include solvent and some or all of the product of polymerization. Preferably, however, the monomer phase is substantially free of the polymer product. That is, for example, in a propylene polymerization, the monomer phase can be referred to as the "propylene phase." In certain embodiments, the second phase is or includes a solid phase, which may include products of polymerization, e.g., macromers and polymer product, but not monomers, e.g., propylene. None of the parts of the catalyst system are considered to be part of the polymerization system, although certain parts of the catalyst system can obviously be solid, e.g., supported catalysts. Furthermore, it is contemplated that parts of the catalyst system may be liquid or vapor or part of the vapor/liquid phase that exists in certain embodiments of the process.

Some embodiments select the temperature and pressure so that the polymer produced in the reaction and the reaction medium that solvates it remain single phase, i.e. above the reaction medium's cloud point with that polymer. Other embodiments select the temperature and pressure so that the reaction medium remains supercritical, but at a pressure below the polymer's cloud point in the particular reaction medium. This results in a two phase reaction medium: a polymer rich phase and a polymer lean phase. Some embodiments that are below the polymer's cloud point nonetheless operate above the polymer's crystallization temperature.

Preferred diluents for use in the present invention include one or more of $C_1$-$C_{24}$ alkanes, such as ethane, propane, n-butane, i-butane, n-pentane, i-pentane, n-hexane, toluene, cyclohexane, xylene, mixed hexanes and cyclopentane. Some embodiments select a diluent from hydrocarbon diluents. In some preferred embodiments the diluent comprises one or more of ethane, propane, and isobutane. In some preferred embodiments the diluent is recyclable.

Preferred diluents also include $C_6$ to $C_{150}$ isoparaffins, preferably $C_6$ to $C_{100}$ isoparaffins, preferably $C_6$ to $C_{25}$ isoparaffins, more preferably $C_8$ to $C_{20}$ isoparaffins. By isoparaffin is meant that the paraffin chains possess $C_1$ to $C_{10}$ alkyl branching along at least a portion of each paraffin chain. More particularly, the isoparaffins are saturated aliphatic hydrocarbons whose molecules have at least one carbon atom bonded to at least three other carbon atoms or at least one side chain (i.e., a molecule having one or more tertiary or quaternary carbon atoms), and preferably wherein the total number of carbon atoms per molecule is in the range between 6 to 50, and between 10 and 24 in another embodiment, and from 10 to 15 in yet another embodiment. Various isomers of each carbon number will typically be present. The isoparaffins may also include cycloparaffins with branched side chains, generally as a minor component of the isoparaffin. Preferably the density (ASTM 4052, 15.6/15.6° C.) of these isoparaffins ranges from 0.70 to 0.83 g/cm$^3$; the pour point is –40° C. or less, preferably –50° C. or less, the viscosity (ASTM 445, 25° C.) is from 0.5 to 20 cSt at 25° C.; and the average molecular weights in the range of 100 to 300 g/mol. Suitable isoparaffins are commercially available under the tradename ISOPAR (ExxonMobil Chemical Company, Houston Tex.), and are described in, for example, U.S. Pat. Nos. 6,197,285, 3,818,105 and 3,439,088, and sold commercially as ISOPAR series of isoparaffins. Other suitable isoparaffins are also commercial available under the trade names SHELLSOL (by Shell), SOLTROL (by Chevron Phillips) and SASOL (by Sasol Limited). SHELLSOL is a product of the Royal Dutch/Shell Group of Companies, for example, Shellsol™ (boiling point=215-260° C.). SOLTROL is a product of Chevron Phillips Chemical Co. LP, for example, SOLTROL 220 (boiling point=233-280° C.). SASOL is a product of Sasol Limited (Johannesburg, South Africa), for example, SASOL LPA-210, SASOL-47 (boiling point=238-274° C.).

In another embodiment, preferred diluents include $C_5$ to $C_{25}$ n-paraffins, preferably $C_5$ to $C_{20}$ n-paraffins, preferably $C_5$ to $C_{25}$ n-paraffins having less than 0.1%, preferably less than 0.01% aromatics. Suitable n-paraffins are commercially available under the tradename NORPAR (ExxonMobil Chemical Company, Houston Tex.), and are sold commercially as NORPAR series of n-paraffins. In another embodiment preferred diluents include dearomaticized aliphatic hydrocarbon comprising a mixture of normal paraffins, isoparaffins and cycloparaffins. Typically they are a mixture of $C_4$ to $C_{25}$ normal paraffins, isoparaffins and cycloparaffins, preferably $C_5$ to $C_{18}$, preferably $C_5$ to $C_{12}$. They contain very low levels of aromatic hydrocarbons, preferably less than 0.1, preferably less than 0.01 weight % aromatics. Suitable dearomatized aliphatic hydrocarbons are commercially available under the tradename EXXSOL (ExxonMobil Chemical Company, Houston Tex.), and are sold commercially as EXXSOL series of dearomaticized aliphatic hydrocarbons.

In another embodiment the diluent comprises up to 20 weight % of oligomers of $C_6$ to $C_{14}$ olefins and/or oligomers of linear olefins having 6 to 14 carbon atoms, more preferably 8 to 12 carbon atoms, more preferably 10 carbon atoms having a Kinematic viscosity of 10 or more (as measured by ASTM D 445); and preferably having a viscosity index ("VI"), as determined by ASTM D-2270 of 100 or more.

In another embodiment the diluent comprises up to 20 weight % of oligomers of $C_{20}$ to $C_{1500}$ paraffins, preferably $C_{40}$ to $C_{1000}$ paraffins, preferably $C_{50}$ to $C_{750}$ paraffins, preferably $C_{50}$ to $C_{500}$ paraffins. In another embodiment the diluent comprises up to 20 weight % of oligomers of 1-pentene, 1-hexene, 1-heptene, 1-octene, 1-nonene, 1-decene, 1-undecene and 1-dodecene. Such oligomers are commercially available as SHF and SuperSyn PAO's (ExxonMobil Chemical Company, Houston Tex.). Other useful oligomers include those sold under the tradenames Synfluid™ available from ChevronPhillips Chemical Co. in Pasedena Tex., Durasyn™ available from BP Amoco Chemicals in London England, Nexbase™ available from Fortum Oil and Gas in Finland, Synton™ available from Crompton Corporation in Middlebury Conn., USA, EMERY™ available from Cognis Corporation in Ohio, USA.

With regard to propylene polymerization media, preferred monomers and diluents are those that are soluble in and inert to propylene and any other polymerization components at the polymerization temperatures and pressures.

As mentioned above, the polymerization processes described herein are preferably run under supercritical conditions. This characteristic provides a lower pressure and temperature limit—the critical temperature and pressure of the reaction medium. Temperature and pressure are also constrained on the upper end. The upper temperature range is the decomposition or ceiling temperature of polypropylene. The following temperatures, in ° C., are useful lower temperature limits for all invention processes: 110, 120, 130, 140, and 150. The following temperatures, in ° C., are useful upper temperature limits for all invention processes: 160, 170, 180, 190, 200, and 220.

In another preferred embodiment the polymerization temperature is from 92 to 330° C., preferably 95 to 250° C., more preferably 100 to 200° C., more preferably 105 to 150° C., more preferably 120 to 160° C. more preferably 115 to 140° C., more preferably 112 to 160° C.

Theoretically, pressure can go as high as can be commercially contained. More practically, pressure is limited by the desired properties of the resulting polypropylene. The following pressures, in MPa, are useful lower pressure limits for all invention processes: 4.62, 5, 10, 15, 30, 50, 60, 80, 100, 120, 140, 150, 160, 180, 200, 250, 260, 300, 330, 350, 400, 440, 500, and 600. The following pressures, in MPa, are useful upper pressure limits for all invention processes: 10, 15, 30, 50, 60, 80, 100, 120, 140, 150, 160, 180, 200, 250, 260, 300, 330, 350, 400, 440, 500, 600, and 1000 MPa.

In a preferred embodiment the polymerization pressure is from 4.6 to 1000 MPa, preferably 15 to 500 MPa, more preferably 15 to 400 MPa, more preferably 15 to 300 MPa, more preferably 15 to 250 MPa, more preferably 15 to 200 MPa, more preferably 15 to 400 MPa, more preferably 15 to 190 MPa, more preferably 154.6 to 180 MPa, more preferably 15 to 170 MPa. In another embodiment the lower limit in all of the above ranges is 20 MPa, rather than 15 MPa. In another embodiment the lower limit in all of the above ranges is 25 MPa, rather than 15 MPa. In another embodiment the lower limit in all of the above ranges is 30 MPa, rather than 15 MPa. In another embodiment the lower limit in all of the above ranges is 40 MPa, rather than 15 MPa. In another embodiment the lower limit in all of the above ranges is 50 MPa, rather than 15 MPa.

It is expected that any temperature range can be combined with any pressure range, provided that the chosen temperature and pressure are such that the reaction medium is above its cloud point (or within 10 MPa of the cloud point).

Temperatures above 112° C. and pressures between 80-250 MPa are particularly useful. Likewise in another embodiment, temperatures above 105° C. and pressures between 28 MPa and 200 MPa are particularly useful.

Monomers

The process described herein can be used to polymerize any monomer having three or more carbon atoms. Preferred monomers include propylene, butene, hexene, decene and octene.

In a preferred embodiment the processes of this invention are used to polymerize any unsaturated monomer or monomers. Preferred monomers include $C_3$ to $C_{100}$ olefins, preferably $C_3$ to $C_{60}$ olefins, preferably $C_3$ to $C_{40}$ olefins preferably $C_3$ to $C_{20}$ olefins, preferably $C_3$ to $C_{12}$ olefins. In some embodiments preferred monomers include linear, branched or cyclic alpha-olefins, preferably $C_3$ to $C_{100}$ alpha-olefins, preferably $C_3$ to $C_{60}$ alpha-olefins, preferably $C_3$ to $C_{40}$ alpha-olefins preferably $C_3$ to $C_{20}$ alpha-olefins, preferably $C_3$ to $C_{12}$ alpha-olefins. Preferred olefin monomers may be one or more of propylene, butene, pentene, hexene, heptene, octene, nonene, decene, dodecene, 4-methyl-pentene-1,3-methyl pentene-1,3,5,5-trimethyl hexene 1, and 5-ethyl-1-nonene.

In another embodiment the polymer produced herein is a copolymer of one or more linear or branched $C_3$ to $C_{30}$ prochiral alpha-olefins or $C_5$ to $C_{30}$ ring containing olefins or combinations thereof capable of being polymerized by either stereospecific and non-stereospecific catalysts. Prochiral, as used herein, refers to monomers that favor the formation of isotactic or syndiotactic polymer when polymerized using stereospecific catalyst(s).

Preferred monomers may also include aromatic-group-containing monomers containing up to 30 carbon atoms. Suitable aromatic-group-containing monomers comprise at least one aromatic structure, preferably from one to three, more preferably a phenyl, indenyl, fluorenyl, or naphthyl moiety. The aromatic-group-containing monomer further comprises at least one polymerizable double bond such that after polymerization, the aromatic structure will be pendant from the polymer backbone. The aromatic-group containing monomer may further be substituted with one or more hydrocarbyl groups including but not limited to $C_1$ to $C_{10}$ alkyl groups. Additionally two adjacent substitutions may be joined to form a ring structure. Preferred aromatic-group-containing monomers contain at least one aromatic structure appended to a polymerizable olefinic moiety. Particularly preferred aromatic monomers include styrene, alpha-methylstyrene, para-alkylstyrenes, vinyltoluenes, vinylnaphthalene, allyl benzene, and indene, especially styrene, paramethyl styrene, 4-phenyl-1-butene and allyl benzene.

Non aromatic cyclic group containing monomers are also preferred. These monomers can contain up to 30 carbon atoms. Suitable non-aromatic cyclic group containing monomers preferably have at least one polymerizable olefinic group that is either pendant on the cyclic structure or is part of the cyclic structure. The cyclic structure may also be further substituted by one or more hydrocarbyl groups such as, but not limited to, $C_1$ to $C_{10}$ alkyl groups. Preferred non-aromatic cyclic group containing monomers include vinylcyclohexane, vinylcyclohexene, vinylnorbornene, ethylidene norbornene, cyclopentadiene, cyclopentene, cyclohexene, cyclobutene, vinyladamantane, norbornene, and the like.

Preferred diolefin monomers useful in this invention include any hydrocarbon structure, preferably $C_4$ to $C_{30}$, having at least two unsaturated bonds, wherein at least two of the unsaturated bonds are readily incorporated into a polymer by either a stereospecific or a non-stereospecific catalyst(s). It is further preferred that the diolefin monomers be selected from alpha, omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

Non-limiting examples of preferred polar unsaturated monomers include 6-nitro-1-hexene, N-methylallylamine, N-allylcyclopentylamine, N-allylhexylamine, methyl vinyl ketone, ethyl vinyl ketone, 5-hexen-2-one, 2-acetyl-5-norbornene, 7-syn methoxymethyl-5-norbornen-2-one, acrolein, 2,2-dimethyl-4-pentenal, undecylenic aldehyde, 2,4-dimethyl-2,6-heptadienal, acrylic acid, vinylacetic acid, 4-pentenoic acid, 2,2-dimethyl-4-pentenoic acid, 6-heptenoic acid, trans-2,4-pentadienoic acid, 2,6-heptadienoic acid, nona-fluoro-1-hexene, allyl alcohol, 7-octene-1,2-diol, 2-methyl-3-buten-1-ol, 5-norbornene-2-carbonitrile, 5-norbornene-2-carboxaldehyde, 5-norbornene-2-carboxylic acid, cis-5-norbornene-endo-2,3-dicarboxylic acid, 5-norbornene-2,2,-dimethanol, cis-5-norbornene-endo-2,3-dicarboxylic anhydride, 5-norbornene-2-endo-3-endo-dimethanol, 5-norbornene-2-endo-3-exo-dimethanol, 5-norbornene-2-methanol, 5-norbornene-2-ol, 5-norbornene-2-yl acetate, 1-[2-(5-norbornene-2-yl)ethyl]-3,5,7,9,11,13,15-heptacyclopentylpentacyclo[9.5.1.1$^{3,9}$.1$^{5,15}$.1$^{7,13}$]octasiloxane, 2-benzoyl-5-norbornene, allyl 1,1,2,2,-tetrafluoroethyl ether, acrolein dimethyl acetal, butadiene monoxide, 1,2- epoxy-7-octene, 1,2-epoxy-9-decene, 1,2-epoxy-5-hexene, 2-methyl-2-vinyloxirane, allyl glycidyl ether, 2,5-dihydrofuran, 2-cyclopenten-1-one ethylene ketal, allyl disulfide, ethyl acrylate, methyl acrylate.

In a preferred embodiment the processes described herein may be used to produce homopolymers or copolymers. (For the purposes of this invention and the claims thereto a copolymer may comprise two, three, four or more different monomer units.) Preferred polymers produced herein include homopolymers or copolymers of any of the above monomers. In a preferred embodiment the polymer is a homopolymer of any $C_3$ to $C_{12}$ alpha-olefin. Preferably the polymer is a homopolymer of propylene. In another embodiment the polymer is a copolymer comprising propylene and ethylene, preferably the copolymer comprises less than 40 weight % ethylene, more preferably less than 30 weight % ethylene, preferably the copolymer comprises less than 20 weight % ethylene, more preferably less than 10 weight % ethylene. In another embodiment the polymer is a copolymer comprising propylene and one or more of any of the monomers listed above. In another preferred embodiment the copolymers comprises one or more diolefin comonomers, preferably one or more $C_2$ to $C_{40}$ diolefins.

In another preferred embodiment the polymer produced herein is a copolymer of propylene and one or more $C_2$ or $C_4$ to $C_{20}$ linear, branched or cyclic monomers, preferably one or more $C_2$ or $C_4$ to $C_{12}$ linear, branched or cyclic alpha-olefins. Preferably the polymer produced herein is a copolymer of propylene and one or more of ethylene, butene, pentene, hexene, heptene, octene, nonene, decene, dodecene, 4-methyl-pentene-1, 3-methyl pentene-1, and 3,5, 5-trimethyl hexene 1.

In a preferred embodiment the copolymers described herein comprise at least 50 mole % of a first monomer and up to 50 mole % of other monomers.

In another embodiment, the polymer comprises:
a first monomer present at from 40 to 95 mole %, preferably 50 to 90 mole %, preferably 60 to 80 mole %, and
a comonomer present at from 5 to 40 mole %, preferably 10 to 60 mole %, more preferably 20 to 40 mole %, and
a termonomer present at from 0 to 10 mole %, more preferably from 0.5 to 5 mole %, more preferably 1 to 3 mole %.

In a preferred embodiment the first monomer comprises one or more of any $C_3$ to $C_8$ linear branched or cyclic alpha-olefins, including propylene, butene, (and all isomers thereof), pentene (and all isomers thereof), hexene (and all isomers thereof), heptene (and all isomers thereof), and octene (and all isomers thereof). Preferred monomers include propylene, 1-butene, 1-hexene, 1-octene, cyclohexene, cyclooctene, hexadiene, cyclohexadiene and the like.

In a preferred embodiment the comonomer comprises one or more of any $C_2$ to $C_{40}$ linear, branched or cyclic alpha-olefins (provided ethylene, if present, is present at 5 mole % or less), including ethylene, propylene, butene, pentene, hexene, heptene, and octene, nonene, decene, undecene, dodecene, hexadecene, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, and cyclohexene.

In a preferred embodiment the termonomer comprises one or more of any $C_2$ to $C_{40}$ linear, branched or cyclic alpha-olefins, (provided ethylene, if present, is present at 5 mole % or less), including ethylene, propylene, butene, pentene, hexene, heptene, and octene, nonene, decene, un-decene, do-decene, hexadecene, butadiene, hexadiene, heptadiene, pentadiene, octadiene, nonadiene, decadiene, dodecadiene, styrene, 3,5,5-trimethyl hexene-1,3-methylpentene-1,4-methylpentene-1, cyclopentadiene, and cyclohexene.

In a preferred embodiment the polymers described above further comprise one or more dienes at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more.

In another embodiment the processes describe herein are used to produce propylene copolymers with other monomer units, such as ethylene, other α-olefin, α-olefinic diolefin, or non-conjugated diolefin monomers, for example, $C_4$-$C_{20}$ olefins, $C_4$-$C_{20}$ diolefins, $C_4$-$C_{20}$ cyclic olefins, $C_8$-$C_{20}$ styrenic olefins. Other unsaturated monomers besides those specifically described above may be copolymerized using the invention processes, for example, styrene, alkyl-substituted styrene, ethylidene norbornene, norbornadiene, dicyclopentadiene, vinylcyclohexane, vinylcyclohexene, acrylates, and other olefinically-unsaturated monomers, including other cyclic olefins, such as cyclopentene, norbornene, and alkyl-substituted norbornenes. Copolymerization can also incorporate α-olefinic macromonomers produced in-situ or added from another source. Some invention embodiments limit the copolymerization of α-olefinic macromonomers to macromonomers with 2000 or less mer units. U.S. Pat. No. 6,300,451 discloses many useful comonomers. That disclosure refers to comonomers as "a second monomer".

In another embodiment, when propylene copolymers are desired, the following monomers can be copolymerized with propylene: ethylene, but-1-ene, hex-1-ene, 4-methylpent-1-ene, dicyclopentadiene, norbornene, $C_4$-$C_{2000}$, $C_4$-$C_{200}$, or $C_4$-$C_{40}$ linear or branched, α,ω-dienes; $C_4$-$C_{2000}$, $C_4$-$C_{200}$, or $C_4$-$C_{40}$ cyclic olefins; and $C_4$-$C_{2000}$, $C_4$-$C_{200}$, or $C_4$-$C_{40}$ linear or branched α-olefins.

Other Primary Monomer

Some invention processes polymerize but-1-ene ($T_c$=146.5° C.; $P_c$=3.56 MPa), pent-1-ene ($T_c$=191.8; $P_c$=3.56 MPa), hex-1-ene ($T_c$=230.8; $P_c$=3.21 MPa), and 3-methyl-but-1-ene ($T_c$=179.7; $P_c$=3.53 MPa) using these monomers or mixtures comprising the monomers at supercritical conditions as the reaction medium or solvent. These processes can employ at least one of but-1-ene, pent-1-ene, or 3-methyl-but-1-ene as monomer. These processes can also employ reaction media that comprise but-1-ene, pent-1-ene, or 3-methyl-but-1-ene. These processes can employ reaction media that contain greater than 50 wt. % of but-1-ene, pent-1-ene, or 3-methyl-but-1-ene. Of course, these compounds can be freely mixed with each other and with propylene as monomer, bulk reaction media, or both.

Catalyst Systems

The processes described herein are preferably used with a catalyst system comprising a metallocene catalyst compounds in combination with an activator. A catalyst system is defined to be the combination of at least one catalyst compound and at least one activator.

Catalyst Compounds

Catalyst compounds that may be used in the processes of this invention include chiral metallocenes containing specifically substituted indenyl ligands in combination with an activator and optionally an additional cocatalyst. Preferred metallocenes with specifically substituted indenyl ligands are represented in the following Formula 1:

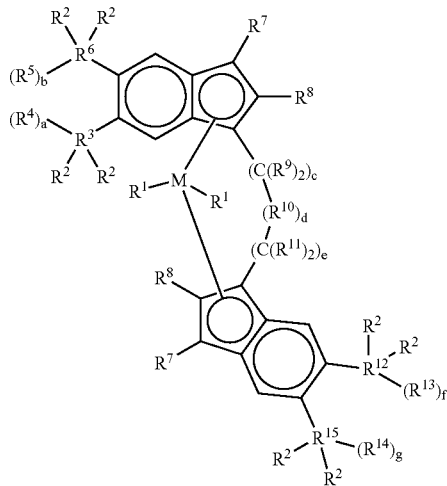

where:

M is a transition metal selected form group 4 of the periodic table, preferably Zr or Hf, most preferably Hf;

each $R^1$ is independently selected from the group consisting of hydrogen, hydrocarbyl, substituted hydrocarbyl and a functional group, preferably, $R^1$ is hydrogen, a hydrocarbon or a halide, preferably $R^1$ is a hydride, even more preferably $R^1$ is selected from the group consisting of methyl, ethyl, trimethylsilylmethyl, trimethylsilyl, phenyl, naphthyl, allyl, and benzyl; even more preferably, $R^1$ is methyl, and $R^1$ may be linked, and the $R^1$ groups may be the same or different;

each $R^2$ is independently selected from the group consisting of hydrogen, hydrocarbyl, substituted hydrocarbyl and a functional group, preferably $R^2$ is hydrogen, methyl, ethyl or propyl, more preferably, $R^2$ is methyl, and the $R^2$ groups may be the same or different, and any two $R^2$ groups may be linked together to form an aliphatic or aromatic ring;

$R^3$ is carbon or silicon;

$R^4$ is hydrogen, hydrocarbyl, substituted hydrocarbyl or a functional group, preferably $R^4$ is $CH_2$, and $R^4$ and $R^5$ may be bound together to form a ring, and or $R^4$ and $R^6$ may be bound together to form a ring;

a is an integer that is equal to 0, 1, or 2;

$R^5$ is hydrogen, hydrocarbyl, substituted hydrocarbyl or a functional group, preferably $R^5$ is $CH_2$, and $R^5$ and $R^3$ may be bound together to form a ring;

b is an integer that is equal to 0, 1, or 2;

$R^6$ is carbon or silicon;

each $R^7$ is independently selected from the group consisting of hydrogen, hydrocarbyl, substituted hydrocarbyl and a functional group. The $R^7$ may be the same or different. $R^7$ and $R^8$ may be linked together to form an aliphatic or aromatic ring, preferably $R^7$ is hydrogen, methyl, ethyl or propyl, more preferably $R^7$ is hydrogen, and the $R^7$ groups may be the same or different, and $R^7$ and $R^8$ may be linked together to form an aliphatic or aromatic ring;

each $R^8$ is independently selected from the group consisting of hydrogen, hydrocarbyl, substituted hydrocarbyl and a functional group, preferably $R^8$ is hydrogen, methyl, ethyl or propyl, more preferably $R^8$ is hydrogen or methyl, and the $R^8$ groups may be the same or different;

each $R^9$ is independently selected from the group consisting of hydrogen, hydrocarbyl, substituted hydrocarbyl and a functional group, preferably $R^9$ is hydrogen, methyl, ethyl, propyl or phenyl, more preferably $R^9$ is hydrogen, and the $R^9$ groups may be the same or different, and any two $R^9$ groups may be linked together to form a ring, and $R^9$ and $R^8$ may be linked together to form a ring, and $R^9$ and $R^{16}$ may be linked together to form a ring, and $R^9$ and $R^{11}$ may be linked together to form a ring;

$R^{10}$ is $-M^2(R^{16})_h$-where $M^2$ is B, Al, N, P, Si or Ge, h is an integer from 1 to 2, such that the valence of $M^2$ is filled, and $R^{16}$ is hydrogen, hydrocarbyl, substituted hydrocarbyl or a functional group, preferably an arene, and each $R^{16}$ group may be the same or different, and any two $R^{16}$ groups may be linked together to form a ring, preferably, $R^{10}$ is $SiMe_2$, $Si(CH_2)_2$, $Si(CH_2)_3$, $SiPh_2$, $Si(biphenyl)_1$, $Si(biphenyl)_2$, $Si(o-tolyl)_2$, more preferably $R^{10}$ is $SiMe_2$ or $SiPh_2$;

each $R^{11}$ is independently selected from the group consisting of hydrogen, hydrocarbyl, substituted hydrocarbyl and a functional group, preferably $R^{11}$ is hydrogen, methyl, ethyl, propyl or phenyl, more preferably $R^{11}$ is hydrogen, and the $R^{11}$ groups may be the same or different, and the $R^{11}$ groups may be linked together to form a ring, and $R^{11}$ and $R^8$ may be linked together to form a ring, and $R^{11}$ and $R^{16}$ may be linked together to form a ring;

c is an integer=0, 1, or 2;

d is an integer=0, 1, or 2;

e is an integer=0, 1, or 2;

The sum of c, d, and e is 1, 2 or 3, preferably the sum of c, d, and e is 1 or 2, more preferably, the sum of c, d, and e is 1;

$R^{12}$ is carbon or silicon;

$R^{13}$ is hydrogen, hydrocarbyl, substituted hydrocarbyl or a functional group, preferably $CH_2$, and $R^{13}$ and $R^{14}$ may be bound together to form a ring, and $R^{13}$ and $R^{15}$ may be bound together to form a ring, when g is 0;

$R^{14}$ is hydrogen, hydrocarbyl, substituted hydrocarbyl or a functional group, preferably $CH_2$, and $R^{14}$ and $R^{12}$ may be bound together to form a ring when f is 0;

$R^{15}$ is carbon or silicon;

f is an integer that is equal to 0, 1, or 2;

g is an integer that is equal to 0, 1, or 2, provided that if the two $R^1$ groups are linked, then they do not form a butadiene group when M is Zr.

In a preferred embodiment,

M is a transition metal selected form group 4 of the periodic table, preferably Zr or Hf, most preferably Hf;

each $R^1$ is independently selected from the group consisting of hydrogen, hydrocarbyl, substituted hydrocarbyl and a functional group, preferably, $R^1$ is hydrogen, a hydrocarbon or a halide, preferably $R^1$ is a hydride, even more preferably $R^1$ is selected from the group consisting of methyl, ethyl, trimethylsilylmethyl, trimethylsilyl, phenyl, naphthyl, allyl, and benzyl; even more preferably, $R^1$ is methyl, and $R^1$ may be linked, and the $R^1$ groups may be the same or different;

each $R^2$ is independently selected from the group consisting of methyl, ethyl, propyl, butyl, pentyl, hexyl and the isomers thereof, provided that when $R^3$ and $R^6$ and or $R^{12}$ and $R^{15}$ form a 5 carbon ring, then each $R^2$ is independently selected from the group consisting of ethyl, propyl, butyl, pentyl, hexyl and the isomers thereof, preferably $R^2$ is methyl, ethyl or propyl, more preferably, $R^2$ is methyl, and the $R^2$ groups may be the same or different;

$R^3$ is carbon or silicon;
$R^4$ is hydrogen, hydrocarbyl, substituted hydrocarbyl or a functional group, preferably $R^4$ is CH$_2$, and $R^4$ and $R^5$ may be bound together to form a ring, and or $R^4$ and $R^6$ may be bound together to form a ring;
a is an integer that is equal to 0, 1, or 2;
$R^5$ is hydrogen, hydrocarbyl, substituted hydrocarbyl or a functional group, preferably $R^5$ is CH$_2$, and $R^5$ and $R^3$ may be bound together to form a ring;
b is an integer that is equal to 0, 1, or 2;
$R^6$ is carbon or silicon;
each $R^7$ hydrogen;
each $R^8$ is independently selected from the group consisting of hydrogen, methyl, ethyl, propyl, butyl, pentyl, hexyl and the isomers thereof, preferably $R^8$ is hydrogen, methyl, ethyl or propyl, more preferably $R^8$ is hydrogen or methyl, and the $R^8$ groups may be the same or different;
each $R^9$ is independently selected from the group consisting of hydrogen, hydrocarbyl, substituted hydrocarbyl and a functional group, preferably $R^9$ is hydrogen, methyl, ethyl, propyl or phenyl, more preferably $R^9$ is hydrogen, and the $R^9$ groups may be the same or different, and any two $R^9$ groups may be linked together to form a ring, and $R^9$ and $R^8$ may be linked together to form a ring, and $R^9$ and $R^{16}$ may be linked together to form a ring, and $R^9$ and $R^{11}$ may be linked together to form a ring;
$R^{10}$ is -M$^2$(R$^{16}$)$_n$-where M$^2$ is B, Al, N, P, Si or Ge, h is an integer from 1 to 2, such that the valence of M$^2$ is filled, and R$^{16}$ is hydrogen, hydrocarbyl, substituted hydrocarbyl or a functional group, preferably an arene, and each R$^{16}$ group may be the same or different, and any two R$^{16}$ groups may be linked together to form a ring, preferably, R$^{10}$ is SiMe$_2$, Si(CH$_2$)$_2$, Si(CH$_2$)$_3$, SiPh$_2$, Si(biphenyl)$_1$, Si(biphenyl)$_2$, Si(o-tolyl)$_2$, more preferably R$^{10}$ is SiMe$_2$ or SiPh$_2$;
each $R^{11}$ is independently selected from the group consisting of hydrogen, hydrocarbyl, substituted hydrocarbyl and a functional group, preferably $R^{11}$ is hydrogen, methyl, ethyl, propyl or phenyl, more preferably $R^{11}$ is hydrogen, and the $R^{11}$ groups may be the same or different, and the $R^{11}$ groups may be linked together to form a ring, and $R^{11}$ and $R^8$ may be linked together to form a ring, and $R^{11}$ and $R^{16}$ may be linked together to form a ring;
c is an integer=0, 1, or 2;
d is an integer=0, 1, or 2;
e is an integer=0, 1, or 2;
The sum of c, d, and e is 1, 2 or 3, preferably the sum of c, d, and e is 1 or 2, more preferably, the sum of c, d, and e is 1;
$R^{12}$ is carbon or silicon;
$R^{13}$ is hydrogen, hydrocarbyl, substituted hydrocarbyl or a functional group, preferably CH$_2$, and $R^{13}$ and $R^{14}$ may be bound together to form a ring, and $R^{13}$ and $R^{15}$ may be bound together to form a ring, when g is 0;
$R^{14}$ is hydrogen, hydrocarbyl, substituted hydrocarbyl or a functional group, preferably CH$_2$, and $R^{14}$ and $R^{12}$ may be bound together to form a ring when f is 0;
$R^{15}$ is carbon or silicon;
f is an integer that is equal to 0, 1, or 2;
g is an integer that is equal to 0, 1, or 2,
provided that if the two $R^1$ groups are linked, then they do not form a butadiene group when M is Zr.

In a preferred embodiment, $R^3$ and $R^6$ do not form a 5 carbon ring. In an alternate embodiment, and or $R^{12}$ and $R^{15}$ do not form a 5 carbon ring. In an alternate embodiment $R^3$ and $R^6$ and $R^{12}$ and $R^{15}$ do not form a 5 carbon ring.

In a preferred embodiment, $R^3$ and $R^6$ do not form a 5 carbon ring when M is Zr. In an alternate embodiment, and or $R^{12}$ and $R^{15}$ do not form a 5 carbon ring when M is Zr.

In an alternate embodiment $R^3$ and $R^6$ and $R^{12}$ and $R^{15}$ do not form a 5 carbon ring when M is Zr.

In a preferred embodiment when M is Hf, $R^3$ and $R^6$ form a 5 carbon ring and at least one $R^2$ group attached to the 5 carbon ring is not methyl, preferably at least two $R^2$ groups are not methyl, preferably at three $R^2$ groups are not methyl, preferably all four $R^2$ groups attached to the 5 carbon ring are not methyl.

In an alternate embodiment, when M is Hf, $R^{12}$ and $R^{15}$ form a 5 carbon ring and at least one $R^2$ group attached to the 5 carbon ring is not methyl, preferably at least two $R^2$ groups are not methyl, preferably at three $R^2$ groups are not methyl, preferably all four $R^2$ groups attached to the 5 carbon ring are not methyl.

In another preferred embodiment, M is Hf, and both $R^1$ groups are methyl.

Substituted hydrocarbyl radicals (also called substituted hydrocarbyls) are radicals in which at least one hydrocarbyl hydrogen atom has been substituted with at least one heteroatom or heteroatom containing group.

The term "hydrocarbyl radical" is sometimes used interchangeably with "hydrocarbyl" throughout this document. For purposes of this disclosure, "hydrocarbyl radical" encompasses radicals containing carbon, hydrogen and optionally silicon atoms, preferably 1 to 100 carbon atoms, hydrogen and optionally silicon. These radicals can be linear, branched, or cyclic including polycyclic. These radicals can be saturated, partially unsaturated or fully unsaturated, and when cyclic, may be aromatic or non-aromatic.

Hydrocarbyls may be arenes. An arene is a substituted or unsubstituted aromatic hydrocarbon. Arenes may be monocyclic, polycyclic, hydrocarbon ring assemblies or fused ring systems. Arenes may be substituted or unsubstituted. Substituted hydrocarbyls may be arenes containing functional groups. As such, substituted hydrocarbyls may be heterocyclics, polyheterocyclics, heterocyclic ring assemblies or fused heterocyclic ring systems.

In some embodiments, the hydrocarbyl radical is selected from methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, or triacontynyl isomers. For this disclosure, when a radical is listed it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

Functional groups are heteroatoms of groups 1-17 of the periodic table either alone or connected to other elements by covalent or other interactions such as ionic, van der Waals forces, or hydrogen bonding. Examples of functional groups include fluoride, chloride, bromide, iodide, carboxylic acid, acid halide, carboxylic ester, carboxylic salt, carboxylic anhydride, aldehyde and their chalcogen (Group 14) analogues, alcohol and phenol, ether, peroxide and hydroperoxide, carboxylic amide, hydrazide and imide, amidine and other nitrogen analogues of amides, nitrile, amine and imine, azo, nitro, other nitrogen compounds, sulfur acids, selenium acids, thiols, sulfides, sulfoxides, sulfones, phosphines, phosphates, other phosphorus compounds, silanes, boranes, borates, alanes, aluminates. Functional groups may also be taken broadly to include organic polymer supports or inorganic support material such as alumina, and silica.

In a preferred embodiment, the metallocene catalyst compounds used herein are represented by the Formula 2 below:

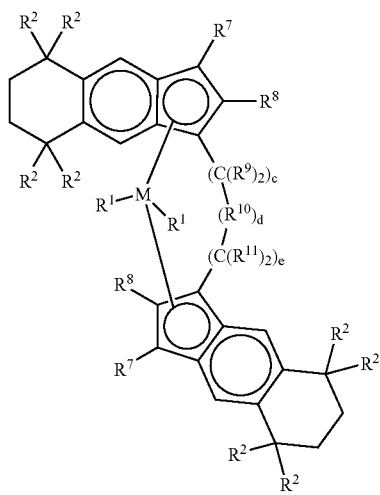

where:

M is a transition metal selected from group 4 of the periodic table, preferably Zr, Hf or Ti, preferably Zr or Hf, most preferably Hf;

each $R^1$ is independently selected from the group consisting of hydrogen, hydrocarbyl, substituted hydrocarbyl and a functional group, preferably $R^1$ is a hydrogen, a hydrocarbon or a halide, more preferably $R^1$ is a hydride, methyl, ethyl, trimethylsilylmethyl, trimethylsilyl, phenyl, naphthyl, allyl, or benzyl, even more preferably $R^1$ is methyl, and the two $R^1$ groups may be the same or different, and the two $R^1$ groups may be linked;

each $R^2$ is independently selected from the group consisting of hydrogen, hydrocarbyl, substituted hydrocarbyl and a functional group, preferably, $R^2$ is hydrogen, methyl, ethyl or propyl, more preferably $R^2$ is methyl, and the $R^2$ groups may be the same or different and any two $R^2$ groups may be linked together to form an aliphatic or aromatic ring (alternately at least one $R^2$ group is not hydrogen, preferably all $R^2$ groups are not hydrogen);

each $R^7$ is independently selected from the group consisting of hydrogen, hydrocarbyl, substituted hydrocarbyl and a functional group, preferably $R^7$ is hydrogen, methyl, ethyl or propyl, more preferably $R^7$ is hydrogen, and the $R^7$ groups may be the same or different, and $R^7$ and $R^8$ may be linked together to form an aliphatic or aromatic ring;

each $R^8$ is independently selected from the group consisting of hydrogen, hydrocarbyl, substituted hydrocarbyl and a functional group, preferably $R^8$ is hydrogen, methyl, ethyl or propyl, more preferably, $R^8$ is hydrogen or methyl, and the $R^8$ groups may be the same or different;

each $R^9$ is independently selected from the group consisting of hydrogen, hydrocarbyl, substituted hydrocarbyl and a functional group, preferably $R^9$ is hydrogen, methyl, ethyl, propyl or phenyl, more preferably $R^9$ is hydrogen, and the $R^9$ groups may be the same or different, and any two $R^9$ groups may be linked together to form a ring, and $R^9$ and $R^8$ may be linked together to form a ring, and $R^9$ and $R^{11}$ may be linked together to form a ring;

$R^{10}$ is -$M^2(R^{16})_h$-where $M^2$ is B, Al, N, P, Si or Ge, h is an integer from 1 to 2, such that the valence of $M^2$ is filled, and $R^{16}$ is hydrogen, hydrocarbyl, substituted hydrocarbyl or a functional group, preferably an arene, and each $R^{16}$ group may be the same or different, and any two $R^{16}$ groups may be linked together to form a ring, preferably, $R^{10}$ is SiMe$_2$, Si(CH$_2$)$_2$, Si(CH$_2$)$_3$, SiPh$_2$, Si(biphenyl)$_1$, Si(biphenyl)$_2$, Si(o-tolyl)$_2$, more preferably $R^{10}$ is SiMe$_2$ or SiPh$_2$;

each $R^{11}$ is independently selected from the group consisting of hydrogen, hydrocarbyl, substituted hydrocarbyl and a functional group, preferably $R^{11}$ is hydrogen, methyl, ethyl, propyl or phenyl, more preferably $R^{11}$ is hydrogen, and the $R^{11}$ groups may be the same or different, and the $R^{11}$ groups may be linked together to form a ring, and $R^{11}$ and $R^8$ may be linked together to form a ring;

c is an integer=0, 1, or 2;

d is an integer=0, 1, or 2;

e is an integer=0, 1, or 2;

The sum of c, d, and e is 1, 2 or 3, preferably the sum of c, d, and e is 1 or 2, more preferably, the sum of c, d, and e is 1;

provided that if the two $R^1$ groups are linked, then they do not form a butadiene group when M is Zr;

M is a transition metal selected from group 4 of the periodic table, preferably Zr or Hf, most preferably Hf;

each $R^1$ is independently selected from the group consisting of hydrogen, hydrocarbyl, substituted hydrocarbyl and a functional group, preferably $R^1$ is a hydrogen, a hydrocarbon or a halide, more preferably $R^1$ is a hydride, methyl, ethyl, trimethylsilylmethyl, trimethylsilyl, phenyl, naphthyl, allyl, or benzyl, even more preferably $R^1$ is methyl, and the two $R^1$ groups may be the same or different, and the two $R^1$ groups may be linked;

each $R^2$ is independently selected from the group consisting of methyl, ethyl, propyl, butyl, pentyl, hexyl and the isomers thereof, provided that when $R^3$ and $R^6$ and or $R^{12}$ and $R^{15}$ form a 5 carbon ring, then each $R^2$ is independently selected from the group consisting of ethyl, propyl, butyl, pentyl, hexyl and the isomers thereof, preferably $R^2$ is methyl, ethyl or propyl, more preferably, $R^2$ is methyl, and the $R^2$ groups may be the same or different;

each $R^7$ is hydrogen;

each $R^8$ is independently selected from the group consisting of hydrogen, methyl, ethyl, propyl, butyl, pentyl, hexyl and the isomers thereof, preferably $R^8$ is hydrogen, methyl, ethyl or propyl, more preferably, $R^8$ is hydrogen or methyl, and the $R^8$ groups may be the same or different;

each $R^9$ is independently selected from the group consisting of hydrogen, hydrocarbyl, substituted hydrocarbyl and a functional group, preferably $R^9$ is hydrogen, methyl, ethyl, propyl or phenyl, more preferably $R^9$ is hydrogen, and the $R^9$ groups may be the same or different, and any two $R^9$ groups may be linked together to form a ring, and $R^9$ and $R^8$ may be linked together to form a ring, and $R^9$ and $R^{11}$ may be linked together to form a ring;

$R^{10}$ is $-M^2(R^{16})_h$-where $M^2$ is B, Al, N, P, Si or Ge, h is an integer from 1 to 2, such that the valence of $M^2$ is filled, and $R^{16}$ is hydrogen, hydrocarbyl, substituted hydrocarbyl or a functional group, preferably an arene, and each $R^{16}$ group may be the same or different, and any two $R^{16}$ groups may be linked together to form a ring, preferably, $R^{10}$ is $SiMe_2$, $Si(CH_2)_2$, $Si(CH_2)_3$, $SiPh_2$, $Si(biphenyl)_1$, $Si(biphenyl)_2$, $Si(o-tolyl)_2$, more preferably $R^{10}$ is $SiMe_2$ or $SiPh_2$;

each $R^{11}$ is independently selected from the group consisting of hydrogen, hydrocarbyl, substituted hydrocarbyl and a functional group, preferably $R^{11}$ is hydrogen, methyl, ethyl, propyl or phenyl, more preferably $R^{11}$ is hydrogen, and the $R^{11}$ groups may be the same or different, and the $R^{11}$ groups may be linked together to form a ring, and $R^{11}$ and $R^8$ may be linked together to form a ring;

c is an integer=0, 1, or 2;
d is an integer=0, 1, or 2;
e is an integer=0, 1, or 2;
The sum of c, d, and e is 1, 2 or 3, preferably the sum of c, d, and e is 1 or 2, more preferably, the sum of c, d, and e is 1;

preferably, provided that if the two $R^1$ groups are linked, then they do not form a butadiene group when M is Zr.

In an alternate embodiment, when M is Hf at least one $R^2$ group attached to a six carbon ring is not methyl, preferably at least two $R^2$ groups are not methyl, preferably at three $R^2$ groups are not methyl, preferably all four $R^2$ groups attached to a six carbon ring are not methyl.

In another preferred embodiment, M is Hf, and both $R^1$ groups are methyl.

In a preferred embodiment, the metallocene catalyst compounds used herein are represented by the Formula 3 below:

where:
M is a transition metal selected from group 4 of the periodic table, preferably Zr, Ti or Hf, preferably Zr or Hf, most preferably Hf;

each $R^1$ is independently selected from the group consisting of hydrogen, hydrocarbyl, substituted hydrocarbyl and a functional group, preferably $R^1$ is a hydrogen, a hydrocarbon or a halide, more preferably $R^1$ is a hydride, methyl, ethyl, trimethylsilylmethyl, trimethylsilyl, phenyl, naphthyl, allyl, or benzyl, even more preferably $R^1$ is methyl, and the two $R^1$ groups may be the same or different, and the two $R^1$ groups may be linked, provided that if the two $R^1$ groups are linked, then they do not form a butadiene group when M is Zr;

Me is methyl;

each $R^8$ is independently selected from the group consisting of hydrogen, hydrocarbyl, substituted hydrocarbyl and a functional group, preferably $R^8$ is hydrogen, methyl, ethyl or propyl, more preferably $R^8$ is hydrogen or methyl, and the $R^8$ groups may be the same or different; and each $R^{16}$ may be the same or different and the $R^{16}$ groups may be linked together to form a ring, preferably each $R^{16}$ is independently a methyl, ethyl, phenyl, biphenyl, o-tolyl, or an arene, preferably $R^{16}$ is methyl, ethyl, phenyl or an arene.

In any a preferred embodiment of any of the above formulae $R^8$ is not a phenyl group and or a substituted phenyl group.

In another preferred embodiment, if the two $R^1$ groups are linked, then they do not form a butadiene group when M is Ti.

In another preferred embodiment, if the two $R^1$ groups are linked, then they do not form a butadiene group when M is Hf.

In a preferred embodiment, the metallocene catalyst compounds used herein are represented by the following formulae:

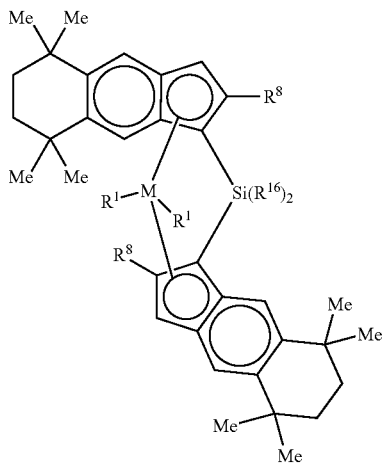

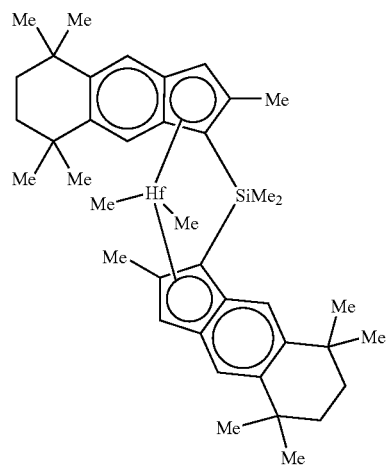

-continued

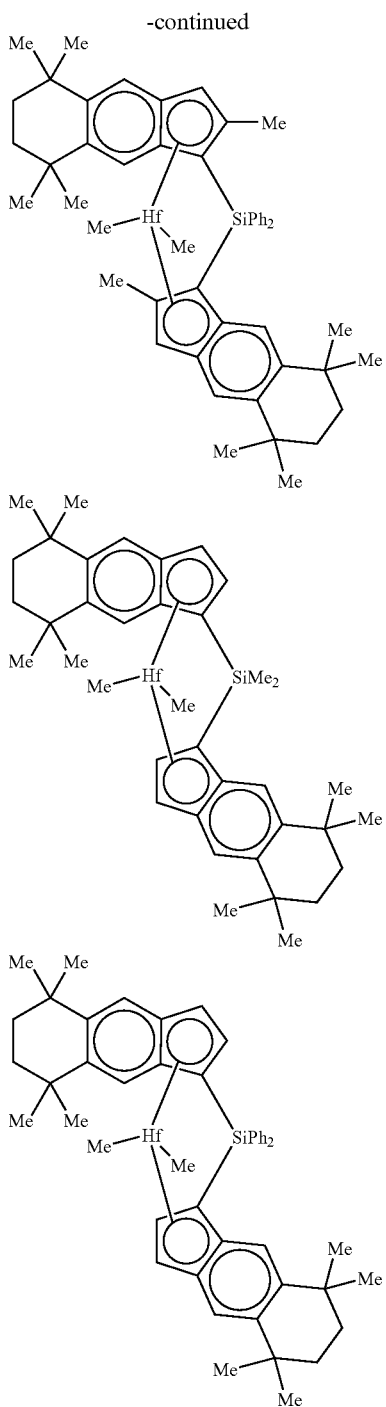

where Me is methyl, Hf is hafnium, Ph is phenyl, and Si is silicon. In another embodiment the Hf is replaced with zirconium. In another embodiment, the Hf is replaced with titanium.

In another embodiment, the metallocene catalysts compounds useful in this invention are present in a formal +4 oxidation state. In another embodiment, the catalyst compounds of this invention are not present in a formal +2 oxidation state. The nomenclature of formal oxidation states used here are described in length in the texts: Hegedus, L. S. Transition Metals in the Synthesis of Complex Organic Molecules 2nd Ed, University Science Press, 1999, Sausalito, Calif. and Collman, J. P. et. al. Principles and Applications of Organotransition Metal Chemistry. University Science Press, 1987, Sausalito, Calif.

In another preferred embodiment the metallocene catalyst compounds described herein may be used in combination with other polymerization and or oligomerization catalysts. In a preferred embodiment the instant catalyst compounds are used in combination with catalyst compounds described in any of the following references and references therein:

Hlatky, G. G. *Chem. Rev.* 2000, 100, 1347; Alt, H.; Koppl, A. *Chem. Rev.* 2000, 100, 1205; Resconi, L.; Cavallo, L.; Fait, A.; Piermontesi, F. *Chem. Rev.* 2000, 100, 1253; Bryntzinger, H. H.; et. al. Angew. Chem. Int. Ed. Engl. 1995, 34, 1143; Ittel, S. D.; Johnson, L. K.; Brookhart, M. *Chem. Rev.* 2000, 100, 1169; Gibson, V. C.; Spitzmesser, S. K. *Chem. Rev.* 2003, 103, 283. ; Skupinska, J. *Chem. Rev.* 1991, 91, 613; Carter, A. et. al. *Chem. Commun.* 2002, 858; McGuinness, D. S.; et. al. *J. Am. Chem. Soc.* 2003, 125, 5272; McGuiness, D. S. *Chem. Commun.* 2003, 334.

In another embodiment, non-metallocene catalyst compounds, such as bisamide catalyst compounds, may be used in combination with the metallocene catalyst compounds. Bisamide catalyst compounds are defined to be bidentate bisamide catalyst compounds, pyridine bisamide catalyst compounds, and amine bisamide catalyst compounds.

Bidentate bisamide catalyst compounds are those represented by the following formula:

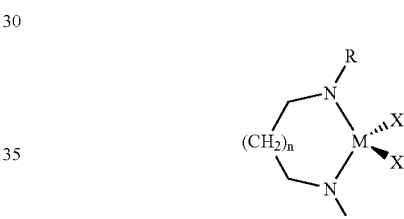

M is Ti, Zr, or Hf. R are the same or different alkyl, aryl, substituted alkyl, or substituted aryl radicals. X are the same or different alkyl, aryl, or halide radicals. Substituted alkyls and aryls can be alkyl-, aryl-, and halo-substituted. When X is a halide, the bisamide catalyst compound is typically first chemically modified to transform X into an abstractable ligand. This can be done by alkylation, for example.

Pyridine bisamide catalyst compounds are also useful herein. Pyridine bisamide catalyst compounds are those compounds that have the following formula:

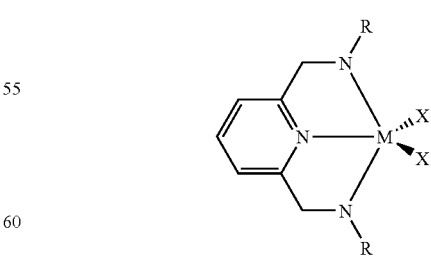

M is Ti, Zr, or Hf. R are the same or different alkyl, aryl, substituted alkyl, or substituted aryl radicals. X are the same or different alkyl, aryl, or halide radicals. Substituted alkyls and aryls can be alkyl-, aryl-, and halo-substituted. When X is a halide, the pyridine bisamide catalyst compound is typically first chemically modified to transform X into an abstractable ligand. This can be done by alkylation, for example.

Amine bisamide catalyst compounds are also useful herein. Amine bisamide catalyst compounds are those represented by the following formula:

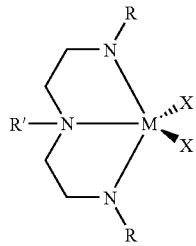

M is Ti, Zr, or Hf. R and R' are the same or different alkyl, aryl, substituted alkyl, or substituted aryl radicals. X are the same or different alkyl, aryl, or halide radicals. Substituted alkyl and aryls can be alkyl-, aryl-, and halo-substituted. When X is a halide, the amine bisamide catalyst compound must first be chemically modified to transform X into an abstractable ligand. This can be done by alkylation, for example.

Additional catalyst compounds that may be used in combination with the metallocene catalyst compounds described herein include bisimide catalyst compounds represented by the formula:

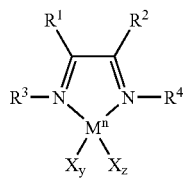

where M is a group 8,9,10, metal, preferably a group 10 metal, preferably Pd, Pt or Ni;
n is the oxidation state of M and may be 2, 3, or 4;
each X is independently a halogen or a substituted or unsubstituted hydrocarbyl group, a substituted or unsubstituted hydrocarboxy group, or a substituted or unsubstituted heteroatom containing group;
y is 0 or 1;
z is 0 or 1, where n=y+z+2;
$R^1$ is a heteroatom, a substituted $C_1$ to $C_{50}$ hydrocarbyl group or an unsubstituted $C_1$ to $C_{50}$ hydrocarbyl group;
$R^2$ is a heteroatom, a substituted $C_1$ to $C_{50}$ hydrocarbyl group or an unsubstituted $C_1$ to $C_{50}$ hydrocarbyl group;
$R^3$ is a heteroatom, a substituted $C_1$ to $C_{50}$ hydrocarbyl group or an unsubstituted $C_1$ to $C_{50}$ hydrocarbyl group, preferably a phenyl group;
$R^4$ is a heteroatom, a substituted $C_1$ to $C_{50}$ hydrocarbyl group or an unsubstituted $C_1$ to $C_{50}$ hydrocarbyl group, preferably a phenyl group,
where any adjacent R groups may form fused ring systems.

Exemplary compounds include those described in the patent literature. International patent publications WO 96/23010, WO 97/48735 and Gibson, et al., *Chem. Comm.*, pp. 849-850 (1998), which disclose diimine-based ligands for Group-8-10 compounds that undergo ionic activation and polymerize olefins. Polymerization catalyst systems from Group-5-10 metals, in which the active center is highly oxidized and stabilized by low-coordination-number, polyanionic, ligand systems, are described in U.S. Pat. No. 5,502,124 and its divisional U.S. Pat. No. 5,504,049. See also the Group-5 organometallic catalyst compounds of U.S. Pat. No. 5,851,945 and the tridentate-ligand-containing, Group-5-10, organometallic catalysts of U.S. Pat. No. 6,294,495. Group-11 catalyst precursor compounds, activatable with ionizing cocatalysts, useful for olefin and vinylic polar molecules are described in WO 99/30822.

U.S. Pat. No. 5,318,935 describes bridged and unbridged, bisamido catalyst compounds of Group-4 metals capable of α-olefins polymerization. Bridged bis(arylamido)Group-4 compounds for olefin polymerization are described by D. H. McConville, et al., in *Organometallics* 1995, 14, 5478-5480. This reference presents synthetic methods and compound characterizations. Further work appearing in D. H. McConville, et al, *Macromolecules* 1996, 29, 5241-5243, describes bridged bis(arylamido)Group-4 compounds that are polymerization catalysts for 1-hexene. Additional invention-suitable transition metal compounds include those described in WO 96/40805. Cationic Group-3- or Lanthanide-metal olefin polymerization complexes are disclosed in copending U.S. application Ser. No. 09/408,050, filed 29 Sep. 1999, now U.S. Pat. No. 6,403,773. A monoanionic bidentate ligand and two monoanionic ligands stabilize those catalyst compounds, which can be used herein.

The literature describes many additional suitable catalyst compound that can be used in this invention. See, for instance, V. C. Gibson, et al; "The Search for New-Generation Olefin Polymerization Catalysts: Life Beyond Metallocenes", *Angew. Chem. Int. Ed.*, 38, 428-447 (1999).

Mixtures

In a preferred embodiment the processes of this invention may be used with two or more catalyst compounds at the same time or in series. In particular two different catalyst compounds can be activated with the same or different activators and introduced into the polymerization system at the same or different times.

As mentioned above, invention process can employ mixtures of catalyst compounds to select the properties that are desired from the polymer. Mixed catalyst systems can be employed in invention processes to alter or select desired physical or molecular properties. For example, mixed catalyst systems can control the molecular weight distribution of isotactic polypropylene when used with the invention processes or for the invention polymers.

Mixed-catalyst systems can be used with the invention polymerization processes to tailor the composition distribution of copolymers with high catalyst productivity. These systems can also, optionally, be used with diene incorporation to facilitate long chain branching using mixed catalyst systems and high levels of vinyl terminated polymers.

In preferred embodiments two or more of the above catalysts compounds can be used together.

In another embodiment preferred catalyst combinations include any of the above catalysts (preferably dimethylsilyl bis (2,2,5,5-tetramethyl cyclohexyl indenyl) hafnium dimethyl), with one or more of dimethylsilyl bis(2-methyl, 5-phenyl-indenyl) zirconium dichloride, dimethylsilyl bis(2-methyl, 5-phenyl-indenyl) zirconium dibromide, dimethylsilyl bis(2-methyl, 5-phenyl-indenyl) zirconium dimethyl, dimethylsilyl bis (2-methyl, 5-phenyl-indenyl) Zr(N—R)$_2$ where R is methyl, ethyl, butyl or hexyl).

In another embodiment the catalyst compound is not dimethylmethenyl(fluorenyl)(cyclopentadienyl)zirconium dichloride [Me₂C(flu)(cp)ZrCl₂].

Activators and Activation Methods for Catalyst Compounds

The catalyst compounds described herein are combined with activators for use in the processes of this invention.

An activator is defined as any combination of reagents that increases the rate at which a metal complex polymerizes unsaturated monomers, such as olefins. An activator may also affect the molecular weight, degree of branching, comonomer content, or other properties of the polymer.

A. Alumoxane and Aluminum Alkyl Activators

In one embodiment, one or more alumoxanes are utilized as an activator in the processes of the invention. Alumoxanes, sometimes called aluminoxanes in the art, are generally oligomeric compounds containing —Al(R)—O— subunits, where R is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is a halide. Mixtures of different alumoxanes and modified alumoxanes may also be used. For further descriptions, see U.S. Pat. Nos. 4,665,208; 4,952,540; 5,041,584; 5,091,352; 5,206,199; 5,204,419; 4,874,734; 4,924,018; 4,908,463; 4,968,827; 5,329,032; 5,248,801; 5,235,081; 5,157,137; 5,103,031; and EP 0 561 476 A1, EP 0 279 586 B3, EP 0 516 476 A, EP 0 594 218 A1, and WO 94/10180.

When the activator is an alumoxane (modified or unmodified), some embodiments select the maximum amount of activator at a 5000-fold molar excess Al/M over the catalyst compound (per metal catalytic site). The minimum activator-to-catalyst-compound is typically a 1:1 molar ratio.

Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage. There are a variety of methods for preparing alumoxane and modified alumoxanes, non-limiting examples of which are described in U.S. Pat. Nos. 4,665,208; 4,952,540; 5,091,352; 5,206,199; 5,204,419; 4,874,734; 4,924,018; 4,908,463; 4,968,827; 5,308,815; 5,329,032; 5,248,801; 5,235,081; 5,157,137; 5,103,031; 5,391,793; 5,391,529; 5,693,838; 5,731,253; 5,731,451; 5,744,656; 5,847,177; 5,854,166; 5,856,256; and 5,939,346; and European publications EP-A-0 561 476, EP-B1-0 279 586, EP-A-0 594-218, and EP-B1-0 586 665, and PCT publications WO 94/10180 and WO 99/15534, all of which are fully incorporated herein by reference. It may be preferable to use a visually clear methylalumoxane. A cloudy or gelled alumoxane can be filtered to produce a clear solution or clear alumoxane can be decanted from the cloudy solution. Another preferred alumoxane is a modified methyl alumoxane (MMAO) cocatalyst type 3A (commercially available from Akzo Chemicals, Inc. under the trade name Modified Methylalumoxane type 3A, covered under patent number U.S. Pat. No. 5,041,584).

Aluminum alkyl or organoaluminum compounds which may be utilized as activators (or scavengers) include trimethylaluminum, triethylaluminum, triisobutylaluminum, tri-n-hexylaluminum, tri-n-octylaluminum and the like.

In another embodiment, the activator is not an alumoxane, preferably the activator is not methylalumoxane. Alternately the catalyst system used herein comprises less than 0.1 weight % of an alumoxane.

B. Ionizing Activators

It is within the scope of this invention to use an ionizing or stoichiometric activator, neutral or ionic, such as tri (n-butyl) ammonium tetrakis (pentafluorophenyl) boron, a trisperfluorophenyl boron metalloid precursor or a trisperfluoronaphtyl boron metalloid precursor, polyhalogenated heteroborane anions (WO 98/43983), boric acid (U.S. Pat. No. 5,942,459) or combination thereof as an activator in the processes of this invention. It is also within the scope of this invention to use neutral or ionic activators alone or in combination with alumoxane or modified alumoxane activators.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, napthyl or mixtures thereof. Even more preferably, the three groups are halogenated, preferably fluorinated, aryl groups. Most preferably, the neutral stoichiometric activator is trisperfluorophenyl boron or trisperfluoronapthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B:1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, now abandoned, all of which are fully incorporated herein by reference.

Preferred activators include a cation and an anion component, and may be represented by the following formula:

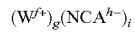

(W$^{f+}$)$_g$(NCA$^{h-}$)$_i$

W$^{f+}$ is a cation component having the charge f+,
NCA$^{h-}$ is a non-coordinating anion having the charge h–,
f is an integer from 1 to 3,
h is an integer from 1 to 3, and
g and h are constrained by the relationship: (g)×(f)=(h)×(i).

The cation component, (W$^{f+}$) may include Bronsted acids such as protons or protonated Lewis bases or reducible Lewis acids capable of protonating or abstracting a moiety, such as an alkyl or aryl, from an analogous metallocene or Group 15 containing transition metal catalyst compound, resulting in a cationic transition metal species.

In a preferred embodiment, the activators include a cation and an anion component, and may be represented by the following formula:

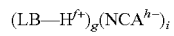

(LB—H$^{f+}$)$_g$(NCA$^{h-}$)$_i$ wherein LB is a neutral Lewis base;
H is hydrogen;
NCA$^{h-}$ is a non-coordinating anion having the charge h–,
f is an integer from 1 to 3,
h is an integer from 1 to 3, and
g and h are constrained by the relationship: (g)×(f)=(h)×(i)

The activating cation ($W^{d+}$) may be a Bronsted acid, (LB—$H^{d+}$), capable of donating a proton to the transition metal catalyst compound resulting in a transition metal cation, including ammoniums, oxoniums, phosphoniums, silyliums and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers such as dimethyl ether diethyl ether, tetrahydrofuran and dioxane, sulfoniums from thioethers, such as diethyl thioethers and tetrahydrothiophene and mixtures thereof.

The activating cation ($W^{d+}$) may also be an abstracting moiety such as silver, carboniums, tropylium, carbeniums, ferroceniums and mixtures, preferably carboniums and ferroceniums. Most preferably ($W^{d+}$) is triphenyl carbonium or N,N-dimethylanilinium.

The anion component ($NCA^{h-}$) includes those having the formula $[T^{j+}Q_k]^{h-}$ wherein j is an integer from 1 to 3; k is an integer from 2 to 6; k–j=h; T is an element selected from Group 13 or 15 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable ($NCA^{h-}$)$_i$ also include diboron compounds as disclosed in U.S. Pat. No. 5,447,895, which is fully incorporated herein by reference.

Additional suitable anions are known in the art and will be suitable for use with the catalysts of the invention. See in particular, U.S. Pat. No. 5,278,119 and the review articles by S. H. Strauss, "The Search for Larger and More Weakly Coordinating Anions", Chem. Rev., 93, 927-942 (1993) and C. A. Reed, "Carboranes: A New Class of Weakly Coordinating Anions for Strong Electrophiles, Oxidants and Superacids", Acc. Chem. Res., 31, 133-139 (1998).

Illustrative, but not limiting examples of boron compounds which may be used as an activating cocatalyst in the preparation of the improved catalysts of this invention are tri-substituted ammonium salts such as:
trimethylammonium tetraphenylborate,
triethylammonium tetraphenylborate,
tripropylammonium tetraphenylborate,
tri(n-butyl)ammonium tetraphenylborate,
tri(t-butyl)ammonium tetraphenylborate,
N,N-dimethylanilinium tetraphenylborate,
N,N-diethylanilinium tetraphenylborate,
N,N-dimethyl-(2,4,6-trimethylanilinium) tetraphenylborate,
trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl) borate,
N,N-dimethylanilinium tetrakis(pentafluorophenyl) borate,
N,N-diethylanilinium tetrakis(pentafluorophenyl) borate,
N,N-dimethyl-(2,4,6-trimethylanilinium) tetrakis(pentafluorophenyl) borate,
trimethylammonium tetrakis-(2,3,4,6-tetrafluorophenylborate,
triethylammonium tetrakis-(2,3,4,6-tetrafluorophenyl) borate,
tripropylammonium tetrakis-(2,3,4,6-tetrafluorophenyl) borate,
tri(n-butyl)ammonium tetrakis-(2,3,4,6-tetrafluoro-phenyl) borate,
dimethyl(t-butyl)ammonium tetrakis-(2,3,4,6-tetrafluorophenyl) borate,
N,N-dimethylanilinium tetrakis-(2,3,4,6-tetrafluorophenyl) borate,
N,N-diethylanilinium tetrakis-(2,3,4,6-tetrafluoro-phenyl) borate, and
N,N-dimethyl-(2,4,6-trimethylanilinium)tetrakis-(2,3,4,6-tetrafluorophenyl) borate;
dialkyl ammonium salts such as: di-(i-propyl)ammonium tetrakis(pentafluorophenyl) borate, and dicyclohexylammonium tetrakis(pentafluorophenyl) borate; and tri-substituted phosphonium salts such as:
triphenylphosphonium tetrakis(pentafluorophenyl) borate, tri(o-tolyl)phosphonium tetrakis(pentafluorophenyl) borate, and tri(2,6-dimethylphenyl)phosphonium tetrakis (pentafluorophenyl) borate.

Most preferably, the ionic stoichiometric activator is N,N-dimethylanilinium tetra(perfluorophenyl)borate and/or triphenylcarbenium tetra(perfluorophenyl)borate.

In one embodiment, an activation method using ionizing ionic compounds not containing an active proton but capable of producing an analogous metallocene catalyst cation and their non-coordinating anion are also contemplated, and are described in EP-A-0 426 637, EP-A-0 573 403 and U.S. Pat. No. 5,387,568, which are all fully incorporated herein by reference.

The term "non-coordinating anion" (NCA) means an anion which either does not coordinate to said cation or which is only weakly coordinated to said cation thereby remaining sufficiently labile to be displaced by a neutral Lewis base. "Compatible" non-coordinating anions are those which are not degraded to neutrality when the initially formed complex decomposes. Non-coordinating anions useful in accordance with this invention are those that are compatible, stabilize the metal cation in the sense of balancing its ionic charge, yet retain sufficient ability to permit displacement by an ethylenically or acetylenically unsaturated monomer during polymerization. These types of cocatalysts sometimes use tri-isobutyl aluminum or tri-octyl aluminum as a scavenger.

Invention process also can employ cocatalyst compounds or activator compounds that are initially neutral Lewis acids but form a cationic metal complex and a noncoordinating anion, or a zwitterionic complex upon reaction with the invention compounds. For example, tris(pentafluorophenyl) boron or aluminum act to abstract a hydrocarbyl or hydride ligand to yield an invention cationic metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878; 5,486,632; and 5,527,929.

Additional neutral Lewis-acids are known in the art and are suitable for abstracting formal anionic ligands. See in particular the review article by E. Y.-X. Chen and T. J. Marks, "Cocatalysts for Metal-Catalyzed Olefin Polymerization: Activators, Activation Processes, and Structure-Activity Relationships", Chem. Rev., 100, 1391-1434 (2000).

When the catalyst compound does not contain at least one hydride or hydrocarbyl ligand but does contain at least one functional group ligand, such as chloride, amido or alkoxy ligands, and the functional group ligands are not capable of discrete ionizing abstraction with the ionizing, anion precursor compounds, these functional group ligands can be converted via known alkylation reactions with organometallic compounds such as lithium or aluminum hydrides or alkyls, alkylalumoxanes, Grignard reagents, etc. See EP-A-0 500 944, EP-A1-0 570 982 and EP-A1-0 612 768 for analogous processes describing the reaction of alkyl aluminum compounds with analogous dihalide substituted metallocene compounds prior to or with the addition of activating noncoordinating anion precursor compounds.

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-compound-to-activator molar ratio may be any ratio. Combinations of the described activator compounds may also be used for activation. For example, tris(perfluorophenyl) boron can be used with methylalumoxane.

C. Non-ionic Activators

Activators are typically strong Lewis-acids which may play either the role of ionizing or non-ionizing activator. Activators previously described as ionizing activators may also be used as non-ionizing activators.

Abstraction of formal neutral ligands may be achieved with Lewis acids that display an affinity for the formal neutral ligands. These Lewis acids are typically unsaturated or weakly coordinated. Examples of non-ionic activators include $R^{10}(R^{11})_3$, where $R^{10}$ is a group 13 element and $R^{11}$ is a hydrogen, a hydrocarbyl, a substituted hydrocarbyl, or a functional group. Typically, $R^{11}$ is an arene or a perfluorinated arene. Non-ionic activators also include weakly coordinated transition metal compounds such as low valent olefin complexes.

Non-limiting examples of non-ionic activators include $BMe_3$, $BEt_3$, $B(iBu)_3$, $BPh_3$, $B(C_6F_5)_3$, $AlMe_3$, $AlEt_3$, $Al(iBu)_3$, $AlPh_3$, $B(C_{10}F_7)_3$, $[NMeHPh][B(C_{10}F_7)_4]$, alumoxane, CuCl, $Ni(1,5\text{-cyclooctadiene})_2$.

Additional neutral Lewis-acids are known in the art and will be suitable for abstracting formal neutral ligands. See in particular the review article by E. Y.-X. Chen and T. J. Marks, "Cocatalysts for Metal-Catalyzed Olefin Polymerization: Activators, Activation Processes, and Structure-Activity Relationships", *Chem. Rev.*, 100, 1391-1434 (2000).

Preferred non-ionic activators include $R^{10}(R^{11})_3$, where $R^{10}$ is a group 13 element and $R^{11}$ is a hydrogen, a hydrocarbyl, a substituted hydrocarbyl, or a functional group. Typically, $R^{11}$ is an arene or a perfluorinated arene.

More preferred non-ionic activators include $B(R^{12})_3$, where $R^{12}$ is a an arene or a perfluorinated arene. Even more preferred non-ionic activators include $B(C_{10}F_7)_3$ and $B(C_6F_5)_3$. A particularly preferred non-ionic activator is $B(C_6F_5)_3$. More preferred ionic and non-ionic activators are based on perfluoroaryl borane and perfluoroaryl borates such as $PhNMe_2H^+B(C_6F_5)_4^-$, $(C_6H_5)_3C^+B(C_6F_5)_4^-$; and $B(C_6F_5)_3$.

Additional preferred activators that may be used with the catalysts compounds disclosed herein include those described in WO 03/064433A1, which is fully incorporated herein by reference.

In general the catalyst compound(s) and the activator are combined in ratios of about 1000:1 to about 0.5:1. In a preferred embodiment the catalyst compounds and the activator are combined in a ratio of about 300:1 to about 1:1, preferably about 150:1 to about 1:1, for boranes, borates, aluminates, etc. the ratio is preferably about 1:1 to about 10:1 and for alkyl aluminum compounds (such as diethylaluminum chloride combined with water) the ratio is preferably about 0.5:1 to about 10:1.

In a preferred embodiment the ratio of the first catalyst to the second or additional catalyst is 5:95 to 95:5, preferably 25:75 to 75:25, even more preferably 40:60 to 60:40.

In general the combined catalyst compounds and the activator are combined in ratios of about 1:10,000 to about 1:1, in other embodiments the combined catalyst compounds and the activator are combined in ratios of 1:1 to 100:1. When alumoxane or aluminum alkyl activators are used, the combined catalyst compound-to-activator molar ratio is from 1:5000 to 10:1, alternatively from 1:1000 to 10:1; alternatively, 1:500 to 2:1; or 1:300 to 1:1. When ionizing activators are used, the combined catalyst compound-to-activator molar ratio is from 10:1 to 1:10; 5:1 to 1:5; 2:1 to 1:2; or 1.2:1 to 1:1. Multiple activators may be used, including using mixtures of alumoxanes or aluminum alkyls with ionizing activators.

Supports

In another embodiment the catalyst compositions of this invention include a support material or carrier. For example, the one or more catalyst components and/or one or more activators may be deposited on, contacted with, vaporized with, bonded to, or incorporated within, adsorbed or absorbed in, or on, one or more supports or carriers.

The support material is any of the conventional support materials. Preferably the supported material is a porous support material, for example, talc, inorganic oxides and inorganic chlorides. Other support materials include resinous support materials such as polystyrene, functionalized or crosslinked organic supports, such as polystyrene divinyl benzene polyolefins or polymeric compounds, zeolites, clays, or any other organic or inorganic support material and the like, or mixtures thereof.

The preferred support materials are inorganic oxides that include those Group 2, 3, 4, 5, 13 or 14 metal oxides. The preferred supports include silica, which may or may not be dehydrated, fumed silica, alumina (WO 99/60033), silica-alumina and mixtures thereof. Other useful supports include magnesia, titania, zirconia, magnesium chloride (U.S. Pat. No. 5,965,477), montmorillonite (European Patent EP-B1 0 511 665), phyllosilicate, zeolites, talc, clays (U.S. Pat. No. 6,034,187) and the like. Also, combinations of these support materials may be used, for example, silica-chromium, silica-alumina, silica-titania and the like. Additional support materials may include those porous acrylic polymers described in EP 0 767 184 B1, which is fully incorporated herein by reference. Other support materials include nanocomposites as described in PCT WO 99/47598, aerogels as described in WO 99/48605, spherulites as described in U.S. Pat. No. 5,972,510 and polymeric beads as described in WO 99/50311, which are all fully incorporated herein by reference.

It is preferred that the support material, most preferably an inorganic oxide, has a surface area in the range of from about 10 to about 700 $m^2/g$, pore volume in the range of from about 0 to about 4.0 cc/g and average particle size in the range of from about 0.02 to about 50 μm. More preferably, the surface area of the support material is in the range of from about 50 to about 500 m²/g, pore volume of from about 0 to about 3.5 cc/g and average particle size of from about 0.02 to about 20 μm. Most preferably the surface area of the support material is in the range is from about 100 to about 400 m²/g, pore volume from about 0 to about 3.0 cc/g and average particle size is from about 0.02 to about 10 μm.

Non-porous supports may also be used as supports in the processes described herein. For example, in a preferred embodiment the nonporous, fumed silica supports described in U.S. Pat. No. 6,590,055 can be used in the practice of this invention.

Additional useful activators for use in the processes of this invention include clays that have been treated with acids (such as $H_2SO_4$) and then combined with metal alkyls (such as triethylaluminum) as described in U.S. Pat. No. 6,531,552 and EP 1 160 261 A1, which is fully incorporated herein by reference.

Preferred activators include that may also be supports include ion-exchange layered silicate having an acid site of at most −8.2 pKa, the amount of the acid site is equivalent to at least 0.05 mmol/g of 2,6-dimethylpyridine consumed for neutralization. Preferred examples include chemically treated smectite group silicates, acid-treated smectite group silicates. Additional preferred examples of the ion-exchange layered silicate useful in this invention include layered silicates having a 1:1 type structure or a 2:1 type structure as described in "Clay Minerals (Nendo Kobutsu Gaku)" written by Haruo Shiramizu (published by Asakura Shoten in 1995).

Examples of an ion-exchanged layered silicate comprising the 1:1 layer as the main constituting layer include kaolin group silicates such as dickite, nacrite, kaolinite, metahalloysite, halloysite or the like, and serpentine group silicates such as chrysotile, lizaldite, antigorite or the like. Additional preferred examples of the ion-exchanged layered silicate useful in this invention include ion-exchanged layered silicates comprising the 2:2 layer as the main constituting layer include smectite group silicates such as montmorillonite, beidellite, nontronite, saponite, hectorite, stephensite or the like, vermiculite group silicates such as vermiculite or the like, mica group silicates such as mica, illite, sericite, glauconite or the like, and attapulgite, sepiolite, palygorskite, bentonite, pyrophyllite, talc, chlorites and the like. The clays are contacted with an acid, a salt, an alkali, an oxidizing agent, a reducing agent or a treating agent containing a compound intercalatable between layers of an ion-exchange layered silicate. The intercalation means to introduce other material between layers of a layered material, and the material to be introduced is called as a guest compound. Among these treatments, acid treatment or salt treatment is particularly preferable. The treated clay may then be contacted with an activator compound, such as TEAL, and the catalyst compound to polymerize olefins.

In another embodiment the polymerization system comprises less than 5 weight % polar species, preferably less than 4 weight %, more preferably less than 3 weight %, more preferably less than 2 weight %, more preferably less than 1 weight %, more preferably less than 1000 ppm, more preferably less than 750 ppm, more preferably less than 500 ppm, more preferably less than 250 ppm, more preferably less than 100 ppm, more preferably less than 50 ppm, more preferably less than 10 ppm. Polar species include oxygen containing compounds (except for alumoxanes) such as alcohols, oxygen, ketones, aldehydes, acids, esters and ethers.

In another embodiment the polymerization system comprises less than 5 weight % trimethylaluminum and/or triethylaluminum, preferably less than 4 weight %, more preferably less than 3 weight %, more preferably less than 2 weight %, more preferably less than 1 weight %, more preferably less than 1000 ppm, more preferably less than 750 ppm, more preferably less than 500 ppm, more preferably less than 250 ppm, more preferably less than 100 ppm, more preferably less than 50 ppm, more preferably less than 10 ppm.

In another preferred embodiment the polymerization system comprises methylalumoxane and less than 5 weight % trimethylaluminum and or triethylaluminum, preferably less than 4 weight %, more preferably less than 3 weight %, more preferably less than 2 weight %, more preferably less than 1 weight %, more preferably less than 1000 ppm, more preferably less than 750 ppm, more preferably less than 500 ppm, more preferably less than 250 ppm, more preferably less than 100 ppm, more preferably less than 50 ppm, more preferably less than 10 ppm.

Preferred invention processes can use finely divided, supported catalysts to prepare propylene/1-hexene copolymers with greater than 1.0 mole % hex-1-ene. In addition to finely divided supports, invention processes can use fumed silica supports in which the support particle diameter can range from 200 angstroms to 1500 angstroms, small enough to form a colloid with reaction media.

Polymerization Process

This invention relates to processes to polymerize olefins comprising contacting one or more olefins having at least three carbon atoms with a catalyst compound and an activator at in a supercritical polymerization medium in a reactor. One or more reactors in series or in parallel may be used in the present invention. Catalyst compound and activator may be delivered as a solution or slurry, either separately to the reactor, activated in-line just prior to the reactor, or preactivated and pumped as an activated solution or slurry to the reactor. A preferred operation is two solutions activated in-line. Polymerizations are carried out in either single reactor operation, in which monomer, comonomers, catalyst/activator, scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors.

Invention methods also cover polymerization of propylene in high-pressure reactors where, preferably, the reactor is substantially unreactive with the polymerization reaction components and is able to withstand the high pressures and temperatures that occur during the polymerization reaction. Such reactors are known as high-pressure reactors for purposes of this disclosure. Withstanding these high pressures and temperatures will allow the reactor to maintain the propylene under supercritical conditions. Suitable reaction vessels include those known in the art to maintain supercritical or other high-pressure ethylene polymerization reactions. Suitable reactors are selected from autoclave, tubular, and autoclave/tubular reactors, among others.

The polymerization processes described herein operate well in autoclave and tubular reactors. Typically, autoclave reactors have length-to-diameter ratios of 1:1 to 20:1 and are fitted with a high-speed (up to 1500 RPM) multiblade stirrer. Autoclave pressures are typically greater than 6 MPa with a maximum of typically less than 260 MPa. Preferred autoclave reactors are fitted with external and/or internal cooling and one or more injection points along the reaction zone. When the autoclave has a low length-to-diameter ratio (such as less than 4) propylene and other monomers are typically injected at only one position. But injection at two or more positions in the autoclave is also possible. For instance, in reactors where the length-to-diameter ratio is around 4-20, the reactor can contain up to six different injection positions. Additionally, in the larger autoclaves, one or more lateral fixing devices support the high-speed stirrer. These fixing devices can also divide the autoclave into two or more zones. Mixing blades on the stirrer can differ from zone to zone to allow for plug flow or back mixing, largely independently, in the separate zones. Two or more autoclaves with one or more zones can connect in series to tailor polymer structure.

Tubular reactors are also well suited for use in this invention, preferably tubular reactors capable of operating up to about 350 MPa. Preferred tubular reactors are fitted with external and/or internal cooling and one or more injection points along the (tubular) reaction zone. As in autoclaves, these injection points serve as entry points for monomers (such as propylene), one or more comonomer, catalyst, or mixtures of these. In tubular reactors, external cooling allows for increased monomer conversion relative to an autoclave, where the low surface-to-volume ratio hinders any significant heat removal. Tubular reactors have a special outlet valve that can send a pressure shockwave backward along the tube. The shockwave helps dislodge any polymer residue that has formed on reactor walls during operation. Another way of addressing wall deposits is to fabricate the tube with smooth internal surfaces. Preferred tubular reactors can operate at pressures up to 360 MPa and preferably have lengths of 100-2000 meters and internal diameters usually less than 10 cm. Preferred tubular reactors typically have a length-to-diameter ratios of 1:1 to 500:1, preferably 1:1 to 20:1, preferably 4:4 to 20:1.

Reactor trains that pair autoclaves with tubular reactors can also serve in invention processes. In such instances, the autoclave typically precedes the tubular reactor. Such systems may have injection of additional catalyst and/or feed components at several points in the autoclave and more particularly along the tube length.

In both autoclaves and tubular reactors, at injection, feeds are preferably room temperature or below to provide maximum polymer production within the limits of maximum operating temperature. In autoclave operation, a preheater operates at startup, but not after the reaction reaches steady state if the first mixing zone has some back-mixing characteristics. In tubular reactors, the first section of double-jacketed tubing is heated rather than cooled and is operated continuously since a tubular reactor is by nature plug flow. In both multizone autoclaves and tubular reactors, catalyst can not only be injected at the inlet, but also optionally at one or more points along the reactor. The catalyst feeds injected at the inlet and other injection points can be the same or different in terms of content, density, concentration, etc. Choosing different catalyst feeds allows polymer design tailoring. At the reactor outlet valve, the pressure drops to levels below that which critical phase separation occurs. Therefore, the downstream vessel contains a polymer-rich phase and a polymer-lean phase. Typically, conditions in this vessel remain supercritical and temperature remains above the polymer product's crystallization temperature. The autoclave or tubular reactor effluent is depressurized on entering the high pressure separator (HPS). In polymerizations based on propylene alternative choices are open to the design relative to classic high pressure polyethylene process technology.

At the reactor outlet valve the pressure drops to begin the separation of polymer and unreacted monomer, co-monomers, propane, etc. The temperature in this vessel optionally can be maintained above the polymer product's crystallization point but the pressure may be below the critical point. The pressure need only be high enough that the propylene can be condensed against standard cooling water. The liquid recycle stream can then be recycled to the reactor with a liquid pumping system instead of the hyper-compressors required for polyethylene units. The relatively low pressure in this separator will reduce the monomer concentration in the liquid polymer phase which will result in a much lower polymerization rate. This polymerization rate may be low enough to operate this system without adding a catalyst poison or "killer". If a catalyst killer is required (e.g., to prevent reactions in the high pressure recycle) then provision must be made to remove any potential catalyst poisons from the recycled propylene rich monomer stream e.g. by the use of fixed bed adsorbents or by scavenging with an aluminum alkyl.

Alternatively, the HPS may be operated over propylene's critical pressure but within the propylene/polypropylene two phase region. This is the economically preferred method if polypropylene is to be produced with a revamped HPPE plant. The recycled HPS overhead is cooled and dewaxed before being returned to the suction of the secondary compressor, which is typical of HPPE plant operation.

The polymer from this intermediate or high pressure vessel will then go through another pressure reduction step to a low pressure separator. The temperature of this vessel will be maintained above the polymer melting point so that the polymer from this vessel can be fed as a liquid directly to an extruder or static mixer. The pressure in this vessel will be kept low by using a compressor to recover the unreacted monomers, etc to the condenser and pumping system referenced above. In an alternate embodiment, one may carry out the pressure drop in one step, instead of two, if operating pressure is low enough.

In addition to autoclave reactors, tubular reactors, or reactors combining these, loop-type reactors function as well. In this reactor type, monomer enters and polymer exits continuously at different points along the loop, while an in-line pump continuously circulates the contents (reaction liquid). The feed/product takeoff rates control total average residence time. A cooling jacket removes reaction heat from the loop. Industrially a loop reactor is typically not operated at the high pressures encountered in autoclaves and tubes.

Commercial low pressure loop reactors have diameters of 16 to 24 inches (41 to 61 cm) and lengths of 100 to 200+ meters. Operation in a single supercritical polypropylene in propylene solution phase is preferably at pressures of greater than 25 to 30 MPa. At these pressures smaller diameter thicker wall loop tubing is necessary resulting in potential difficulties in pump around efficiency and maximum allowable reactor capacity.

In addition to autoclave reactors, tubular reactors, or a combination of these reactors, loop-type reactors are useful in this invention. In this reactor type, monomer enters and polymer exits continuously at different points along the loop, while an in-line pump continuously circulates the contents (reaction liquid). The feed/product takeoff rates control total average residence time. A cooling jacket removes reaction heat from the loop. U.S. Pat. No. 6,355,741 discusses a reactor with at least two loops that is useful in the practice of this invention provided that one or both operate at the supercritical conditions. U.S. Pat. No. 5,326,835 describes a process said to produce polymer in a bimodal fashion. This process's first reactor stage is a loop reactor in which polymerization occurs in an inert, low-boiling hydrocarbon. After the loop reactor, the reaction medium transits into a gas-phase reactor where gas-phase polymerization occurs. Since two very different environments create the polymer, it shows a bimodal molecular weight distribution. This two-stage procedure can be modified to work with the procedure of the instant application. For instance, a first stage loop reactor can use propylene as the monomer and a propylene-based reaction medium as the inert low-boiling hydrocarbon. In another embodiment, the reactor can be fitted wit internal cooling coils.

PCT publication WO 19/14766 describes a process comprising the steps of (a) continuously feeding olefinic monomer and a catalyst system, with a metallocene component and a codatalyst component, to the reactor; (b) continuously polymerizing that monomer in a polymerization zone reactor under elevated pressure; (c) continuously removing the polymer/monomer mixture from the reactor; (d) continuously separating monomer from molten polymer; (e) reducing pressure to form a monomer-rich and a polymer-rich phase; and (f) separating monomer from the reactor. The polymerization zoning technique described in the above process can be practiced using the instant invention's process conditions. That is, the above process is suitable for use with this invention provided at least one polymerization zone makes the propylene or the reaction media containing propylene supercritical.

In general, feed inlet temperatures are generally at or below room temperature to provide cooling to the exothermic reaction in the reactor operating above the crystallization temperature of the polymer product. For a predominantly propylene containing feed with a catalyst producing significant polymer isotacticity the reactor temperature will be above 145° C.

The processes described herein may have residence times as short as 0.5 seconds and as long as four hours. In preferred embodiments the residence times are from 1 second to 30 minutes, preferably 5 seconds to 10 minutes, more preferably from 10 seconds to 7 minutes, more preferably from 10 seconds to 5 minutes. In some embodiments the residence time can be selected from 10, 30, 45, 50, 60, 120, and 150 seconds. Maximum residence times can be selected from 200, 300, 400, 500, or 600 seconds. In general, invention processes choose residence times of from 30-600 seconds; more particularly 45-400 or 60-300 seconds. In general, invention processes choose residence times of from 30 sec to 1 hour; more particularly 30 sec to 30 minutes; 45-400, or 60-300 sec. In another embodiment the polymerization of propylene the residence times are up to 5 minutes.

In some embodiments, invention processes produce polymer at a rate of 560 kg PP/kg catalyst per hr-10,000 kg PP/g catalyst/hr. More particularly, production rates can range from 560-2000 kg PP/g catalyst/hr or 600-1500 kg PP/g catalyst/hr.

Dividing the total quantity of polymer that is collected during the reaction time by the amount of propylene added to the reaction yields the conversion rate. The monomer-to-polymer conversion rate for the described processes is high. Invention processes can be run at conversion rates of 60 or less, 10-60, 20-60, 30-60, 40-60, 10-50, 20-50, 30-50, 40-50, 10-40, 20-40, or 30-40 percent conversion, preferably greater than 10, or greater than 20 percent conversion.

Catalyst productivities typically range from 828 to 5940 kg polymer/g catalyst/hr. These high levels of catalyst productivity may result in low residual solids in the polymer product. Residual solid amount of less than 0.5 wt %, particularly less than 0.3 wt %, or more particularly less than 0.1 wt % total solids residue are preferred.

Comonomers, Dual Catalysts and Polymer Structure

In reactors with multiple injection points for catalyst and feed there exists the possibility to tailor the polymer design. Use of more than one catalyst having different molecular weight and structural capabilities allows a wide variety of product compositions (e.g. bimodal, linear mixed with long chain branched).

The various olefins will have differing reactivity ratios for a given catalyst so a plug flow type operation will allow compositional tapering if for instance no feeds are injected down the reactor or compensation of the tapering if the more reactive monomer is injected preferentially along the tube. A single zone ideal back mixed autoclave reactor will not allow tapering of polymer composition but the use of multiple catalysts is still applicable. Operation of two such autoclaves in series or parallel can allow the use of tailoring by altering the composition of fresh feed to the second reactor.

Catalyst Killing

The reactor effluent is depressurized to an intermediate pressure significantly below the cloud point pressure but nevertheless supercritical for that composition. This allows separation of a polymer rich phase for further purification and a propylene rich phase for recycle compression back to the reactor.

This separation is carried out in a vessel known as a high pressure separator (HPS). Since this vessel also has a significant residence time, the catalyst activity is killed by addition of a polar species such as water, alcohol or sodium/calcium stearate. The choice and quantity of killing agent will depend on the requirements for clean up of the recycle propylene and comonomers as well as the product properties, if the killing agent has low volatility.

Alternatively the intermediate separation can be done at pressures well below the critical point so that the monomer concentration and therefore reactivity in the high pressure separator is relatively low. The relatively small amount of continued polymerization in this vessel may not be a problem so addition of catalyst deactivating compounds as is done in PE processes may be avoided presuming that no undesired reactions occur in the high or intermediate pressure recycle system. If no killing compounds are added then the killer removal step can be eliminated.

Choice of Propylene Feed Purity

Propylene is available commercially at two levels of purity—polymer grade at 99.5 wt. % and chemical grade at about 93 to 95 wt. %. The choice of feed will set the level of purge required from the recycle to avoid over dilution of the feed by inert propane. The presence of propane in the reactor and HPS will raise the pressure of the cloud point curve for a given temperature but will decrease the polymerization efficiency due to a decrease in propylene (and other olefin) concentrations in the reactor. The elevation of cloud point pressure due to propane will widen the operating window of the HPS. In copolymerizations of propylene with limited amounts of ethylene, a similar effect in raising the cloud point pressure will be noted due to the presence of low levels of ethylene in the HPS.

Low Pressure Separator Operation

The LPS running at just above atmospheric pressure is just a simple sub critical flash of light components, reactants and oligomers thereof, for the sole purpose of producing a low volatile containing polymer melt entering the finishing extruder or static mixer.

Polymer Products

This invention also relates to a propylene polymer having excellent molecular weight while obtaining a lower melting heat.

The polymers produced by invention processes may be in any structures including block, linear, radial, star, branched, and combinations of these.

Some invention embodiments produce polypropylene and copolymers of polypropylene with a unique microstructure. The process of the invention can be practiced such that novel isotactic and syndiotactic compositions are made. In other embodiments, the invention processes make crystalline polymers.

The processes of the invention produce propylene polymers with a melting point of 60 to 150° C., and a weight-average molecular weight of 2,000 to 1,000,000, 10,000 to 1,000,000, 40,000 to 300,000, 50,000 to 250,000 or 70,000 to 200,000.

Invention processes produce polymer with a heat of fusion, $\Delta H_f$, of 1-70 J/g, 5-65 J/g, or 10-60 J/g. In another embodiment, the processes of this invention produce polymers having a $\Delta H_f$ of up to 80 J/g, preferably 10 to 70 J/g, more preferably 20 to 60 J/g.

The processes described herein can produce polymers having little or no ash or residue from catalyst or supports. In a preferred embodiment the polymers produced herein comprise less than 1 weight % silica, preferably less than 0.1 weight % silica, preferably less than 100 ppm silica, preferably less than 10 ppm.

Dienes can be used as a comonomer to increase the molecular weight of the resulting polymer and to create long chain branching. Vinyl chloride can be used as a comonomer to increase the degree of vinyl termination in the polymer.

Invention processes can produce long-chain-branched polypropylene. Long-chain branching is achievable using invention process regardless of whether additional $\alpha,\omega$-diene or other diene such as vinylnorbornene are used. In a preferred embodiment, less than 0.5 wt % diene is used. Alternatively, embodiments with less than 0.4 wt %, 0.3 wt %, 0.2 wt %, 1000 ppm, 500 ppm, 200 ppm, or 100 ppm.

In some embodiments, the present invention involves using as a comonomer an $\alpha,\omega$-diene and the olefin/$\alpha,\omega$-diene copolymers resulting from that use. Additionally, the present invention involves a copolymerization reaction of olefin monomers, wherein the reaction includes propylene and ethylene copolymerization with an $\alpha,\omega$-diene and the copolymers that are made. These copolymers may be employed in a variety of articles including, for example, films, fibers, such as spunbonded and melt blown fibers, fabrics, such as nonwoven fabrics, and molded articles. More particularly, these articles include, for example, cast films, oriented films, injection molded articles, blow-molded articles, foamed articles, foam laminates and thermoformed articles.

It should be noted that while linear $\alpha,\omega$-dienes are preferred, other dienes can also be employed to make polymers of this invention. These would include branched, substituted $\alpha,\omega$-dienes, such as 2-methyl-1,9-decadiene; cyclic dienes, such as vinylnorbornene or ethylidenenorbornene; or aromatic types, such as divinyl benzene.

Embodiments of the present invention include copolymers having from 98 to 99.999 weight percent olefin units, and from 0.001 to 2.000 weight percent $\alpha,\omega$-diene units. Copolymer embodiments may have a weight-average molecular weight from 50,000 to 2,000,000, crystallization temperatures from 50° C. to 140° C. and a melt flow rate (MFR) from 0.1 dg/min to 1500 dg/min. Note that the these embodiments display high crystallization temperatures intrinsically; there is no need for externally added nucleating agents.

In other embodiments, the copolymer includes from 90 to 99.999 weight percent of propylene units, from 0.000 to 8 weight percent of olefin units other than propylene units and from 0.001 to 2 weight percent $\alpha,\omega$-diene units. Copolymer embodiments may have weight-average molecular weights from 20,000 to 2,000,000, crystallization temperatures (without the addition of external nucleating agents) from 80° C. to 135° C. and MFRs from 0.1 dg/min to 1500 dg/min. The accompanying olefin may be any of $C_2$-$C_{20}$ $\alpha$-olefins, diolefins (with one internal olefin) and their mixtures thereof. More specifically, olefins include ethylene, butene-1, pentene-1, hexene-1, heptene-1,4-methyl-1-pentene, 3-methyl-1-pentene, 4-methyl-1-hexene, 5-methyl-1-hexene, 1-octene, 1-decene, 1-undecene, and 1-dodecene.

Copolymers of isotactic polypropylene made under supercritical conditions include ethylene and $C_4$-$C_{12}$ comonomers such as but-1-ene, 3-methylpent-1-ene, hex-1-ene, 4-methylpent-1-ene, and oct-1-ene. Invention process can prepare these copolymers without the use of solvent or in an environment with low solvent concentration.

In a preferred embodiment the polymers have a residual solid amount of less than 0.5 wt %, particularly less than 0.3 wt %, or more particularly less than 0.1 wt % total solids residue are preferred.

Preferred propylene polymers produced typically comprise 0 to 50 weight % of a comonomer, preferably 1 to 40 weight %, preferably 2 to 30 weight %, preferably 3 to 20 weight %, preferably 4 to 15 weight %, preferably 5 to 10 weight %, and have one or more of:

1. a heat of fusion of 60 J/g or less, preferably 50 J/g or less, preferably 40 or less, 30 J/g or less, more preferably 20 J/g or less;
2. a weight average molecular weight (as measured by GPC DRI) of 20,000 or more, preferably 50,000 to 2,000,000, preferably 100,000 to 1,000,000, preferably 150,000 to 900,000, preferably 200,000 to 800,000;
3. a melt flow rate of 0.5 dg/min or more, preferably 0.7 dg/min or more, preferably 1.0 dg/min or more, preferably between 0.1 and 1500 dg/min;
4. a melting temperature of 60° C. or more, preferably 70° C. or more, preferably 80° C. or more, preferably between 90 and 150° C., more preferably between 100 and 150° C.;
5. an Mw/Mn (as measured by GPC DRI) of about 1 to 20, preferably about 1.5 to 8, preferably 2 to 4.

In another embodiment the polymers produced herein have a melt viscosity of less than 10,000 centipoises at 180° C. as measured on a Brookfield viscometer, preferably between 300 to 3000 cPs for some embodiments (such as packaging and adhesives) and preferably between 5000 and 10,000 for other applications.

Formulations

In some embodiments the polymer produced by this invention may be blended with one or more other polymers, including but not limited to, thermoplastic polymer(s) and/or elastomer(s).

A "thermoplastic polymer(s)" is a polymer that can be melted by heat and then cooled with out appreciable change in properties. Thermoplastic polymers typically include, but are not limited to, polyolefins, polyamides, polyesters, polycarbonates, polysulfones, polyacetals, polylactones, acrylonitrile-butadiene-styrene resins, polyphenylene oxide, polyphenylene sulfide, styrene-acrylonitrile resins, styrene maleic anhydride, polyimides, aromatic polyketones, or mixtures of two or more of the above. Preferred polyolefins include, but are not limited to, polymers comprising one or more linear, branched or cyclic $C_2$ to $C_{40}$ olefins, preferably polymers comprising propylene copolymerized with one or more $C_2$ or $C_4$ to $C_{40}$ olefins, preferably a $C_3$ to $C_{20}$ alpha olefin, more preferably $C_3$ to $C_{10}$ α-olefins. More preferred polyolefins include, but are not limited to, polymers comprising ethylene copolymerized with a $C_3$ to $C_{40}$ olefin, preferably a $C_3$ to $C_{20}$ alpha olefin, more preferably propylene and or butene.

"Elastomers" encompass all natural and synthetic rubbers, including those defined in ASTM D1566). Examples of preferred elastomers include, but are not limited to, ethylene propylene rubber, ethylene propylene diene monomer rubber, styrenic block copolymer rubbers (including SI, SIS, SB, SBS, SEBS and the like, where S=styrene, I=isobutylene, and B=butadiene), butyl rubber, halobutyl rubber, copolymers of isobutylene and para-alkylstyrene, halogenated copolymers of isobutylene and para-alkylstyrene, natural rubber, polyisoprene, copolymers of butadiene with acrylonitrile, polychloroprene, alkyl acrylate rubber, chlorinated isoprene rubber, acrylonitrile chlorinated isoprene rubber, polybutadiene rubber (both cis and trans).

In another embodiment, the polymer produced by this invention is combined with one or more of isotactic polypropylene, highly isotactic polypropylene, syndiotactic polypropylene, random copolymer of propylene and ethylene and/or butene and/or hexene, polybutene, ethylene vinyl acetate, low density polyethylene (density 0.915 to less than 0.935 g/cm³) linear low density polyethylene, ultra low density polyethylene (density 0.86 to less than 0.90 g/cm³), very low density polyethylene (density 0.90 to less than 0.915 g/cm³), medium density polyethylene (density 0.935 to less than 0.945 g/cm³), high density polyethylene (density 0.945 to 0.98 g/cm³), ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, crosslinked polyethylene, polymers that are a hydrolysis product of EVA that equate to an ethylene vinyl alcohol copolymer, polymers of aromatic monomers such as polystyrene, poly-1 esters, polyacetal, polyvinylidine fluoride, polyethylene glycols and/or polyisobutylene.

In another embodiment elastomers are blended with the polymer produced by this invention to form rubber toughened compositions. In some particularly preferred embodiments, the rubber toughened composition is a two (or more) phase system where the elastomer is a discontinuous phase and the polymer produced by this invention is a continuous phase. This blend may be combined with tackifiers and/or other additives as described herein.

In another embodiment the polymer produced by this invention may be blended with elastomers or other soft polymers to form impact copolymers. In some embodiments the blend is a two (or more) phase system where the elastomer or soft polymer is a discontinuous phase and the polymer produced by this invention is a continuous phase. This blend may be combined with tackifiers and/or other additives as described herein.

In some embodiments the polymers of the invention described above are combined with metallocene polyethylenes (mPEs) or metallocene polypropylenes (mPPs). The mPE and mPP homopolymers or copolymers are typically produced using mono- or bis-cyclopentadienyl transition metal catalysts in combination with an activator of alumoxane and/or a non-coordinating anion in solution, slurry, high pressure or gas phase. The catalyst and activator may be supported or unsupported and the cyclopentadienyl rings by may substituted or unsubstituted. Several commercial products produced with such catalyst/activator combinations are commercially available from ExxonMobil Chemical Company in Baytown, Tex. under the tradenames EXCEED™, ACHIEVE™ and EXACT™. For more information on the methods and catalysts/activators to produce such homopolymers and copolymers see WO 94/26816; WO 94/03506; EPA 277,003; EPA 277,004; U.S. Pat. No. 5,153,157; U.S. Pat. No. 5,198,401; U.S. Pat. No. 5,240,894; U.S. Pat. No. 5,017,714; CA 1,268,753; U.S. Pat. No. 5,324,800; EPA 129,368; U.S. Pat. No. 5,264,405; EPA 520,732; WO 92 00333; U.S. Pat. No. 5,096,867; U.S. Pat. No. 5,507,475; EPA 426 637; EPA 573 403; EPA 520 732; EPA 495 375; EPA 500 944; EPA 570 982; WO91/09882; WO94/03506 and U.S. Pat. No. 5,055,438.

In some embodiments the polymer of this invention is present in the above blends, at from 10 to 99 weight %, based upon the weight of the polymers in the blend, preferably 20 to 95 weight %, even more preferably at least 30 to 90 weight %, even more preferably at least 40 to 90 weight %, even more preferably at least 50 to 90 weight %, even more preferably at least 60 to 90 weight %, even more preferably at least 70 to 90 weight %.

The blends described above may be produced by (a) mixing the polymers of the invention with one or more polymers (as described above), by (b) connecting reactors together in series to make in situ reactor blends or by (c) using more than one catalyst in the same reactor to produce multiple species of polymers. The polymers can be mixed together prior to being put into the extruder or may be mixed in an extruder.

Any of the above polymers may be functionalized. Functionalized means that the polymer has been contacted with an unsaturated acid or anhydride. Preferred unsaturated acids or anhydrides include any unsaturated organic compound containing at least one double bond and at least one carbonyl group. Representative acids include carboxylic acids, anhydrides, esters and their salts, both metallic and non-metallic. Preferably the organic compound contains an ethylenic unsaturation conjugated with a carbonyl group (—C=O). Examples include maleic, fumaric, acrylic, methacrylic, itaconic, crotonic, alpha-methyl crotonic, and cinnamic acids as well as their anhydrides, esters and salt derivatives. Maleic anhydride is particularly preferred. The unsaturated acid or anhydride is preferably present at about 0.1 weight % to about 5 weight %, preferably at about 0.5 weight % to about 4 weight %, even more preferably at about 1 to about 3 weight %, based upon the weight of the hydrocarbon resin and the unsaturated acid or anhydride.

Tackifiers may be blended with the polymers of this invention and/or with blends of the polymer produced by this inventions (as described above). Examples of useful tackifiers include, but are not limited to, aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, polyterpenes, aromatic modified polyterpenes, terpene phenolics, aromatic modified hydrogenated polycyclopentadiene resins, hydrogenated aliphatic resin, hydrogenated aliphatic aromatic resins, hydrogenated terpenes and modified terpenes, and hydrogenated rosin esters. In some embodiments the tackifier is hydrogenated. In other embodiments the tackifier is non-polar. (Non-polar tackifiers are substantially free of monomers having polar groups. Preferably the polar groups are not present; however, if present, they are preferably not present at more that 5 weight %, preferably not more that 2 weight %, even more preferably no more than 0.5 weight %.) In some embodiments the tackifier has a softening point (Ring and Ball, as measured by ASTM E-28) of 80° C. to 140° C., preferably 100° C. to 130° C. In some embodiments the tackifier is functionalized. By functionalized is meant that the hydrocarbon resin has been contacted with an unsaturated acid or anhydride. Preferred unsaturated acids or anhydrides include any unsaturated organic compound containing at least one double bond and at least one carbonyl group. Representative acids include carboxylic acids, anhydrides, esters and their salts, both metallic and non-metallic. Preferably the organic compound contains an ethylenic unsaturation conjugated with a carbonyl group (—C=O). Examples include maleic, fumaric, acrylic, methacrylic, itaconic, crotonic, alpha-methyl crotonic, and cinnamic acids as well as their anhydrides, esters and salt derivatives. Maleic anhydride is particularly preferred. The unsaturated acid or anhydride is preferably present at about 0.1 weight % to about 10 weight %, preferably at about 0.5 weight % to about 7 weight %, even more preferably at about 1 to about 4 weight %, based upon the weight of the hydrocarbon resin and the unsaturated acid or anhydride.

The tackifier, if present, is typically present at about 1 weight % to about 50 weight %, based upon the weight of the blend, more preferably 10 weight % to 40 weight %, even more preferably 20 weight % to 40 weight %. Preferably however, tackifier is not present, or if present, is present at less than 10 weight %, preferably less than 5 weight %, more preferably at less than 1 weight %.

In another embodiment the polymers of this invention, and/or blends thereof, further comprise a crosslinking agent. Preferred crosslinking agents include those having functional groups that can react with the acid or anhydride group. Preferred crosslinking agents include alcohols, multiols, amines, diamines and/or triamines. Examples of crosslinking agents useful in this invention include polyamines such as ethylenediamine, diethylenetriamine, hexamethylenediamine, diethylaminopropylamine, and/or menthanediamine.

In another embodiment the polymers of this invention, and/or blends thereof, further comprise typical additives known in the art such as fillers, cavitating agents, antioxidants, surfactants, adjuvants, plasticizers, block, antiblock, color masterbatches, pigments, dyes, processing aids, UV stabilizers, neutralizers, lubricants, waxes, and/or nucleating agents. The additives may be present in the typically effective amounts well known in the art, such as 0.001 weight % to 10 weight %.

Preferred fillers, cavitating agents and/or nucleating agents include titanium dioxide, calcium carbonate, barium sulfate, silica, silicon dioxide, carbon black, sand, glass beads, mineral aggregates, talc, clay and the like.

Preferred antioxidants include phenolic antioxidants, such as Irganox 1010, Irganox, 1076 both available from Ciba-Geigy. Preferred oils include paraffinic or naphthenic oils such as Primol 352, or Primol 876 available from ExxonMobil Chemical France, S.A. in Paris, France.

More preferred oils include aliphatic naphthenic oils, white oils or the like.

Preferred plasticizers and/or adjuvants include mineral oils, polybutenes, phthalates and the like. Particularly preferred plasticizers include phthalates such as diisoundecyl phthalate (DIUP), diisononylphthalate (DINP), dioctylphthalates (DOP) and polybutenes, such as Parapol 950 and Parapol 1300 available from ExxonMobil Chemical Company in Houston Tex. Additional Preferred plasticizers include those disclosed in WO0118109A1 and U.S. Ser. No. 10/640,435, which are fully incorporated herein by reference.

Preferred processing aids, lubricants, waxes, and/or oils include low molecular weight products such as wax, oil or low Mn polymer, (low meaning below Mn of 5000, preferably below 4000, more preferably below 3000, even more preferably below 2500). Preferred waxes include polar or non-polar waxes, functionalized waxes, polypropylene waxes, polyethylene waxes, and wax modifiers. Preferred waxes include ESCOMER™ 101.

Preferred functionalized waxes include those modified with an alcohol, an acid, or a ketone. Functionalized means that the polymer has been contacted with an unsaturated acid or anhydride. Preferred unsaturated acids or anhydrides include any unsaturated organic compound containing at least one double bond and at least one carbonyl group. Representative acids include carboxylic acids, anhydrides, esters and their salts, both metallic and non-metallic. Preferably the organic compound contains an ethylenic unsaturation conjugated with a carbonyl group (—C=O). Examples include maleic, fumaric, acrylic, methacrylic, itaconic, crotonic, alpha-methyl crotonic, and cinnamic acids as well as their anhydrides, esters and salt derivatives. Maleic anhydride is particularly preferred. The unsaturated acid or anhydride is preferably present at about 0.1 weight % to about 10 weight %, preferably at about 0.5 weight % to about 7 weight %, even more preferably at about 1 to about 4 weight %, based upon the weight of the hydrocarbon resin and the unsaturated acid or anhydride. Preferred examples include waxes modified by methyl ketone, maleic anhydride or maleic acid. Preferred low Mn polymers include polymers of lower alpha olefins such as propylene, butene, pentene, hexene and the like. A particularly preferred polymer includes polybutene having an Mn of less than 1000. An example of such a polymer is available under the trade name PARAPOL™ 950 from ExxonMobil Chemical Company. PARAPOL™ 950 is an liquid polybutene polymer having an Mn of 950 and a kinematic viscosity of 220 cSt at 100° C., as measured by ASTM D 445.

Preferred UV stabilizers and or antioxidants include Irganox 1010 and the like.

In a particularly preferred embodiment, the polymers produced herein (alone or blended with other polymers or components) may be blended with a non-functionalized plasticizer ("NFP"). Typically the NFP is present in the blend at from 1 to 75 weight %, preferably 5 to 60 weight %, preferably 10 to 50 weight %, based upon the weight of the composition. Likewise typically the polymers produced herein are present in the blend at 25 to 99 weight %, preferably 40 to 95 weight %, preferably 50 to 90 weight %, based upon the weight of the composition.

The classes of materials described herein that are useful as non-functionalized plasticizers can be utilized alone or admixed with other NFP's described herein in order to obtain desired properties. Any NFP useful in the present invention may also be described by any number of, or any combination of, parameters described herein.

Preferably the NFP is a liquid with no distinct melting point above 0° C. and a kinematic viscosity at 25° C. of 30,000 cSt or less.

In one embodiment, the NFP is a compound comprising carbon and hydrogen, and does not include to an appreciable extent, functional groups selected from hydroxide, aryls and substituted aryls, halogens, alkoxys, carboxylates, esters, carbon unsaturation, acrylates, oxygen, nitrogen, and carboxyl. In yet another embodiment, aromatic moieties (including any compound whose molecules have the ring structure characteristic of benzene, naphthalene, phenanthrene, anthracene, etc.) are substantially absent from the NFP. By "appreciable extent", it is meant that these groups and compounds comprising these groups are not deliberately added to the NFP, and if present at all, are present at less than 5 wt % by weight of the NFP in one embodiment, more preferably less than 4 weight %, more preferably less than 3 weight %, more preferably less than 2 weight %, more preferably less than 1 weight %, more preferably less than 0.7 weight %, more preferably less than 0.5 weight %, more preferably less than 0.3 weight %, more preferably less than 0.1 weight %, more preferably less than 0.05 weight %, more preferably less than 0.01 weight %, more preferably less than 0.001 weight %, based upon the weight of the NFP. By "substantially absent", it is meant that these compounds are not added deliberately to the compositions and if present at all, are present at less than 0.5 wt %.

In another embodiment, the NFP is a hydrocarbon that does not contain olefinic unsaturation to an appreciable extent. By "appreciable extent of olefinic unsaturation" it is meant that the carbons involved in olefinic bonds account for less than 10%, preferably less than 9%, more preferably less than 8%, more preferably less than 7%, more preferably less than 6%, more preferably less than 5%, more preferably less than 4%, more preferably less than 3%, more preferably less than 2%, more preferably less than 1%, more preferably less than 0.7%, more preferably less than 0.5%, more preferably less than 0.3%, more preferably less than 0.1%, more preferably less than 0.05%, more preferably less than 0.01%, more preferably less than 0.001%, of the total number of carbons. In some embodiments, the percent of carbons of the NFP involved in olefinic bonds is between 0.001 and 10% of the total number of carbon atoms in the NFP, preferably between 0.01 and 7%, preferably between 0.1 and 5%, more preferably less than 1%.

In another embodiment, the NFP comprises $C_6$ to $C_{200}$ paraffins (preferably $C_8$ to $C_{100}$ paraffins), where the NFP has a) a specific gravity of 0.85 or less and b) a pour point of –20° C. or less. In another embodiment, the NFP consists essentially of $C_6$ to $C_{200}$ paraffins (preferably the NFP consists essentially of $C_8$ to $C_{100}$ paraffins) where the NFP has a) a specific gravity of 0.85 or less and b) a pour point of –20° C. or less.

In certain embodiments of the present invention, the NFP having a) a specific gravity of 0.85 or less and b) a pour point of –20° C. or less has one or more of the following properties:

1. a distillation range as determined by ASTM D86 having a difference between the upper temperature and the lower temperature of 40° C. or less, preferably 30° C. or less, preferably 20° C. or less, preferably 10° C. or less, preferably between 6 and 40° C.; and/or
2. a final boiling point as determined by ASTM D 86 of from 115° C. to 500° C., preferably from 200° C. to 450° C., preferably from 250° C. to 400° C.; and/or
3. a number average molecular weight (Mn) between 2,000 and 100 g/mol, preferably between 1,500 and 150 g/mol, more preferably between 1,000 and 200 g/mol; and/or
4. a dielectric constant at 20° C. of less than 3.0, preferably less than 2.8, preferably less than 2.5, preferably less than 2.3, preferably less than 2.1; and/or
5. a viscosity (ASTM 445, 25° C.) of from 0.5 to 20 cSt at 25° C.; and/or
6. a glass transition temperature (Tg) determined by ASTM E1356 of less than 0° C., preferably less than –10° C., more preferably less than –20° C., more preferably less than –30° C., more preferably less than –50° C., or most preferably a Tg that can not be determined by ASTM E1356.

In other embodiments, the NFP having a) a specific gravity of 0.85 or less and b) a pour point of –20° C. or less preferably comprises at least 50 wt %, preferably at least 60 wt %, preferably at least 70 wt %, preferably at least 80 wt %, preferably at least 90 wt %, preferably at least 95 wt %, preferably 100 wt % of $C_6$ to $C_{150}$ isoparaffins, preferably $C_6$ to $C_{100}$ isoparaffins, preferably $C_6$ to $C_{25}$ isoparaffins, more preferably $C_8$ to $C_{20}$ isoparaffins. Preferably the density (ASTM 4052, 15.6/15.6° C.) of these isoparaffins ranges from 0.70 to 0.83 g/cm³; the pour point is –40° C. or less, preferably –50° C. or less, the viscosity (ASTM 445, 25° C.) is from 0.5 to 20 cSt at 25° C.; and the number average molecular weights in the range of 100 to 300 g/mol. Suitable isoparaffins are described in, for example, U.S. Pat. Nos. 6,197,285, 3,818,105 and 3,439,088, and are commercially available under the tradename ISOPAR™ (ExxonMobil Chemical), some of which are summarized in the following Table.

| | ISOPAR Series Isoparaffins | | | | |
|---|---|---|---|---|---|
| Name | Distillation range (° C.) | pour point (° C.) | Specific Gravity | Kinematic Visc. @ 25° C. (cSt) | saturates & aromatics (wt %) |
| ISOPAR E | 117-136 | –63 | 0.72 | 0.85 | <0.01 |
| ISOPAR G | 161-176 | –57 | 0.75 | 1.46 | <0.01 |
| ISOPAR H | 178-188 | –63 | 0.76 | 1.80 | <0.01 |
| ISOPAR K | 179-196 | –60 | 0.76 | 1.85 | <0.01 |
| ISOPAR L | 188-207 | –57 | 0.77 | 1.99 | <0.01 |
| ISOPAR M | 223-254 | –57 | 0.79 | 3.80 | <0.01 |
| ISOPAR V | 272-311 | –63 | 0.82 | 14.8 | <0.01 |

Other suitable isoparaffins are also commercially available under the trade names SHELLSOL™ (Royal Dutch/Shell), SOLTROL™ (Chevron Phillips) and SASOL™ (Sasol Limited).

In another embodiment, the isoparaffins are a mixture of branched and normal paraffins having from 6 to 50 carbon atoms, and from 10 to 24 carbon atoms in another embodiment, in the molecule. The isoparaffin composition has a ratio of branch paraffin to n-paraffin ratio (branch paraffin:n-paraffin) ranging from 0.5:1 to 9:1 in one embodiment, and from 1:1 to 4:1 in another embodiment. The isoparaffins of the mixture in this embodiment contain greater than 50 wt % (by total weight of the isoparaffin composition) monomethyl species, for example, 2-methyl, 3-methyl, 4-methyl, 5-methyl or the like, with minimum formation of branches with substituent groups of carbon number greater than 1, such as, for example, ethyl, propyl, butyl or the like, based on the total weight of isoparaffins in the mixture. In one embodiment, the isoparaffins of the mixture contain greater than 70 wt % of the mono-methyl species, based on the total weight of the isoparaffins in the mixture. The isoparaffinic mixture boils within a range of from 100° C. to 350° C. in one embodiment, and within a range of from 110° C. to 320° C. in another embodiment. In preparing the different grades, the paraffinic mixture is generally fractionated into cuts having narrow boiling ranges, for example, 35° C. boiling ranges. These branch paraffin/n-paraffin blends are described in, for example, U.S. Pat. No. 5,906,727.

In another embodiment, the NFP comprises $C_{25}$ to $C_{1500}$ paraffins, and $C_{30}$ to $C_{500}$ paraffins in another embodiment, and has a flash point of 200° C. or more and a pour point of −10° C. or less and a viscosity index of 120 or more. Alternately the NFP comprises $C_{25}$ to $C_{1500}$ paraffins, preferably $C_{30}$ to $C_{500}$ paraffins, and has a flash point of 200° C. or more and a pour point of −20° C. or less. Alternately the NFP comprises $C_{25}$ to $C_{1500}$ paraffins, preferably $C_{30}$ to $C_{500}$ paraffins, and has a flash point of 200° C. or more and a kinematic viscosity at 100° C. of 35 cSt or more. In another embodiment, the NFP consists essentially of $C_{35}$ to $C_{300}$ paraffins, preferably the NFP consists essentially of $C_{40}$ to $C_{250}$ paraffins, and has a flash point of 200° C. or more and a pour point of −10° C. or less and a viscosity index of 120 or more. Alternately the NFP consists essentially of $C_{35}$ to $C_{300}$ paraffins, preferably $C_{40}$ to $C_{250}$ paraffins, and has a flash point of 200° C. or more and a pour point of −20° C. or less. Alternately the NFP consists essentially of $C_{35}$ to $C_{300}$ paraffins, preferably $C_{40}$ to $C_{250}$ paraffins, and has a flash point of 200° C. or more and a kinematic viscosity at 100° C. of 35 cSt or more. Alternately the NFP has a flash point of 200° C. or more and a pour point of −20° C. or less. Alternately the NFP has a flash point of 200° C. or more and a kinematic viscosity at 100° C. of 35 cSt or more.

In another embodiment, the NFP comprises polyalphaolefin (PAO) oligomers of $C_5$ to $C_{20}$ olefins, and oligomers of $C_6$ to $C_{18}$ olefins in another embodiment, and oligomers of $C_6$ to $C_{14}$ olefins in yet another embodiment. In a preferred embodiment the NFP comprises oligomers of $C_8$ to $C_{12}$ 1-olefins. In a more preferred embodiment, the NFP comprises oligomers of linear C8 to $C_{12}$ 1-olefins, and most preferred are oligomers of linear $C_{10}$ 1-olefins. In a preferred embodiment, the NFP comprises oligomers of $C_8$ $C_{10}$ and $C_{12}$ 1-olefins, preferably 1-octene, 1-decene and 1-dodecene.

In another embodiment the NFP comprises polyalphaolefins (PAO) oligomers of linear olefins having 5 to 18 carbon atoms, more preferably 6 to 12 carbon atoms, more preferably 10 carbon atoms, where an individual PAO or a combination of PAO's has a kinematic viscosity (KV) at 100° C. of 3 cSt or more, preferably 6 cSt or more, preferably 8 cSt or more, preferably 10 cSt or more (as measured by ASTM D445); and preferably having a viscosity index (VI) of 100 or more, preferably 110 or more, more preferably 120 or more, more preferably 130 or more, more preferably 140 or more, preferably 150 or more (as determined by ASTM D2270); and preferably having a pour point of −10° C. or less, more preferably −20° C. or less, more preferably −30° C. or less (as determined by ASTM D97).

In another embodiment, the NFP comprises $C_{20}$ to $C_{1500}$ (preferably $C_{35}$ to $C_{400}$, more preferably $C_{40}$ to $C_{250}$) polyalphaolefin oligomers. The PAO oligomers are preferably dimers, trimers, tetramers, pentamers, etc. of $C_5$ to $C_{14}$ α-olefins in one embodiment, and $C_6$ to $C_{14}$ α-olefins in another embodiment, and $C_8$ to $C_{12}$ α-olefins in another embodiment, and $C_{10}$ α-olefins in another embodiment. Suitable olefins include 1-pentene, 1-hexene, 1-heptene, 1-octene, 1-nonene, 1-decene, 1-undecene and 1-dodecene, and blends thereof. In one embodiment, the olefin is 1-decene, and the NFP is a mixture of dimers, trimers, tetramers and pentamers (and higher) of 1-decene. In another embodiment, the PAO is comprised of oligomers or polymers of 1-octene, 1-decene, and 1-dodecene. Preferred PAO's are described more particularly in, for example, U.S. Pat. Nos. 5,171,908, and 5,783,531 and in SYNTHETIC LUBRICANTS AND HIGH-PERFORMANCE FUNCTIONAL FLUIDS 1-52 (Leslie R. Rudnick & Ronald L. Shubkin, ed. Marcel Dekker, Inc. 1999). The PAO oligomers or polymers useful in the present invention may be characterized by any degree of tacticity, including isotacticity or syndiotacticity, and may be atactic. In another embodiment the polyalphaolefin has more than 50% meso dyads as measured by $^{13}$Carbon NMR, preferably more than 60%. In another embodiment the polyalphaolefin has more than 50% racemic dyads as measured by $^{13}$Carbon NMR, preferably more than 60%.

PAO's useful in the present invention typically possess a number average molecular weight of from 300 to 21,000 g/mol in one embodiment, from 400 to 20,000 g/mol in another embodiment, from 500 to 10,000 g/mol in another embodiment, from 500 to 5,000 g/mol in another embodiment, from 600 to 3,000 g/mol in another embodiment, and from 500 to 1,500 g/mol in yet another embodiment. Preferred PAO's have kinematic viscosities at 100° C. in the range of 3 to 3000 cSt in one embodiment, from 4 to 3000 cSt in another embodiment, from 6 to 300 cSt in another embodiment, and from 8 to 100 cSt in another embodiment, and 10 cSt or greater in another embodiment; and have pour points of less than −10° C. in one embodiment, and less than −20° C. in another embodiment, and less than −25° C. in another embodiment, and less than −30° C. in another embodiment, and less than −35° C. in another embodiment, and less than −40° C. in yet another embodiment. Desirable PAO's are commercially available as SpectraSyn™ and SpectraSyn Ultra™ (ExxonMobil Chemical, previously sold under the SHF and SuperSyn™ tradenames), some of which are summarized in the Table below.

| PAO | KV @ 100° C., cSt | VI | Pour Point, ° C. | Specific gravity | Flash Point, ° C. | APHA Color |
|---|---|---|---|---|---|---|
| SpectraSyn 4 | 4 | 126 | −66 | 0.820 | 220 | 10 |
| SpectraSyn 6 | 6 | 138 | −57 | 0.827 | 246 | 10 |
| SpectraSyn 8 | 8 | 139 | −48 | 0.833 | 260 | 10 |
| SpectraSyn 10 | 10 | 137 | −48 | 0.835 | 266 | 10 |
| SpectraSyn 40 | 39 | 147 | −36 | 0.850 | 281 | 10 |
| SpectraSyn 100 | 100 | 170 | −30 | 0.853 | 283 | 60 |
| SpectraSyn Ultra 150 | 150 | 218 | −33 | 0.850 | >265 | 10 |
| SpectraSyn Ultra 300 | 300 | 241 | −27 | 0.852 | >265 | 20 |
| SpectraSyn Ultra 1000 | 1,000 | 307 | −18 | 0.855 | >265 | 30 |

Other useful PAO's include those sold under the tradenames Synfluid™ available from ChevronPhillips Chemical Company (Pasedena, Tex.), Durasyn™ available from BP Amoco Chemicals (London, England), Nexbase™ available from Fortum Corporation (Keilaniemi, Finland), and Synton™ available from Crompton Corporation (Middlebury, Conn.).

In other embodiments the PAO's have a kinematic viscosity at 100° C. of 3 cSt or more, preferably 6 cSt or more, preferably 8 cSt or more, preferably 10 cSt or more, preferably 20 cSt or more, preferably 300 cSt or less, preferably 100 cSt or less. In another embodiment the PAO's have a kinematic viscosity at 100° C. of between 3 and 1000 cSt, preferably between 6 and 300 cSt, preferably between 8 and 100 cSt, preferably between 8 and 40 cSt.

In other embodiments the PAO's have a Viscosity Index of 100 or more, preferably 110 or more, preferably 120 or more, preferably 130 or more, preferably 140 or more, preferably 150 or more, preferably 170 or more, preferably 200 or more, preferably 250 or more.

In other embodiments the PAO's have a pour point of −10° C. or less, preferably −20° C. or less, preferably −25° C. or less, preferably −30° C. or less, preferably −35° C. or less, preferably −40° C. or less, preferably −50° C. or less.

In other embodiments the PAO's have a flash point of 200° C. or more, preferably 210° C. or more, preferably 220° C. or more, preferably 230° C. or more, preferably between 240° C. and 290° C.

Particularly preferred PAO's for use herein are those having a) a flash point of 200° C. or more (preferably 210° C. or more, preferably 220° C. or more, preferably 230° C. or more); and b) a pour point less than −20° C. (preferably less than −25° C., preferably less than −30° C., preferably less than −35°, preferably less than −40° C.) or a kinematic viscosity at 100° C. of 35 cSt or more (preferably 40 cSt or more, preferably 50 cSt or more, preferably 60 cSt or more).

In another embodiment, the NFP is a high purity hydrocarbon fluid with a branched paraffin:normal paraffin ratio ranging from about 0.5:1 to 9:1, preferably from about 1:1 to 4:1. The branched paraffins of the mixture contain greater than 50 wt % (based on the total weight of the branched paraffins) mono-methyl species, for example, 2-methyl, 3-methyl, 4-methyl, 5-methyl or the like, with minimum formation of branches with substituent groups of carbon number greater than 1, such as, for example, ethyl, propyl, butyl or the like; preferably, greater than 70 wt % of the branched paraffins are mono-methyl species. The paraffin mixture has a number-average molecular weight in the range of 280 to 7000 g/mol, preferably 420 to 5600 g/mol, preferably 560 to 2800 g/mol, preferably 350 to 2100 g/mol, preferably 420 to 1400 g/mol, more preferably 280 to 980 g/mol; has a kinematic viscosity at 100° C. ranging from 3 to 500 cSt, preferably 6 to 200 cSt, preferably 8 to 100 cSt, more preferably 6 to 25 cSt, more preferably 3 to 25 cSt, more preferably 3 to 15 cSt; and boils within a range of from 100 to 350° C., preferably within a range of from 110 to 320° C., preferably within a range of 150 to 300° C. In a preferred embodiment, the paraffinic mixture is derived from a Fischer-Tropsch process. These branch paraffin/n-paraffin blends are described in, for example, U.S. Pat. No. 5,906,727.

In another embodiment, the NFP comprises paraffinic hydrocarbons having:
1. a number average molecular weight of 300 to 10,000 g/mol, preferably 400 to 5,000 g/mol, preferably 500 to 2,500 g/mol, preferably 300 to 1,200 g/mol;
2. less than 10% of sidechains with 4 or more carbons, preferably less than 8%, preferably less than 5%, preferably less than 3%, preferably less than 2%, preferably less than 1%, preferably less than 0.5%, preferably less than 0.1%;
3. at least 15% of sidechains with 1 or 2 carbons, preferably 20% or more, preferably 25% or more, preferably 30% or more, preferably 35% or more, preferably 40% or more, preferably 45% or more, preferably 50% or more;
4. less than 2.5 wt % cyclic paraffins (based on the total weight of paraffins in the mixture), preferably less than 2 wt %, preferably less than 1 wt %, preferably less than 0.5 wt %, preferably less than 0.1 wt %, preferably at less than 0.1 wt %, preferably at 0.001 wt %;
5. a kinematic viscosity at 100° C. of 3 cSt or more, preferably 6 cSt or more, preferably 8 cSt or more, preferably between 3 and 25 cSt; and
6. a viscosity index (VI) of 110 or more, preferably 120 or more, preferably 130 or more, preferably 140 or more, preferably 150 or more, preferably 180 or more, preferably 200 or more, preferably 250 or more, preferably 300 or more;
7. a pour point of −10° C. or less, preferably −20° C. or less; and
8. a flash point of 200° C. or more, preferably 210° C. or more, preferably 220° C. or more.

In another embodiment, the NFP comprises a wax isomerate lubricant oil basestock, which includes hydroisomerized waxy stocks (e.g. waxy stocks such as gas oils, slack waxes, fuels hydrocracker bottoms, etc.), hydroisomerized Fischer-Tropsch hydrocarbons and waxes, Gas-to-Liquids (GTL) base stocks and base oils, and other waxy feedstock derived hydroisomerized base stocks and base oils, or mixtures thereof. Fischer-Tropsch waxes, the high boiling point residues of Fischer-Tropsch synthesis, are highly paraffinic hydrocarbons with very low sulfur content, and are often preferred feedstocks in processes to make hydrocarbon fluids of lubricating viscosity.

The hydroprocessing used for the production of such base stocks may use an amorphous hydrocracking/hydroisomerization catalyst, such as one of the specialized lube hydrocracking catalysts or a crystalline hydrocracking/hydroisomerization catalyst, preferably a zeolitic catalyst. For example, one useful catalyst is ZSM-48 as described in U.S. Pat. No. 5,075,269. Processes for making hydrocracked/hydroisomerized distillates and hydrocracked/hydroisomerized waxes are described, for example, in U.S. Pat. Nos. 2,817,693; 4,975,177; 4,921,594 and 4,897,178 as well as in British Patent Nos. 1,429,494; 1,350,257; 1,440,230 and 1,390,359. Particularly favorable processes are described in European Patent Application Nos. 464546 and 464547. Processes using Fischer-Tropsch wax feeds are described in U.S. Pat. Nos. 4,594,172 and 4,943,672.

Gas-to-Liquids (GTL) base stocks and base oils, Fischer-Tropsch hydrocarbon derived base stocks and base oils, and other waxy feedstock derived base stocks and base oils (or wax isomerates) that can be advantageously used in the present invention have kinematic viscosities at 100° C. of about 3 cSt to about 500 cSt, preferably about 6 cSt to about 200 cSt, preferably about 8 cSt to about 100 cSt, more preferably about 3 cSt to about 25 cSt. These Gas-to-Liquids (GTL) base stocks and base oils, Fischer-Tropsch hydrocarbon derived base stocks and base oils, and other waxy feedstock derived base stocks and base oils (or wax isomerates) have low pour points (preferably less than −10° C., preferably about −15° C. or lower, preferably about −25° C. or lower, preferably −30° C. to about −40° C. or lower); have a high viscosity index (preferably 110 or greater, preferably 120 or greater, preferably 130 or greater, preferably 150 or greater); and are of high purity (high saturates levels (preferably 90 wt % or more, preferably 95 wt % or more, preferably 99 wt % or more), low-to-nil sulfur content (preferably 0.03 weight % or less), low-to-nil nitrogen content (preferably 0.05 wt % or less), low-to-nil aromatics content (preferably 0.05 wt % or less), low bromine number (preferably 1 or less), low iodine number (preferably 1 or less), and high aniline point (preferably 120° C. or more). Useful compositions of Gas-to-Liquids (GTL) base stocks and base oils, Fischer-Tropsch hydrocarbon derived base stocks and base oils, and wax isomerate hydroisomerized base stocks and base oils are recited in U.S. Pat. Nos. 6,080,301; 6,090,989; and 6,165,949; for example, and are fully incorporated herein by reference.

In a preferred embodiment, the NFP of the present invention comprises a GTL-derived base-stock or base-oil that has a kinematic viscosity at 100° C. of 3 to 500 cSt, preferably 6 to 200 cSt, preferably 8 to 100 cSt, more preferably 3 to 25 cSt; and/or a number average molecular weight ($M_n$) of 300 to 10,000 g/mol, preferably 400 to 5,000 g/mol, preferably 500 to 2,500 g/mol, more preferably 300 to 1,200 g/mol.

In another embodiment, the NFP comprises a Group III hydrocarbon oil (also called a lubricant basestock), which is a special class of mineral oils that is severely hydrotreated. Preferably the NFP has a saturates levels of 90% or more, preferably 92% or more, preferably 94% or more, preferably 95% or more, and sulfur contents less than 0.03%, preferably between 0.001 and 0.01%, and VI of 120 or more, preferably 130 or more. Preferably the Group III hydrocarbon oil has a kinematic viscosity at 100° C. of 3 to 100, preferably 4 to 100 cSt, preferably 6 to 50 cSt, preferably 8 to 20; and/or a number average molecular weight of 300 to 5,000 g/mol, preferably 400 to 2,000 g/mol, more preferably 500 to 1,000 g/mol. Preferably the Group III hydrocarbon oil has a pour point of −10° C. or less, and a flash point of 200° C. or more.

In some embodiments, the NFP comprises a low molecular weight of $C_4$ olefins (including n-butene, 2-butene, isobutylene, and butadiene, and mixtures thereof). Such a material is referred to as a "polybutenes" liquid when the oligomers comprise isobutylene and/or 1-butene and/or 2-butene. It is commonly used as an additive for polyolefins; e.g. to introduce tack or as a processing aid. The ratio of $C_4$ olefin isomers can vary by manufacturer and by grade, and the material may or may not be hydrogenated after synthesis. In some cases, the polybutenes liquid is a polymer of a $C_4$ raffinate stream. In other cases, it consists essentially of polyisobutylene or poly(n-butene) oligomers. Typically, the polybutenes liquid has a number-average molecular weight of less than 15,000 g/mol, and commonly less than 5,000 g/mol or even less than 1,000 g/mol. They are described in, for example, SYNTHETIC LUBRICANTS AND HIGH-PERFORMANCE FUNCTIONAL FLUIDS 357-392 (Leslie R. Rudnick & Ronald L. Shubkin, ed., Marcel Dekker 1999). Commercial sources of polybutenes include BP (Indopol grades) and Infineum (C-Series grades). When the $C_4$ olefin is exclusively isobutylene, the material is referred to as "polyisobutylene" or PIB. Commercial sources of PIB include Texas Petrochemical (TPC Enhanced PIB grades). When the $C_4$ olefin is exclusively 1-butene, the material is referred to as "poly-n-butene" or PNB. Properties of some liquids made from $C_4$ olefin(s) are summarized in the Table below. Note that grades with a flash point of 200° C. or more also have a pour point greater than −10° C. and/or a VI less than 120. Preferably, the NFP is not a polybutenes liquid.

Commercial Examples of Oligomers of $C_4$ olefin(s)

| Grade | KV @ 100° C., cSt | VI | Pour Point, ° C. | Specific gravity | Flash Point, ° C. |
|---|---|---|---|---|---|
| TPC 137 (PIB) | 6 | 132 | −51 | 0.843 | 120 |
| TPC 1105 (PIB) | 220 | 145 | −6 | 0.893 | 200 |
| TPC 1160 (PIB) | 660 | 190 | 3 | 0.903 | 230 |

-continued

Commercial Examples of Oligomers of $C_4$ olefin(s)

| Grade | KV @ 100° C., cSt | VI | Pour Point, ° C. | Specific gravity | Flash Point, ° C. |
|---|---|---|---|---|---|
| BP Indopol H-25 | 52 | 87 | −23 | 0.869 | ~150 |
| BP Indopol H-50 | 108 | 90 | −13 | 0.884 | ~190 |
| BP Indopol H-100 | 218 | 121 | −7 | 0.893 | ~210 |
| Infineum C9945 | 11 | 74* | −34 | 0.854 | 170 |
| Infineum C9907 | 78 | 103* | −15 | 0.878 | 204 |
| Infineum C9995 | 230 | 131* | −7 | 0.888 | 212 |
| Infineum C9913 | 630 | 174* | 10 | 0.888 | 240 |

*Estimated based on the kinematic viscosity at 100° C. and 38° C.

In another embodiment, when a NFP is present, an oligomer or polymer of $C_4$ olefin(s) (including all isomers, e.g. n-butene, 2-butene, isobutylene, and butadiene, and mixtures thereof) may be present in the composition. In a preferred embodiment, the composition comprises less than 50 wt % (preferably less than 40%, preferably less than 30 wt %, preferably less than 20 wt %, more preferably less than 10 wt %, more preferably less than 5 wt %, more preferably less than 1 wt %, preferably 0 wt %) polymer or oligomer of $C_4$ olefin(s) such as PIB, polybutene, or PNB, based upon the weight of the composition.

In a preferred embodiment, the NFP contains less than 90 weight % of $C_4$ olefin(s), preferably isobutylene, based upon the weight of the NFP. Preferably the NFP contains less than 80 weight %, preferably less than 70 wt %, preferably less than 60 wt %, preferably less than 50 wt %, preferably less than 40 wt %, preferably less than 30 wt %, preferably less than 20 wt %, preferably less than 10 wt %, preferably 5 wt %, preferably less than 2%, preferably less than 1 wt %, preferably 0 wt % of $C_4$ olefin(s), preferably isobutylene, based upon the weight of the NFP.

In another embodiment, any NFP described herein has a pour point (ASTM D97) of less than −10° C. in one embodiment, less than −20° C. in another embodiment, less than −25° C. in yet another embodiment, less than −30° C. in yet another embodiment, less than −35° C. in yet another embodiment, less than −40° C. in yet another embodiment, less than −45° C. in yet another embodiment, less than −50° C. in yet another embodiment, and less than −60° C. in yet another embodiment, and greater than −120° C. in yet another embodiment, wherein a desirable range may include any upper pour point limit with any lower pour point limit described herein.

In another embodiment, any NFP described herein has a Viscosity Index (VI, ASTM D2270) of 100 or more, preferably 105 or more, more preferably 110 or more, more preferably 115 or more, more preferably 120 or more, more preferably 125 or more, more preferably 130 or more, more preferably 150 or more. In another embodiment the NFP has a VI between 100 and 300, preferably between 120 and 180.

In another embodiment, any NFP described herein has a kinematic viscosity at 100° C. ($KV_{100}$, ASTM D445) of from 3 to 3000 cSt, and from 6 to 300 cSt in another embodiment, and from 6 to 200 cSt in another embodiment, and from 8 to 100 cSt in yet another embodiment, and from 4 to 50 cSt in yet another embodiment, and less than 50 cSt in yet another embodiment, and less than 25 cSt in yet another embodiment, wherein a desirable range may comprise any upper viscosity limit with any lower viscosity limit described herein. In other embodiments, the NFP has a kinematic viscosity at 100° C. of less than 2 cSt.

In another embodiment, any NFP described herein has a flash point (ASTM D92) of 200° C. or more, preferably 210° C. or more, preferably 220° C. or more, preferably 230° C. or more, preferably 240° C. or more, preferably 245° C. or more, preferably 250° C. or more, preferably 260° C. or more, preferably 270° C. or more, preferably 280° C. or more. In another embodiment the NFP has a flash point between 200° C. and 300° C., preferably between 220° C. and 280° C. In other embodiments, the NFP has a flash point between 100° C. and 200° C.

In another embodiment, any NFP described herein has a dielectric constant measured at 20° C. of less than 3.0 in one embodiment, and less than 2.8 in another embodiment, less than 2.5 in another embodiment, and less than 2.3 in yet another embodiment, and less than 2.1 in yet another embodiment. Polyethylene itself has a dielectric constant (1 kHz, 23° C.) of at least 2.3 according to the CRC HANDBOOK OF CHEMISTRY AND PHYSICS (David R. Lide, ed. $82^d$ ed. CRC Press 2001).

In another embodiment, any NFP described herein has a specific gravity (ASTM D4052, 15.6/15.6° C.) of less than 0.86 in one embodiment, and less than 0.85 in another embodiment, and less than 0.84 in another embodiment, and less than 0.83 in another embodiment, and from 0.80 to 0.86 in another embodiment, and from 0.81 to 0.85 in another embodiment, and from 0.82 to 0.84 in another embodiment, wherein a desirable range may comprise any upper specific gravity limit with any lower specific gravity limit described herein.

In other embodiments, any NFP described herein may have an initial boiling point (ASTM D1160) of from 300° C. to 600° C. in one embodiment, and from 350° C. to 500° C. in another embodiment, and greater than 400° C. in yet another embodiment.

In other embodiments any NFP described herein may have a low degree of color, such as typically identified as "water white", "prime white", "standard white", or "bright and clear," preferably an APHA color of 100 or less, preferably 80 or less, preferably 60 or less, preferably 40 or less, preferably 20 or less, as determined by ASTM D1209.

Any NFP described herein preferably has a number-average molecular weight ($M_n$) of 21,000 g/mol or less in one embodiment, preferably 20,000 g/mol or less, preferably 19,000 g/mol or less, preferably 18,000 g/mol or less, preferably 16,000 g/mol or less, preferably 15,000 g/mol or less, preferably 13,000 g/mol or less and 10,000 g/mol or less in yet another embodiment, and 5,000 g/mol or less in yet another embodiment, and 3,000 g/mol or less in yet another embodiment, and 2,000 g/mol or less in yet another embodiment, and 1500 g/mol or less in yet another embodiment, and 1,000 g/mol or less in yet another embodiment, and 900 g/mol or less in yet another embodiment, and 800 g/mol or less in yet another embodiment, and 700 g/mol or less in yet another embodiment, and 600 g/mol or less in yet another embodiment, and 500 g/mol or less in yet another embodiment. Preferred minimum $M_n$ is at least 200 g/mol, preferably at least 300 g/mol. Further a desirable molecular weight range can be any combination of any upper molecular weight limit with any lower molecular weight limit described above. $M_n$ is determined according to the methods specified under Fluid Properties in the Test Methods section below.

Any of the NFP's may also be described by any number of, or any combination of, parameters described herein.

In a preferred embodiment, any NFP described herein has a flash point of 200° C. or more (preferably 210° C. or more) and a pour point of –20° C. or less (preferably –25° C. or less, more preferably –30° C. or less, more preferably –35° C. or less, more preferably –45° C. or less, more preferably –50° C. or less).

In another preferred embodiment, the NFP has a flash point of 220° C. or more (preferably 230° C. or more) and a pour point of –10° C. or less (preferably –25° C. or less, more preferably –30° C. or less, more preferably –35° C. or less, more preferably –45° C. or less, more preferably –50° C. or less).

In another preferred embodiment, the NFP has a kinematic viscosity at 100° C. of 35 cSt or more (preferably 40 cSt or more, preferably 50 cSt or more, preferably 60 cSt or more) and a specific gravity (15.6/15.6° C.) of 0.87 or less (preferably 0.865 or less, preferably 0.86 or less, preferably 0.855 or less) and a flash point of 200° C. or more (preferably 230° C. or more).

In another preferred embodiment, the NFP has a) a flash point of 200° C. or more, b) a specific gravity of 0.86 or less, and c1) a pour point of –10° C. or less and a viscosity index of 120 or more, or c2) a pour point of –20° C. or less, or c3) a kinematic viscosity at 100° C. of 35 cSt or more.

In another preferred embodiment, the NFP has a specific gravity (15.6/15.6° C.) of 0.85 or less (preferably between 0.80 and 0.85) and a kinematic viscosity at 100° C. of 3 cSt or more (preferably 4 or more, preferably 5 cSt or more, preferably 8 cSt or more, preferably 10 cSt or more, preferably 15 cSt or more, preferably 20 cSt or more) and/or a number-average molecular weight ($M_n$) of at least 280 g/mol.

In another preferred embodiment, the NFP has a specific gravity (15.6/15.6° C.) of 0.86 or less (preferably between 0.81 and 0.855, preferably between 0.82 and 0.85) and a kinematic viscosity at 100° C. of 5 cSt or more (preferably 6 or more, preferably 8 cSt or more, preferably 10 cSt or more, preferably 12 cSt or more, preferably 15 cSt or more, preferably 20 cSt or more) and/or a number-average molecular weight ($M_n$) of at least 420 g/mol.

In another preferred embodiment, the NFP has a specific gravity (15.6/15.6° C.) of 0.87 or less (preferably between 0.82 and 0.87) and a kinematic viscosity at 100° C. of 10 cSt or more (preferably 12 cSt or more, preferably 14 cSt or more, preferably 16 cSt or more, preferably 20 cSt or more, preferably 30 cSt or more, preferably 40 cSt or more) and/or a number-average molecular weight ($M_n$) of at least 700 g/mol.

In another preferred embodiment, the NFP has a specific gravity (15.6/15.6° C.) of 0.88 or less (preferably 0.87 or less, preferably between 0.82 and 0.87) and a kinematic viscosity at 100° C. of 15 cSt or more (preferably 20 cSt or more, preferably 25 cSt or more, preferably 30 cSt or more, preferably 40 cSt or more) and/or a number-average molecular weight ($M_n$) of at least 840 g/mol.

In another preferred embodiment the NFP has a kinematic viscosity at 100° C. of 3 to 3000 cSt, preferably 6 to 300 cSt, more preferably 8 to 100 cSt; and a number average molecular weight ($M_n$) of 300 to 21,000 g/mol, preferably 500 to 5,000 g/mol, more preferably 600 to 3,000 g/mol.

In another preferred embodiment the NFP has a kinematic viscosity at 100° C. of 3 to 500 cSt, preferably 6 to 200 cSt, more preferably 8 to 100 cSt, more preferably 3 to 25 cSt; and a number average molecular weight ($M_n$) of 300 to 10,000 g/mol, preferably 400 to 5,000 g/mol, more preferably 500 to 2,500 g/mol, more preferably 300 to 1,200 g/mol.

In another preferred embodiment the NFP has a kinematic viscosity at 100° C. of 3 to 100 cSt, preferably 4 to 50 cSt, more preferably 6 to 25 cSt, more preferably 3 to 15 cSt; and a number average molecular weight ($M_n$) of 300 to 3,000 g/mol, preferably 350 to 2,000 g/mol, more preferably 400 to 1,000 g/mol, more preferably 300 to 800 g/mol.

In another preferred embodiment, the NFP has a pour point of −25° C. or less, preferably between −30° C. and −90° C., and a kinematic viscosity in the range of from 20 to 5000 cSt at 40° C. In another preferred embodiment, the NFP has a pour point of −25° C. or less and a Mn of 400 g/mol or greater. Most mineral oils, which typically include functional groups, have a pour point of from 10° C. to −25° C. at the same viscosity and molecular weight ranges.

In another preferred embodiment the NFP has kinematic viscosity at 100° C. of 3 cSt or greater, preferably 6 cSt or greater, more preferably 8 cSt or greater, and one or more of the following properties:
1. a pour point of −10° C. or less, preferably −20° C. or less, preferably −30° C. or less, preferably −40° C. or less; and/or,
2. a Viscosity Index of 120 or greater; and/or,
3. a low degree of color, such as typically identified as "water white", "prime white", "standard white", or "bright and clear," preferably an APHA color of 100 or less, preferably 80 or less, preferably 60 or less, preferably 40 or less, preferably 20 or less, preferably 15 or less as determined by ASTM D1209; and/or
4. a flash point of 200° C. or more, preferably 220° C. or more, preferably 240° C. or more; and/or
5. a specific gravity (15.6° C.) of less than 0.86.

Most mineral oils at the same viscosity range have a pour point greater than −20° C. or an APHA color of greater than 20 or a specific gravity (15.6° C.) of 0.86 or more.

In another preferred embodiment, the NFP has a Viscosity Index of 120 or more and one or more of the following properties:
1. a pour point of −10° C. or less, preferably −20° C. or less, preferably −30° C. or less, preferably −40° C. or less; and/or,
2. a kinematic viscosity at 100° C. of 3 cSt or greater, preferably 6 cSt or greater, preferably 8 cSt or greater, preferably 10 cSt or greater; and/or,
3. a low degree of color, such as typically identified as "water white", "prime white", "standard white", or "bright and clear," preferably an APHA color of 100 or less, preferably 80 or less, preferably 60 or less, preferably 40 or less, preferably 20 or less, preferably 15 or less, as determined by ASTM D1209; and/or
4. a flash point of 200° C. or more, preferably 220° C. or more, preferably 240° C. or more; and/or
5. a specific gravity (15.6° C.) of less than 0.86.

Most mineral oils have a Viscosity Index of less than 120.

In another preferred embodiment, the NFP has a pour point of −20° C. or less, preferably −30° C. or less, and one or more of the following properties:
1. a kinematic viscosity at 100° C. of 3 cSt or greater, preferably 6 cSt or greater, preferably 8 cSt or greater, preferably 10 cSt or more; and/or,
2. a Viscosity Index of 120 or greater, preferably 130 or greater; and/or,
3. a low degree of color, such as typically identified as "water white", "prime white", "standard white", or "bright and clear," preferably APHA color of 100 or less, preferably 80 or less, preferably 60 or less, preferably 40 or less, preferably 20 or less, preferably 15 or less as determined by ASTM D1209
4. a flash point of 200° C. or more, preferably 220° C. or more, preferably 240° C. or more; and/or
5. a specific gravity (15.6° C.) of less than 0.86.

Most mineral oils have a kinematic viscosity at 100° C. of less than 6 cSt, or an APHA color of greater than 20, or a flash point less than 200° C. when their pour point is less than −20° C.

In another preferred embodiment the NFP has a glass transition temperature ($T_g$) that cannot be determined by ASTM E1356 or, if it can be determined, then the $T_g$ according to ASTM E1356 is less than 0° C., preferably less than −10° C., more preferably less than −20° C., more preferably less than −30° C., more preferably less than −40° C., and, preferably, also has one or more of the following properties:
1. an initial boiling point as determined by ASTM D1160 greater than 300° C., preferably greater than 350° C., preferably greater than 400° C.; and/or
2. a pour point of −10° C. or less, preferably −15° C. or less, preferably −25° C. or less, preferably −35° C. or less, preferably −45° C. or less; and/or
3. a specific gravity (ASTM D4052, 15.6/15.6° C.) of less than 0.88, preferably less than 0.86, preferably less than 0.84, preferably from 0.80 to 0.88, preferably from 0.82 to 0.86; and/or
4. a final boiling point as determined by ASTM D1160 of from 300° C. to 800° C., preferably from 400° C. to 700° C., preferably greater than 500° C.; and/or
5. a weight average molecular weight ($M_w$) between 30,000 and 400 g/mol preferably between 15,000 and 500 g/mol, more preferably between 5,000 and 600 g/mol; and/or
6. a number average molecular weight ($M_n$) between 10,000 and 400 g/mol, preferably between 5,000 and 500 g/mol, more preferably between 2,000 and 600 g/mol; and/or
7. a flash point as measured by ASTM D92 of 200° C. or greater, and/or
8. a dielectric constant at 20° C. of less than 3.0, preferably less than 2.8, preferably less than 2.5, preferably less than 2.3, preferably less than 2.2.

In another embodiment the NFP may be a copolymer as described in U.S. Pat. No. 6,639,020.

In another embodiment of the present invention, compositions of this invention comprise less than 50 wt % (preferably less than 40 wt %, preferably less than 30 wt %, preferably less than 20 wt %, preferably less than 10 wt %, more preferably less than 5 wt %, more preferably less than 1 wt %) of EP Rubber, based upon the total weight of the composition. For purposes of this invention and the claims thereto, an EP Rubber is defined to be a copolymer of ethylene and propylene, and optionally diene monomer(s), where the ethylene content is from 35 to 80 weight %, the diene content is 0 to 15 weight %, and the balance is propylene; and where the copolymer has a Mooney viscosity, ML(1+4) @125° C. (measured according to ASTM D1646) of 15 to 100.

In another embodiment, the compositions of this invention comprise less than 10 wt % (preferably less than 5 wt %, preferably less than 3 wt %, preferably less than 2 wt %, preferably less than 1 wt %, more preferably less than 0.5 wt %, more preferably less than 0.1 wt %) of an elastomer, based upon the total weight of the composition. By "elastomers" is meant all natural and synthetic rubbers, including those defined in ASTM D1566. Examples of elastomers include ethylene propylene rubber, ethylene propylene diene monomer rubber, styrenic block copolymer rubbers (including SEBS, SI, SIS, SB, SBS, SIBS and the like, where S=styrene, EB=random ethylene+butene, I=isoprene, and B=butadiene), butyl rubber, halobutyl rubber, copolymers of isobutylene and para-alkylstyrene, halogenated copolymers of isobutylene and para-alkylstyrene, natural rubber, polyisoprene, copolymers of butadiene with acrylonitrile, polychloroprene, alkyl acrylate rubber, chlorinated isoprene rubber, acrylonitrile chlorinated isoprene rubber, polybutadiene rubber (both cis and trans).

APPLICATIONS

The polymers of this invention (and blends thereof as described above) whether formed in situ or by physical blending are preferably used in any known thermoplastic or elastomer application. Examples include uses in molded parts, films, tapes, sheets, tubing, hose, sheeting, wire and cable coating, adhesives, shoe soles, bumpers, gaskets, bellows, films, fibers, elastic fibers, nonwovens, spunbonds, sealants, surgical gowns and medical devices.

Adhesives

The polymers of this invention or blends thereof can be used as adhesives, either alone or combined with tackifiers. The tackifier is typically present at about 1 weight % to about 50 weight %, based upon the weight of the blend, more preferably 10 weight % to 40 weight %, even more preferably 20 weight % to 40 weight %. Other additives, as described above, may be added also.

The adhesives of this invention can be used in any adhesive application, including but not limited to, disposables, packaging, laminates, pressure sensitive adhesives, tapes labels, wood binding, paper binding, non-wovens, road marking, reflective coatings, and the like. In some embodiments the adhesives of this invention can be used for disposable diaper and napkin chassis construction, elastic attachment in disposable goods converting, packaging, labeling, bookbinding, woodworking, and other assembly applications. Particularly preferred applications include: baby diaper leg elastic, diaper frontal tape, diaper standing leg cuff, diaper chassis construction, diaper core stabilization, diaper liquid transfer layer, diaper outer cover lamination, diaper elastic cuff lamination, feminine napkin core stabilization, feminine napkin adhesive strip, industrial filtration bonding, industrial filter material lamination, filter mask lamination, surgical gown lamination, surgical drape lamination, and perishable products packaging.

The adhesives described above may be applied to any substrate. Preferred substrates include wood, paper, cardboard, plastic, thermoplastic, rubber, metal, metal foil (such as aluminum foil and tin foil), metallized surfaces, cloth, non-wovens (particularly polypropylene spun bonded fibers or non-wovens), spunbonded fibers, cardboard, stone, plaster, glass (including silicon oxide ($SiO_x$)coatings applied by evaporating silicon oxide onto a film surface), foam, rock, ceramics, films, polymer foams (such as polyurethane foam), substrates coated with inks, dyes, pigments, PVDC and the like or combinations thereof. Additional preferred substrates include polyethylene, polypropylene, polyacrylates, acrylics, polyethylene terephthalate, or any of the polymers listed above as suitable for blends. Corona treatment, electron beam irradiation, gamma irradiation, microwave or silanization may modify any of the above substrates.

Films

The polymer produced by this invention described above and the blends thereof may be formed into monolayer or multilayer films. These films may be formed by any of the conventional techniques known in the art including extrusion, co-extrusion, extrusion coating, lamination, blowing, tenter frame, and casting. The film may be obtained by the flat film or tubular process, which may be followed by orientation in an uniaxial direction, or in two mutually perpendicular directions in the plane of the film. One or more of the layers of the film may be oriented in the transverse and/or longitudinal directions to the same or different extents. This orientation may occur before or after the individual layers are brought together. For example, a polyethylene layer can be extrusion coated or laminated onto an oriented polypropylene layer or the polyethylene and polypropylene can be coextruded together into a film then oriented. Likewise, oriented polypropylene could be laminated to oriented polyethylene or oriented polyethylene could be coated onto polypropylene then optionally the combination could be oriented even further. Typically the films are oriented in the Machine Direction (MD) at a ratio of up to 15, preferably between 5 and 7, and in the Transverse Direction (TD) at a ratio of up to 15 preferably 7 to 9. However in another embodiment the film is oriented to the same extent in both the MD and TD directions. In another embodiment the layer comprising the polymer composition of this invention (and/or blends thereof) may be combined with one or more other layers. The other layer(s) may be any layer typically included in multilayer film structures. For example, the other layer or layers may be:

1. Polyolefins. Preferred polyolefins include homopolymers or copolymers of $C_2$ to $C_{40}$ olefins, preferably $C_2$ to $C_{20}$ olefins, preferably a copolymer of an α-olefin and another olefin or α-olefin (ethylene is defined to be an α-olefin for purposes of this invention). Preferably homopolyethylene, homopolypropylene, propylene copolymerized with ethylene and or butene, ethylene copolymerized with one or more of propylene, butene or hexene, and optional dienes. Preferred examples include thermoplastic polymers such as ultra low density polyethylene, very low density polyethylene, linear low density polyethylene, low density polyethylene, medium density polyethylene, high density polyethylene, polypropylene, isotactic polypropylene, highly isotactic polypropylene, syndiotactic polypropylene, random copolymer of propylene and ethylene and/or butene and/or hexene, elastomers such as ethylene propylene rubber, ethylene propylene diene monomer rubber, neoprene, and blends of thermoplastic polymers and elastomers, such as, for example, thermoplastic elastomers and rubber toughened plastics.

2. Polar polymers. Preferred polar polymers include homopolymers and copolymers of esters, amides, acrylates, anhydrides, copolymers of a $C_2$ to $C_{20}$ olefin, such as ethylene and/or propylene and/or butene with one or more polar monomers such as acetates, anhydrides, esters, alcohol, and or acrylics. Preferred examples include polyesters, polyamides, ethylene vinyl acetate copolymers, and polyvinyl chloride.

3. Cationic polymers. Preferred cationic polymers include polymers or copolymers of geminally disubstituted olefins, alpha-heteroatom olefins and/or styrenic monomers. Preferred geminally disubstituted olefins include isobutylene, isopentene, isoheptene, isohexane, isooctene, isodecene, and isododecene. Preferred α-heteroatom olefins include vinyl ether and vinyl carbazole, preferred styrenic monomers include styrene, alkyl styrene, para-alkyl styrene, alpha-methyl styrene, chloro-styrene, and bromo-para-methyl styrene. Preferred examples of cationic polymers include butyl rubber, isobutylene copolymerized with para methyl styrene, polystyrene, and poly-α-methyl styrene.

4. Miscellaneous. Other preferred layers can be paper, wood, cardboard, metal, metal foils (such as aluminum foil and tin foil), metallized surfaces, glass (including silicon oxide (SiO.x)coatings applied by evaporating silicon oxide onto a film surface), fabric, spunbonded fibers, and non-wovens (particularly polypropylene spun bonded fibers or non-wovens), and substrates coated with inks, dyes, pigments, PVDC and the like. The films may vary in thickness depending on the intended application, however films of a thickness from 1 to 250 μm are usually suitable. Films intended for packaging are usually from 10 to 60 μm thick. The thickness of the sealing layer is typically 0.2 to 50 μm. There may be a sealing layer on both the inner and outer surfaces of the film or the sealing layer may be present on only the inner or the outer surface. Additives such as block, antiblock, antioxidants, pigments, fillers, processing aids, UV stabilizers, neutralizers, lubricants, surfactants and/or nucleating agents may also be present in one or more than one layer in the films. Preferred additives include silicon dioxide, titanium dioxide, polydimethylsiloxane, talc, dyes, wax, calcium stearate, carbon black, low molecular weight resins and glass beads. In another embodiment, one or more layers may be modified by corona treatment, electron beam irradiation, gamma irradiation, or microwave. In some embodiments, one or both of the surface layers is modified by corona treatment. The films described herein may also comprise from 5 to 60 weight %, based upon the weight of the polymer and the resin, of a hydrocarbon resin. The resin may be combined with the polymer of the seal layer(s) or may be combined with the polymer in the core layer(s). The resin preferably has a softening point above 100° C., even more preferably from 130 to 180° C. Preferred hydrocarbon resins include those described above. The films comprising a hydrocarbon resin may be oriented in uniaxial or biaxial directions to the same or different degrees.

The films described above may be used as stretch and/or cling films. Stretch/cling films are used in various bundling, packaging and palletizing operations. To impart cling properties to, or improve the cling properties of, a particular film, a number of well-known tackifying additives have been utilized. Common tackifying additives include polybutenes, terpene resins, alkali metal stearates and hydrogenated rosins and rosin esters. The well-known physical process referred to as corona discharge can also modify the cling properties of a film. Some polymers (such as ethylene methyl acrylate copolymers) do not need cling additives and can be used as cling layers without tackifiers. Stretch/clings films may comprise a slip layer comprising any suitable polyolefin or combination of polyolefins such as polyethylene, polypropylene, copolymers of ethylene and propylene, and polymers obtained from ethylene and/or propylene copolymerized with minor amounts of other olefins, particularly $C_4$-$C_{12}$ olefins. Particularly, preferred are polypropylene and linear low density polyethylene (LLDPE). Suitable polypropylene is normally solid and isotactic, i.e., greater than 90% hot heptane insolubles, having wide ranging melt flow rates of from about 0.1 to about 300 g/10 min. Additionally, the slip layer may include one or more anti-cling (slip and/or antiblock) additives, which may be added during the production of the polyolefin or subsequently blended in to improve the slip properties of this layer. Such additives are well-known in the art and include, for example, silicas, silicates, diatomaceous earths, talcs and various lubricants. These additives are preferably utilized in amounts ranging from about 100 ppm to about 20,000 ppm, more preferably between about 500 ppm to about 10,000 ppm, by weight based upon the weight of the slip layer. The slip layer may, if desired, also include one or more other additives as described above The films produced herein may also be used in heat sealing applications, particularly as heat sealing layers e.g. surface layers, in multilayer films. In a preferred embodiment, the polymers produced herein are used in heat sealing applications, such as packaging, form, fill and seal applications and packaging films such as biaxially oriented films. The polymers produced herein, alone or blended with other polymers, may be coextruded or laminated onto another polymer (typically in a film structure) and used in applications requiring good heat sealing.

For more information on the importance of good heat sealing behavior please see: (1) A new high performance mVLDPE. Halle, Richard W.; Malakoff, Alan M., Baytown Polymers Center, ExxonMobil Chemical Company, Baytown, Tex., USA. Polymers, Laminations, & Coatings Conference, San Diego, Calif., United States, Aug. 26-30, 2001 (2001), 457-466. Publisher: TAPPI Press, Atlanta, Ga.; (2) Seal through contamination performance of metallocene plastomers. Mesnil, Philippe; Arnauts, Jan; Halle, Richard W.; Rohse, Norbert., ExxonMobil Chemical Europe, Machelen, Belg., TAPPI Polymers, Laminations, & Coatings Conference, Proceedings, Chicago, Ill., United States, Aug. 27-31, 2000 (2000), 2 669-686. Publisher: TAPPI Press, Atlanta, Ga.; (3) Heat sealing of semi-crystalline polymer films. II. Effect of melting distribution on heat-sealing behavior of polyolefins. Stehling, Ferdinand C.; Meka, Prasadarao. Journal of Applied Polymer Science (1994), 51(1), 105-19. (4) EP 0 633 133 A1; and (5) JP 07156353A2, published Jun. 20, 1995 (claiming priority to JP93-339004).

Films

The polymer produced by this invention and blends thereof thereof may be formed into monolayer or multilayer films. These films may be formed by any of the conventional techniques known in the art including extrusion, co-extrusion, extrusion coating, lamination, blowing and casting. The film may be obtained by the flat film or tubular process which may be followed by orientation in an uniaxial direction or in two mutually perpendicular directions in the plane of the film. One or more of the layers of the film may be oriented in the transverse and/or longitudinal directions to the same or different extents. This orientation may occur before or after the individual layers are brought together. For example, a polyethylene layer can be extrusion coated or laminated onto an oriented polypropylene layer or the polyethylene and polypropylene can be coextruded together into a film then oriented. Likewise, oriented polypropylene could be laminated to oriented polyethylene or oriented polyethylene could be coated onto polypropylene then optionally the combination could be oriented even further. Typically the films are oriented in the Machine Direction (MD) at a ratio of up to 15, preferably between 5 and 7, and in the Transverse Direction (TD) at a ratio of up to 15 preferably 7 to 9. However in another embodiment the film is oriented to the same extent in both the MD and TD directions.

In another embodiment the layer comprising the polymer composition of this invention (and/or blends thereof) may be combined with one or more other layers. The other layer(s) may be any layer typically included in multilayer film structures. For example, the other layer or layers may be:
1. Polyolefins—Preferred polyolefins include homopolymers or copolymers of C2 to C40 olefins, preferably C2 to C20 olefins, preferably a copolymer of an alpha-olefin and another olefin or .alpha.-olefin (ethylene is defined to be an .alpha.-olefin for purposes of this invention). Preferably homopolyethylene, homopolypropylene, propylene copolymerized with ethylene and or butene, ethylene copolymerized with one or more of propylene, butene or hexene, and optional dienes. Preferred examples include thermoplastic polymers such as ultra low density polyethylene, very low density polyethylene, linear low density polyethylene, low density polyethylene, medium density polyethylene, high density polyethylene, polypropylene, isotactic polypropylene, highly isotactic polypropylene, syndiotactic polypropylene, random copolymer of propylene and ethylene and/or butene and/ or hexene, elastomers such as ethylene propylene rubber, ethylene propylene diene monomer rubber, neoprene, and blends of thermoplastic polymers and elastomers, such as for example, thermoplastic elastomers and rubber toughened plastics.

2. Polar Polymers—Preferred polar polymers include homopolymers and copolymers of esters, amides, actates, anhydrides, copolymers of a $C_2$ to $C_{20}$ olefin, such as ethylene and/or propylene and/or butene with one or more polar monomers such as acetates, anhydrides, esters, alcohol, and or acrylics. Preferred examples include polyesters, polyamides, ethylene vinyl acetate copolymers, and polyvinyl chloride.

3. Cationic polymers—Preferred cationic polymers include polymers or copolymers of geminally disubstituted olefins, alpha-heteroatom olefins and/or styrenic monomers. Preferred geminally disubstituted olefins include isobutylene, isopentene, isoheptene, isohexane, isooctene, isodecene, and isododecene. Preferred alpha-heteroatom olefins include vinyl ether and vinyl carbazole, preferred styrenic monomers include styrene, alkyl styrene, para-alkyl styrene, alpha-methyl styrene, chloro-styrene, and bromo-para-methyl styrene. Preferred examples of cationic polymers include butyl rubber, isobutylene copolymerized with para methyl styrene, polystyrene, and poly-.alpha.-methyl styrene.

4. Miscellaneous—Other preferred layers can be paper, wood, cardboard, metal, metal foils (such as aluminum foil and tin foil), metallized surfaces, glass (including silicon oxide (SiO.x)coatings applied by evaporating silicon oxide onto a film surface), fabric, spunbonded fibers, and non-wovens (particularly polypropylene spun bonded fibers or non-wovens), and substrates coated with inks, dyes, pigments, PVDC and the like.

The films may vary in thickness depending on the intended application, however films of a thickness from 1 to 250 µm are usually suitable. Films intended for packaging are usually from 10 to 60 microns thick. The thickness of the sealing layer is typically 0.2 to 50 µm. There may be a sealing layer on both the inner and outer surfaces of the film or the sealing layer may be present on only the inner or the outer surface.

Additives such as block, antiblock, antioxidants, pigments, fillers, processing aids, WV stabilizers, neutralizers, lubricants, surfactants and/or nucleating agents may also be present in one or more than one layer in the films. Preferred additives include silicon dioxide, titanium dioxide, polydimethylsiloxane, talc, dyes, wax, calcium stearate, carbon black, low molecular weight resins and glass beads.

In another embodiment one more layers may be modified by corona treatment, electron beam irradiation, gamma irradiation, or microwave. In a preferred embodiment one or both of the surface layers is modified by corona treatment.

The films described herein may also comprise from 5 to 60 weight %, based upon the weight of the polymer and the resin, of a hydrocarbon resin. The resin may be combined with the polymer of the seal layer(s) or may be combined with the polymer in the core layer(s). The resin preferably has a softening point above 100° C., even more preferably from 130 to 180° C. Preferred hydrocarbon resins include those described above. The films comprising a hydrocarbon resin may be oriented in uniaxial or biaxial directions to the same or different degrees.

The films described above may be used as stretch and/or cling films. Stretch/cling films are used in various bundling, packaging and palletizing operations. To impart cling properties to, or improve the cling properties of, a particular film, a number of well-known tackifying additives have been utilized. Common tackifying additives include polybutenes, terpene resins, alkali metal stearates and hydrogenated rosins and rosin esters. The cling properties of a film can also be modified by the well-known physical process referred to as corona discharge. Some polymers (such as ethylene methyl acrylate copolymers) do not need cling additives and can be used as cling layers without tackifiers. Stretch/clings films may comprise a slip layer comprising any suitable polyolefin or combination of polyolefins such as polyethylene, polypropylene, copolymers of ethylene and propylene, and polymers obtained from ethylene and/or propylene copolymerized with minor amounts of other olefins, particularly $C_4$ to $C_{12}$ olefins. Particularly preferred are polypropylene and linear low density polyethylene (LLDPE). Suitable polypropylene is normally solid and isotactic, i.e., greater than 90% hot heptane insolubles, having wide ranging melt flow rates of from about 0.1 to about 300 g/10 min. Additionally, the slip layer may include one or more anticling (slip and/or antiblock) additives which may be added during the production of the polyolefin or subsequently blended in to improve the slip properties of this layer. Such additives are well-known in the art and include, for example, silicas, silicates, diatomaceous earths, talcs and various lubricants. These additives are preferably utilized in amounts ranging from about 100 ppm to about 20,000 ppm, more preferably between about 500 ppm to about 10,000 ppm, by weight based upon the weight of the slip layer.

The slip layer may, if desired, also include one or more other additives as described above.

Melt Blown and Spun Bond Fabrics

The polymers made herein and blends thereof are useful for melt blown and spun bond fabrics. Invention processes can be used for making PP for spun bonded (SB) and melt blown (MB) fibers. Typical invention polymers have ash levels below 1000, 900, 700, 500, 400, 300, 200, 100, 50, 10, 1, 0.5, or 0.1 ppm. Some embodiments have ash levels of 1-500 ppb. All these characteristics combine to reduce polymer build-up on the die exits. These products can have high MFRs from 300-5000 useful for fiber applications.

Non-Wovens and Fibers

The polymers and blends thereof described herein may also be used to prepare the nonwoven fabrics and fibers in any nonwoven fabric and fiber making process, including but not limited to, melt blowing, spunbonding, film aperturing, and staple fiber carding. A continuous filament process may also be used. Preferably a spunbonding process is used. The spunbonding process is well known in the art. Generally it involves the extrusion of fibers through a spinneret. These fibers are then drawn using high velocity air and laid on an endless belt. A calendar roll is generally then used to heat the web and bond the fibers to one another although other techniques may be used such as sonic bonding and adhesive bonding.

Fiber Preparation

The formation of woven and nonwoven articles from the polymer, particularly a polymer/NFP blend typically requires the manufacture of fibers by extrusion followed by weaving or bonding. The extrusion process is typically accompanied by mechanical or aerodynamic drawing of the fibers. Essentially all fibers are oriented both during the extrusion process as well as during the process of manufacture of the non woven article.

a. Conventional Fine Denier PP Fibers

The three more conventional PP fiber operations, continuous filament, bulked continuous filament, and staple, are useful as means for preparing fibers of the blends of the present invention. Typically the molten blend is extruded through the holes in a die (spinneret) between 0.3 mm to 0.8 mm (10 mil to 30 mil) in diameter. Low melt viscosity of the polymer blend is preferred and is typically achieved through the use of high melt temperature (230° C. to 280° C.) and high melt flow rates (15 g/10 min to 40 g/10 min). A relatively large extruder is typically equipped with a manifold to distribute a high output of molten blend to a bank of eight to twenty spinnerets. Each spinhead is typically equipped with a separate gear pump to regulate output through that spinhead; a filter pack, supported by a "breaker plate;" and the spinneret plate within the head. The number of holes in the spinneret plate determines the number of filaments in a yarn and varies considerably with the different yarn constructions, but it is typically in the range of 50 to 250. The holes are typically grouped into round, annular, or rectangular patterns to assist in good distribution of the quench air flow.

b. Continuous Filament

Continuous filament yarns typically range from 40 denier to 2,000 denier (denier=number of grams/9000 yd). Filaments typically range from 1 to 20 dpf, but can be larger. Spinning speeds are typically 800 m/min to 1500 m/min (2500 ft/min to 5000 ft/min). The filaments are drawn at draw ratios of 3:1 or more (one- or two-stage draw) and wound onto a package. Two-stage drawing allows higher draw ratios to be achieved. Winding speeds are 2,000 m/min to 3,500 n/min (6,600 ft/min to 11,500 ft/min). Spinning speeds in excess of 900 m/min (3000 ft/min) require a NMWD to get the best spinnability with the finer filaments.

c. Bulked Continuous Filament

Bulked Continuous Filament fabrication processes fall into two basic types, one-step and two step. In the older, two-step process, an undrawn yarn is spun at less than 1,000 m/min (3,300 ft/min), usually 750 m/min, and placed on a package. The yarn is drawn (usually in two stages) and "bulked" on a machine called a texturizer. Winding and drawing speeds are limited by the bulking or texturizing device to 2,500 m/min (8,200 ft/min) or less. Typically if secondary crystallization occurs in the two-step CF process, then one typically promptly uses draw texturizing. The most common process today is the one-step spin/draw/text (SDT) process. This process provides better economics, efficiency and quality than the two-step process. It is similar to the one-step CF process, except that the bulking device is in-line. Bulk or texture changes yarn appearance, separating filaments and adding enough gentle bends and folds to make the yarn appear fatter (bulkier).

d. Staple Fiber

There are two basic staple fiber fabrication processes: traditional and compact spinning. The traditional process involves two steps: 1) producing, applying finish, and winding followed by 2) drawing, a secondary finish application, crimping, and cutting into staple. Filaments can range from 1.5 dpf to >70 dpf, depending on the application. Staple length can be as short as 7 mm or as long as 200 mm (0.25 in. to 8 in.) to suit the application. For many applications the fibers are crimped. Crimping is accomplished by overfeeding the tow into a steam-heated stuffer box with a pair of nip rolls. The over-feed folds the tow in the box, forming bends or crimps in the filaments. These bends are heat-set by steam injected into the box.

e. Melt-Blown Fibers

Melt blown fibers can make very fine filaments and produce very lightweight fabrics with excellent uniformity. The result is often a soft fabric with excellent "barrier" properties. In the melt blown process molten polymer moves from the extruder to the special melt blowing die. As the molten filaments exit the die, they are contacted by high temperature, high velocity air (called process or primary air). This air rapidly draws and, in combination with the quench air, solidifies the filaments. The entire fiber forming process generally takes place within 7 mm (0.25 in.) of the die. The fabric is formed by blowing the filaments directly onto a forming wire, 200 mm to 400 mm (8 in. to 15 in.) from the spinnerets.

Melt blown microfibers useful in the present invention can be prepared as described in Van A. Wente, "Superfine Thermoplastic Fibers," Industrial Engineering Chemistry, Vol. 48, pp. 1342-1346, and in Report No. 4364 of the Naval Research Laboratories, published May 25, 1954, entitled "Manufacture of Super Fine Organic Fibers" by Van A. Wente et al. In some preferred embodiments, the microfibers are used in filters. Such blown microfibers typically have an effective fiber diameter of from about 3 to 30 micrometers preferably from about 7 to 15 micrometers, as calculated according to the method set forth in Davies, C. N., "The Separation of Airborne Dust and Particles," Institution of Mechanical Engineers, London, Proceedings 1B, 1952.

f. Spunbonded Fibers

Fiber formation may also be accomplished by extrusion of the molten polymer from either a large spinneret having several thousand holes or with banks of smaller spinnerets containing as few as 40 holes. After exiting the spinneret, the molten fibers are quenched by a cross-flow air quench system, then pulled away from the spinneret and attenuated (drawn) by high pressure air. There are two methods of air attenuation, both of which use the venturi effect. The first draws the filament using an aspirator slot (slot draw), which runs the width of the machine. The second method draws the filaments through a nozzle or aspirator gun. Filaments formed in this manner are collected on a screen ("wire") or porous forming belt to form the fabric. The fabric is then passed through compression rolls and then between heated calendar rolls where the raised lands on one roll bond the fabric at points covering 20% to 40% of its area.

Annealing

In additional embodiments, the mechanical properties of fibers comprising the blends of this invention can be improved by the annealing the fibers or the non-woven materials made from the blends of this invention. Annealing is often combined with mechanical orientation, although annealing is preferred. Annealing partially relieves the internal stress in the stretched fiber and restores the elastic recovery properties of the blend in the fiber. Annealing has been shown to lead to significant changes in the internal organization of the crystalline structure and the relative ordering of the amorphous and semicrystalline phases. Annealing typically leads to improved elastic properties. The fiber or fabric is preferably annealed at a temperature of at least 40° F., preferably at least 20° F. above room temperature (but slightly below the crystalline melting point of the blend). Thermal annealing of the blend is conducted by maintaining the polymer blends or the articles made from a such a blend at temperature between room temperature to a maximum of 160° C. or more preferably to a maximum of 130° C. for a period between 5 minutes to less than 7 days. A typical annealing period is 3 days at 50° C. or 5 minutes at 100° C. While the annealing is done in the absence of mechanical orientation, the latter can be a part of the annealing process on the fiber (past the extrusion operation). Mechanical orientation can be done by the temporary, forced extension of the fiber for a short period of time before it is allowed to relax in the absence of the extensional forces. Oriented fibers are conducted by maintaining the fibers or the articles made from a blend at an extension of 100% to 700% for a period of 0.1 seconds to 24 hours. A typical orientation is an extension of 200% for a momentary period at room temperature.

For orientation, a fiber at an elevated temperature (but below the crystalline melting point of the polymer) is passed from a feed roll of fiber around two rollers driven at different surface speeds and finally to a take-up roller. The driven roller closest to the take-up roll is driven faster than the driven roller closest to the feed roll, such that the fiber is stretched between the driven rollers. The assembly may include a roller intermediate the second roller and take-up roller to cool the fiber. The second roller and the take-up roller may be driven at the same peripheral speeds to maintain the fiber in the stretched condition. If supplementary cooling is not used, the fiber will cool to ambient temperature on the take up roll.

For more information on fiber and non-woven production please see Polypropylene Handbook, E. P. Moore, Jr., et al., Hanser/Gardner Publications, Inc. New York, 1996, pp. 314 to 322, which is fully incorporated herein by reference.

Nonwoven Web

In a preferred embodiment, a nonwoven fiber web is prepared from the polymer, preferably a polymer/NFP blend, of this invention. The fibers employed in such a web typically and preferably have denier ranging from about 0.5 to about 10 (about 0.06 to about 11 tex), although higher denier fibers may also be employed. Fibers having denier from about 0.5 to 3 (0.06 to about 3.33 tex) are particularly preferred. ("Denier" means weight in grams of 9000 meters of fiber, whereas "tex" means weight in grams per kilometer of fiber.) Fiber stock having a length ranging from about 0.5 to about 10 cm is preferably employed as a starting material, particularly fiber lengths ranging from about 3 to about 8 cm. Nonwoven webs of fibers may be made using methods well documented in the nonwoven literature (see, for example, Turbak, A. "Nonwovens: An Advanced Tutorial", Tappi Press, Atlanta, Ga., (1989). The uncoated (i.e., before application of any binder) web should have a thickness in the range of about 10 to 100 mils (0.254 to 2.54 mm), preferably 30 to 70 mils (0.762 to 1.778 mm), more preferably 40 to 60 mils (1.02 to 1.524 mm). These preferred thicknesses may be achieved either by the carding/crosslapping operation or via fiber entanglement (e.g., hydroentanglement, needling, and the like). The basis weight of the uncoated web preferably ranges from about 50 g/m$^2$ up to about 250 g/m$^2$. In some embodiments, one may improve the tensile and tear strength of the inventive articles, and reduce lint on the surface of the articles, by entangling (such as by needle-tacking, hydroentanglement, and the like) the nonwoven web, or calendaring the uncoated and/or coated and cured nonwoven web. Hydroentanglement may be employed in cases where fibers are water insoluble. Calendaring of the nonwoven web at temperatures from about 5 to about 40° C. below the melting point of the fiber may reduce the likelihood of lint attaching to the surface of the articles and provide a smooth surface. Embossing of a textured pattern onto the nonwoven web may be performed simultaneously with calendaring, or in a subsequent step. In addition to the polyolefins and the NFP's of this invention, it may also be desirable to add colorants (especially pigments), softeners (such as ethers and alcohols), fragrances, fillers (such as, for example, silica, alumina, and titanium dioxide particles), and bactericidal agents (for example, iodine, quaternary ammonium salts, and the like) to the blends.

Likewise the nonwoven webs and fibers may be coated with other materials, such as binders, adhesives, reflectants, and the like. Coating of the nonwoven web or the fiber may be accomplished by methods known in the art, including roll coating, spray coating, immersion coating, gravure coating, or transfer coating. The coating weight as a percentage of the total wiping article may be from about 1% to about 95%, preferably from about 10% to about 60%, more preferably 20 to 40%.

Staple fibers may also be present in the nonwoven web. The presence of staple fibers generally provides a loftier, less dense web than a web of only blown microfibers. Preferably, no more than about 90 weight percent staple fibers are present, more preferably no more than about 70 weight percent. Such webs containing staple fiber are disclosed in U.S. Pat. No. 4,118,531 (Hauser) which is fully incorporated herein by reference.

Sorbent particulate material such as activated carbon or alumina may also be included in the web. Such particles may be present in amounts up to about 80 volume percent of the contents of the web. Such particle-loaded webs are described, for example, in U.S. Pat. No. 3,971,373 (Braun), U.S. Pat. No. 4,100,324 (Anderson), and U.S. Pat. No. 4,429,001 (Kolpin et al.), which are fully incorporated herein by reference.

The fibers and nonwoven webs prepared using the blends of this invention can be formed into fabrics, garments, clothing, medical garments, surgical gowns, surgical drapes, diapers, training pants, sanitary napkins, panty liners, incontinent wear, bed pads, bags, packaging material, packages, swimwear, body fluid impermeable backsheets, body fluid impermeable layers, body fluid permeable layers, body fluid permeable covers, absorbents, tissues, nonwoven composites, liners, cloth linings, scrubbing pads, face masks, respirators, air filters, vacuum bags, oil and chemical spill sorbents, thermal insulation, first aid dressings, medical wraps, fiberfill, outerwear, bed quilt stuffing, furniture padding, filter media, scrubbing pads, wipe materials, hosiery, automotive seats, upholstered furniture, carpets, carpet backing, filter media, disposable wipes, diaper coverstock, gardening fabric, geomembranes, geotextiles, sacks, housewrap, vapor barriers, breathable clothing, envelops, tamper evident fabrics, protective packaging, and coasters.

The fibers prepared using the blends of this invention can be formed into yarns, woven fabrics, nonwoven fabrics, hook and loop fasteners, fabrics, garments, clothing, medical garments, surgical gowns, surgical drapes, diapers, training pants, sanitary napkins, panty liners, incontinent wear, bed pads, bags, packaging material, packages, swimwear, body fluid impermeable backsheets, body fluid impermeable layers, body fluid permeable layers, body fluid permeable covers, absorbents, tissues, nonwoven composites, liners, cloth linings, scrubbing pads, face masks, respirators, air filters, vacuum bags, oil and chemical spill sorbents, thermal insulation, first aid dressings, medical wraps, fiberfill, outerwear, bed quilt stuffing, furniture padding, filter media, scrubbing pads, wipe materials, hosiery, automotive seats, upholstered furniture, carpets, carpet backing, filter media, disposable wipes, diaper coverstock, gardening fabric, geomembranes, geotextiles, sacks, housewrap, vapor barriers, breathable clothing, envelops, tamper evident fabrics, protective packaging, and coasters.

Waxes

An appropriate choice of operating conditions and monomer and comonomer feeds yields polypropylene waxes from the process described herein. Some invention embodiments are isotactic polypropylene waxes. As such these materials are well suited for viscosity modification in adhesives, as carriers for inks, and other applications. Some polypropylene waxes embodiments select melt viscosities of from 3-2000 cP at 180° C. Some invention embodiments produce syndiotactic polypropylene waxes.

Invention process can prepare long chain branched isotactic-polypropylene at high monomer conversion (35+% and especially 45+%) conditions. Some embodiments use higher amounts of diluent to promote long chain branching.

Long chain branching is also favored by operating the polymerization under supercritical conditions, but with a polymer rich phase and a polymer lean phase. Doing this allows the polymer-rich phase to have a lower monomer concentration and a higher local concentration of vinyl terminated polymer.

An appropriate choice of operating conditions and monomer and comonomer feeds, 180-200° C. and 20-150 MPa, yields polypropylene waxes from invention polymers and processes. Some invention embodiments are isotactic polypropylene waxes. As such these materials are well suited for viscosity modification in adhesives, films, and other applications. Some invention embodiments produce syndiotactic polypropylene waxes.

End Use Articles

Laminates comprising invention polymers can be used as a thermoformable sheet where the substrate is either sprayed or injection molded to couple it with the ionomer/tie-layer laminate sheet. The composite is formed into the desired shape to make the article, or composite article. Various types of substrate materials form highly desirable articles. The laminate can be used with plastic substrates such as homopolymers, copolymers, foams, impact copolymers, random copolymers, and other applications. Specifically, some articles in which the present invention can be incorporated are the following: vehicle parts, especially exterior parts such as bumpers and grills, rocker panels, fenders, doors, hoods, trim, and other parts can be made from the laminates, composites and methods of the invention.

Other articles can also be named, for example: counter tops, laminated surface counter tops, pool liners/covers/boat covers, boat sails, cable jacketing, motorcycles/snowmobiles/outdoor vehicles, marine boat hulls/canoe interior and exterior, luggage, clothing/fabric (combined with non-wovens), tent material, GORETEX™, Gamma-radiation resistant applications, electronics housing (TV's, VCR's and computers), a wood replacement for decks and other outdoor building materials, prefab buildings, synthetic marble panels for construction, wall covering, hopper cars, floor coating, polymer/wood composites, vinyl tile, bath/shower/toilet applications and translucent glass replacement, sidings, lawn/outdoor furniture, appliances such as refrigerators, washing machines, etc., children's toys, reflective signage and other reflective articles on roads and clothing, sporting equipment such as snowboards, surfboards, skis, scooters, wheels on in-line skates, CD's for scratch resistance, stadium seats, aerospace reentry shields, plastic paper goods, sports helmets, plastic microwaveable cookware, and other applications for coating plastics and metal where a highly glossy and scratch resistant surface is desirable, while not being subject to algae/discoloration.

The polypropylene copolymers described herein are suitable for applications such as molded articles, including injection and blow molded bottles and molded items used in automotive articles, such as automotive interior and exterior trims. Examples of other methods and applications for making polypropylene polymers and for which polypropylene polymers may be useful are described in the Encyclopedia of Chemical Technology, by Kirk-Othmer, Fourth Edition, Vol. 17, at pp. 748-819, which are fully incorporated herein by reference. In those instances where the application is for molded articles, the molded articles may include a variety of molded parts, particularly molded parts related to and used in the automotive industry such as, for example, bumpers, side panels, floor mats, dashboards and instrument panels. Foamed articles are another application and examples where foamed plastics, such as foamed polypropylene, are useful may be found in Encyclopedia of Chemical Technology, by Kirk-Othmer, Fourth Edition, Vol. 11, pp. 730-783, which are fully incorporated herein by reference herein. Foamed articles are particularly useful for construction and automotive applications. Examples of construction applications include heat and sound insulation, industrial and home appliances, and packaging. Examples of automotive applications include interior and exterior automotive parts, such as bumper guards, dashboards and interior liners.

The polyolefinic compositions of the present invention are suitable for such articles as automotive components, wire and cable jacketing, pipes, agricultural films, geomembranes, toys, sporting equipment, medical devices, casting and blowing of packaging films, extrusion of tubing, pipes and profiles, sporting equipment, outdoor furniture (e.g., garden furniture) and playground equipment, boat and water craft components, and other such articles. In particular, the compositions are suitable for automotive components such as bumpers, grills, trim parts, dashboards and instrument panels, exterior door and hood components, spoiler, wind screen, hub caps, mirror housing, body panel, protective side molding, and other interior and external components associated with automobiles, trucks, boats, and other vehicles.

Other useful articles and goods may be formed economically by the practice of our invention including: crates, containers, packaging, labware, such as roller bottles for culture growth and media bottles, office floor mats, instrumentation sample holders and sample windows; liquid storage containers such as bags, pouches, and bottles for storage and IV infusion of blood or solutions; packaging material including those for any medical device or drugs including unit-dose or other blister or bubble pack as well as for wrapping or containing food preserved by irradiation. Other useful items include medical tubing and valves for any medical device including infusion kits, catheters, and respiratory therapy, as well as packaging materials for medical devices or food which is irradiated including trays, as well as stored liquid, particularly water, milk, or juice, containers including unit servings and bulk storage containers as well as transfer means such as tubing, pipes, and such.

Molded Products

The polymers described above may also be used to prepare the molded products of this invention in any molding process, including but not limited to, injection molding, gas-assisted injection molding, extrusion blow molding, injection blow molding, injection stretch blow molding, compression molding, rotational molding, foam molding, thermoforming, sheet extrusion, and profile extrusion. The molding processes are well known to those of ordinary skill in the art.

The compositions described herein may be shaped into desirable end use articles by any suitable means known in the art. Thermoforming, vacuum forming, blow molding, rotational molding, slush molding, transfer molding, wet lay-up or contact molding, cast molding, cold forming matched-die molding, injection molding, spray techniques, profile co-extrusion, or combinations thereof are typically used methods.

Thermoforming is a process of forming at least one pliable plastic sheet into a desired shape. An embodiment of a thermoforming sequence is described, however this should not be construed as limiting the thermoforming methods useful with the compositions of this invention. First, an extrudate film of the composition of this invention (and any other layers or materials) is placed on a shuttle rack to hold it during heating. The shuttle rack indexes into the oven which pre-heats the film before forming. Once the film is heated, the shuttle rack indexes back to the forming tool. The film is then vacuumed onto the forming tool to hold it in place and the forming tool is closed. The forming tool can be either "male" or "female" type tools. The tool stays closed to cool the film and the tool is then opened. The shaped laminate is then removed from the tool.

Thermoforming is accomplished by vacuum, positive air pressure, plug-assisted vacuum forming, or combinations and variations of these, once the sheet of material reaches thermoforming temperatures, typically of from 140° C. to 185° C. or higher. A pre-stretched bubble step is used, especially on large parts, to improve material distribution. In one embodiment, an articulating rack lifts the heated laminate towards a male forming tool, assisted by the application of a vacuum from orifices in the male forming tool. Once the laminate is firmly formed about the male forming tool, the thermoformed shaped laminate is then cooled, typically by blowers. Plug-assisted forming is generally used for small, deep drawn parts. Plug material, design, and timing can be critical to optimization of the process. Plugs made from insulating foam avoid premature quenching of the plastic. The plug shape is usually similar to the mold cavity, but smaller and without part detail. A round plug bottom will usually promote even material distribution and uniform side-wall thickness. For a semicrystalline polymer such as polypropylene, fast plug speeds generally provide the best material distribution in the part.

The shaped laminate is then cooled in the mold. Sufficient cooling to maintain a mold temperature of 30° C. to 65° C. is desirable. The part is below 90° C. to 100° C. before ejection in one embodiment. For the good behavior in thermoforming, the lowest melt flow rate polymers are desirable. The shaped laminate is then trimmed of excess laminate material.

Blow molding is another suitable forming means, which includes injection blow molding, multi-layer blow molding, extrusion blow molding, and stretch blow molding, and is especially suitable for substantially closed or hollow objects, such as, for example, gas tanks and other fluid containers. Blow molding is described in more detail in, for example, CONCISE ENCYCLOPEDIA OF POLYMER SCIENCE AND ENGINEERING 90-92 (Jacqueline I. Kroschwitz, ed., John Wiley & Sons 1990).

In yet another embodiment of the formation and shaping process, profile co-extrusion can be used. The profile co-extrusion process parameters are as above for the blow molding process, except the die temperatures (dual zone top and bottom) range from 150° C.-235° C., the feed blocks are from 90° C.-250° C., and the water cooling tank temperatures are from 10° C.-40° C.

One embodiment of an injection molding process is described as follows. The shaped laminate is placed into the injection molding tool. The mold is closed and the substrate material is injected into the mold. The substrate material has a melt temperature between 200° C. and 300° C. in one embodiment, and from 215° C. and 250° C. and is injected into the mold at an injection speed of between 2 and 10 seconds. After injection, the material is packed or held at a predetermined time and pressure to make the part dimensionally and aesthetically correct. Typical time periods are from 5 to 25 seconds and pressures from 1,380 kPa to 10,400 kPa. The mold is cooled between 10° C. and 70° C. to cool the substrate. The temperature will depend on the desired gloss and appearance desired. Typical cooling time is from 10 to 30 seconds, depending on part on the thickness. Finally, the mold is opened and the shaped composite article ejected.

Likewise, molded articles may be fabricated by injecting molten polymer into a mold that shapes and solidifies the molten polymer into desirable geometry and thickness of molded articles. Sheet may be made either by extruding a substantially flat profile from a die, onto a chill roll, or alternatively by calendaring. Sheet will generally be considered to have a thickness of from 10 mils to 100 mils (254 μm to 2540 μm), although sheet may be substantially thicker. Tubing or pipe may be obtained by profile extrusion for uses in medical, potable water, land drainage applications or the like. The profile extrusion process involves the extrusion of molten polymer through a die. The extruded tubing or pipe is then solidified by chill water or cooling air into a continuous extruded articles. The tubing will generally be in the range of from 0.31 cm to 2.54 cm in outside diameter, and have a wall thickness of in the range of from 254 μm to 0.5 cm. The pipe will generally be in the range of from 2.54 cm to 254 cm in outside diameter, and have a wall thickness of in the range of from 0.5 cm to 15 cm. Sheet made from the products of an embodiment of a version of the present invention may be used to form containers. Such containers may be formed by thermoforming, solid phase pressure forming, stamping and other shaping techniques. Sheets may also be formed to cover floors or walls or other surfaces.

In an embodiment of the thermoforming process, the oven temperature is between 160° C. and 195° C., the time in the oven between 10 and 20 seconds, and the die temperature, typically a male die, between 10° C. and 71° C. The final thickness of the cooled (room temperature), shaped laminate is from 10 μm to 6000 μm in one embodiment, from 200 μm to 6000 μm in another embodiment, and from 250 μm to 3000 μm in yet another embodiment, and from 500 μm to 1550 μm in yet another embodiment, a desirable range being any combination of any upper thickness limit with any lower thickness limit.

In an embodiment of the injection molding process, wherein a substrate material in injection molded into a tool including the shaped laminate, the melt temperature of the substrate material is between 230° C. and 255° C. in one embodiment, and between 235° C. and 250° C. in another embodiment, the fill time from 2 to 10 seconds in one embodiment, from 2 to 8 seconds in another embodiment, and a tool temperature of from 25° C. to 65° C. in one embodiment, and from 27° C. and 60° C. in another embodiment. In a desirable embodiment, the substrate material is at a temperature that is hot enough to melt any tie-layer material or backing layer to achieve adhesion between the layers.

In yet another embodiment of the invention, the compositions of this invention may be secured to a substrate material using a blow molding operation. Blow molding is particularly useful in such applications as for making closed articles such as fuel tanks and other fluid containers, playground equipment, outdoor furniture and small enclosed structures. In one embodiment of this process, compositions of this invention are extruded through a multi-layer head, followed by placement of the uncooled laminate into a parison in the mold. The mold, with either male or female patterns inside, is then closed and air is blown into the mold to form the part.

It will be understood by those skilled in the art that the steps outlined above may be varied, depending upon the desired result. For example, the extruded sheet of the compositions of this invention may be directly thermoformed or blow molded without cooling, thus skipping a cooling step. Other parameters may be varied as well in order to achieve a finished composite article having desirable features.

Non-Wovens and Fibers

The polymers described above may also be used to prepare the nonwoven fabrics and fibers of this invention in any nonwoven fabric and fiber making process, including but not limited to, melt blowing, spunbonding, film aperturing, and staple fiber carding. A continuous filament process may also be used. Preferably a spunbonding process is used. The spunbonding process is well known in the art. Generally it involves the extrusion of fibers through a spinneret. These fibers are then drawn using high velocity air and laid on an endless belt. A calendar roll is generally then used to heat the web and bond the, fibers to one another although other techniques may be used such as sonic bonding and adhesive bonding. The fabric may be prepared with mixed metallocene polypropylene alone, physically blended with other mixed metallocene polypropylene or physically blended with single metallocene polypropylene. Likewise the fabrics of this invention may be prepared with mixed metallocene polypropylene physically blended with conventional Ziegler-Natta produced polymer. If blended, the fabric of this invention is preferably comprised of at least 50% mixed metallocene polypropylene. With these nonwoven fabrics, manufacturers can maintain the desirable properties of fabrics prepared with metallocene produced polypropylene while increasing fabric strength and potentially increased line speed compared to fabrics made using conventional polymers.

EXAMPLES

Size-Exclusion Chromatography of Polymers

Molecular weight distribution (Mw/Mn) was characterized using Size-Exclusion Chromatography (SEC). Molecular weight (weight-average molecular weight, Mw, number-average molecular weight, Mn, and z-average molecular weight, Mz) were determined using a High Temperature Size Exclusion Chromatograph (either from Waters Corporation or Polymer Laboratories), equipped with a differential refractive index detector (DRI), an online light scattering detector, and a viscometer. Experimental details not described below, including how the detectors were calibrated, are described in: T. Sun, P. Brant, R. R. Chance, and W. W. Graessley, Macromolecules, Vol. 34, No. 19, pp. 6812-6820, (2001).

Three Polymer Laboratories PLgel 10 mm Mixed-B columns were used. The nominal flow rate was 0.5 cm$^3$/min, and the nominal injection volume was 300 microliters. The various transfer lines, columns and differential refractometer (the DRI detector) were contained in an oven maintained at 135° C.

Solvent for the SEC experiment was prepared by dissolving 6 grams of butylated hydroxy toluene as an antioxidant in 4 liters of Aldrich reagent grade 1,2,4 trichlorobenzene (TCB). The TCB mixture was then filtered through a 0.7 μm glass pre-filter and subsequently through a 0.1 μm Teflon filter. The TCB was then degassed with an online degasser before entering the SEC.

Polymer solutions were prepared by placing dry polymer in a glass container, adding the desired amount of TCB, then heating the mixture at 160° C. with continuous agitation for about 2 hours. All quantities were measured gravimetrically. The TCB densities used to express the polymer concentration in mass/volume units are 1.463 g/ml at room temperature and 1.324 g/ml at 135° C. The injection concentration ranged from 1.0 to 2.0 mg/ml, with lower concentrations being used for higher molecular weight samples.

Prior to running each sample, the DRI detector and the injector were purged. Flow rate in the apparatus was then increased to 0.5 ml/minute, and the DRI was allowed to stabilize for 8-9 hours before injecting the first sample. The LS laser was turned on 1 to 1.5 hours before running samples by running the laser in idle mode for 20-30 minutes and then switching to full power in light regulation mode.

The concentration, c, at each point in the chromatogram is calculated from the baseline-subtracted DRI signal, $I_{DRI}$, using the following equation:

$$c = K_{DRI} I_{DRI}/(dn/dc)$$

where $K_{DRI}$ is a constant determined by calibrating the DRI, and (dn/dc) is the same as described below for the LS analysis. Units on parameters throughout this description of the SEC method are such that concentration is expressed in g/cm$^3$, molecular weight is expressed in g/mole, and intrinsic viscosity is expressed in dL/g.

The light scattering detector used is either a Wyatt Technology High Temperature mini-DAWN or a Precision Detector 2040 LALLS. The data is analyzed with the standard formulas for static light scattering $$\frac{K_o c}{\Delta R(\theta, c)} = \frac{1}{MP(\theta)} + 2A_2 c$$

Here, $\Delta R(\theta,c)$ is the excess Rayleigh scattering intensity at scattering angle θ, c is the polymer concentration, M is the polymer molecular weight, $A_2$ is the second virial coefficient of the solution, P(θ) is the form factor, and $K_o$ is the optical constant for the system:

$$K_o = \frac{4\pi^2 n^2 (dn/dc)^2}{\lambda^4 N_A} \quad (3)$$

in which $N_A$ is Avogadro's number, and dn/dc is the refractive index increment for the system. For the LALLS detector we measure the scattering intensity at 15° and assume $P(\theta)=1$. The concentrations used in the analyses are the values obtained from the DRI output. The refractive index n for TCB at 135° C. for a 690 nm wavelength is 1.500. In addition, $A_2=0.0006$ for propylene polymers and 0.0015 for butene polymers, and (dn/dc)=0.104 for propylene polymers and 0.098 for butene polymers.

The viscometer used was a Viscotek Corporation high temperature viscometer which has four capillaries arranged in a Wheatstone bridge configuration with two pressure transducers. One transducer measures the total pressure drop across the detector, and the other, positioned between the two sides of the bridge, measures a differential pressure. The specific viscosity, $\eta_s$, for the solution flowing through the viscometer is calculated from their outputs. The intrinsic viscosity, $[\eta]$, at each point in the chromatogram is calculated from the following equation:

$$\eta_s = c[\eta] + 0.3(c[\eta])^2$$

where c was determined from the DRI output.

The branching index (g') is calculated using the output of the SEC-DRI-LS-VIS method as follows. The average intrinsic viscosity, $[\eta]_{avg}$, of the sample is calculated by:

$$[\eta]_{avg} = \frac{\sum c_i [\eta]_i}{\sum c_i} \quad I = 1 \text{ to } n$$

where the summations are over the chromatographic slices, i, between the integration limits. The branching index g' is defined as:

$$g' = \frac{[\eta]_{avg}}{kM_v^\alpha}$$

where k=0.0002288 and α=0.705 for propylene polymers, and k=0.00018 and α=0.7 for butene polymers. $M_v$ is the viscosity-average molecular weight based on molecular weights determined by LS analysis.

Differential Scanning Calorimetry

Melting point ($T_m$), heat of fusion ($\Delta H_f$), multiple melting peak, and any measurements related to detection of crystalline melting or crystallization are measured by Differential Scanning Calorimetry (DSC). A typical procedure used was as follows—Preferably, about 5 mg to about 9 mg of polymer that has aged at room temperature for at least 24 hours, is placed in a Differential Scanning Calorimeter. The sample is heated at about 10° C./minute to attain a final temperature of about 200° C. Subsequently, the sample is cooled to room temperature at about 10° C./min, during which the thermal output records the heat of crystallization. The crystallization temperature ($T_{cmax}$) is recorded as the temperature at the peak of the crystallization exotherm. The sample is then heated back to 200° C. The thermal output is recorded as the area under the melting peak, or peaks, of the sample which is typically at a maximum peak at about 160° C. The melting point is recorded as the temperature of the greatest heat absorption within the range of melting of the sample. In some cases, following the heating cycle the sample was cooled below room temperature prior to the second heating cycle. The glass transition temperature ($T_g$) is taken at the midpoint of the glass transition observed during the heating cycle.

NMR Analyses $^{13}$C NMR was collected at 125° C. on a Varian NMR spectrometer. Sample concentrations were approximately 10 wt. % (wt/vol) in perdeutero tetrachloroethane. 10-mm NMR tubes contained these samples. Acquisition conditions were a 90-degree pulse, ungated broadband decoupling, approximately 15 seconds between successive data acquisitions, a sweep width of 8000 Hz, digital resolution 0f<0.2 Hz with the final spectrum composed of at least 1000 time-averaged data acquisitions.

$^1$H NMR was collected at 125° C. on Varian NMR spectrometers. Sample concentrations were approximately 1.5 wt. % (wt/vol) in perdeutero tetrachloroethane. 5-mm NMR tubes contained these samples. Acquisition conditions were <45-degree pulse, approximately 8 seconds between successive data acquisitions, and a sweep width of at least 10 ppm with the final spectrum composed of at least 120 time-averaged data acquisitions.

Melt Viscosity Measurements

Melt Flow Rate (MFR) was measured according to ASTM D1238 at 230° C. under a load of 2.16 kg. Melt Index (MI) was measured according to ASTM D 1238 at 190° C. under a load of 2.16 kg. The units are g/10 min, or dg/min.

Dynamic Mechanical Thermal Analysis

The storage modulus (E') and loss modulus (E") were measured using dynamic mechanical thermal analysis (DMTA). This test provides information about the small-strain mechanical response (relaxation behavior) of a sample as a function of temperature over a temperature range that includes the glass transition region and the visco-elastic region prior to melting.

Typically, samples are tested using a three point bending configuration (TA Instruments DMA 2980). A solid rectangular compression molded bar is placed on two fixed supports; a movable clamp applied a periodic deformation to the sample midpoint at a frequency of 1 Hz and an amplitude of 20 μm. The sample is initially cooled to −130° C. then heated to 60° C. at a heating rate of 3° C./min. In some cases, compression molded bars are tested using other deformation configurations, namely dual cantilever bending and tensile elongation (Rheometrics RSAII). The periodic deformation under these configurations is applied at a frequency of 1 Hz and strain amplitude of 0.05%. The sample is cooled to −130° C. and then heated to 60° C. at a rate of 2° C./min. The slight difference in heating rate does not influence the glass transition temperature measurements significantly.

The output of these DMTA experiments is the storage modulus (E') and loss modulus (E"). The storage modulus measures the elastic response or the ability of the material to store energy, and the loss modulus measures the viscous response or the ability of the material to dissipate energy. Tanδ is the ratio of E"/E' and gives a measure of the damping ability of the material. The beginning of the broad glass transition (β-relaxation) is identified as the extrapolated tangent to the Tanδ peak. In addition, the peak temperature and area under the peak were also measured to more fully characterize the transition from glassy to visco-elastic region.

Haze was determined by ASTM D1003, on a 0.04 inch think injection-molded plaque.

Microstructure, specifically mole % defects, % rr triads, $m^4$, mmmr, mmrr, rmmr, mmrm, mrrr, mrrm, rmrm, r4, m,r, 2,1 erythro, and 1,3 regio were determined by $^1H$ and $^{13}C$ NMR analysis protocols for polymer products as follows:

Proton NMR

The proton spectra were typically acquired with the 5 mm switchable probe, on the Varian UnityPlus 500. The samples were prepared in 1,2-dichlorobenzene-$d_4$ (to allow accurate integration of the olefin peaks) and dissolved at 120-140° C. A free induction decay of 400 coadded transients was acquired for each proton spectrum, at a temperature of 120° C. The proton spectra showed low levels of olefin, which are expressed below in terms of mole-fraction of total olefin content, as well as olefins per 1000 carbons for each type. At the molecular weights of these materials, the olefin concentration is very low, making it difficult to get accurate olefin distributions. The number of decimal places given in the results is not indicative of our confidence in the accuracy of the numbers, but rather are given to differentiate one low value from another. Vinyl endgroups contribute one proton's signal to the 5.6-5.9 ppm region, and 2 protons to the 4.9-5.3 ppm region. Non-cyclic 1,2-disubstituted olefins resonate in the 5.3-5.5 ppm region, with two proton's intensity. Signals from the single protons of trisubstituted olefins overlap the vinyl contributions in the 4.9-5.3 ppm region, and are measured by subtracting twice the downfield olefin concentration from this subintegral. Vinylidene olefins (two protons) are measured from the 4.6-4.9 ppm region integral. The olefin distribution can be determined by correcting each region's integral by the proton multiplicity of the contributing olefins. Assuming one olefin per polymer chain, we also estimated the number average molecular weight from the aliphatic/olefinic integral ratio. A sample proton olefin/molecular weight analysis is tabulated below:

| Olefin distribution (mole %) Olefins per 1000 carbons | | | | NMR-determined |
|---|---|---|---|---|
| vinyl | 1,2-disub. | trisub. | vinylidene | $M_n$ (g/mol) |
| 15.9% | 19.3% | 13.8% | 51.0% | 25027 |
| .09 | .11 | .08 | .29 | |

Carbon NMR

Carbon NMR spectra are usually acquired with the 10 mm broadband probe on the Varian UnityPlus 500. The samples are prepared in 1,1,2,2-tetrachloroethane-$d_2$, with relaxation agent—Cr(acac)$_3$—added to accelerate data acquisition. Sample preparation is performed at 120-140° C. Free induction decays of 16000 coadded transients were acquired at a temperature of 120° C. The tacticity was estimated by comparing the distribution of integral intensities (assigned to the range of pentad stereosequences) in the methyl region with those from literature references. (A. Tonelli and F. Schilling, *Acc. Chem. Res.* 14, 233 (1981).) The chain defects were assigned according to the work of Resconi et al. [L. Resconi, L. Cavallo, A. Fait, and F. Piemontesi, "Selectivity in Propene Polymerization with Metallocene Catalysts", *Chem. Rev.*, Vol. 100, pp. 1253-1345 (2000)] Consolidating the pentads into triads improves the reliability of the measurement. A sample result is tabulated below:

| | Tacticity (triad distribution, mole fraction) | | |
|---|---|---|---|
| Example | mm | mr | rr |
| 5 | .96 | .03 | .01 |

A sample of experimental pentad distribution and a least-squares Beroullian model fit are tabulated below:

| | Pentad concentrations (mole fraction) | | | | | | | | |
|---|---|---|---|---|---|---|---|---|---|
| Ex | mmmm | mmmr | rmmr | mmrr | mmrm+ | rmrm | rrrr | mrrr | mrrm |
| 5 | .921 | .021 | .019 | .017 | .003 | .005 | .001 | .001 | .012 |

In almost all spectra, two sets of defect peaks were observed, and these were assigned to erythro 2,1 inversion and 1,3 chain insertion. Their concentration is expressed in "defects per 10,000 monomers", which is analogous to mole-percent concentration (obtained by dividing the numbers below by 100). An example of the defect concentrations is tabulated below, along with the number of stereo defects (m/r switch). The average meso run length is also calculated from the pentad distribution.

| | | Defect concentrations (per 10,000 monomers) | | | | |
|---|---|---|---|---|---|---|
| Ex | Ave. meso run length | Stereo defects | 2,1 erythro | 2,1 threo | 1,3 insertion | Total defects |
| 5 | 44 | 122 | 93 | — | 13 | 227 |

Polymerization Procedure:

All polymerization experiments were performed in a continuous stirred autoclave (Autoclave Engineers, Erie Pa.) designed for a maximum pressure of 30,000 psi (2000 bar) and a maximum temperature of 225° C. The nominal reactor volume was 150 ml with working volume of 127 ml (working volume lower due to reactor internals). The reactor was equipped with a stirrer with a magnetic drive and an electric heater. A pressure transducer located on the monomer feed line measured the pressure in the reactor. The temperature was measured inside the reactor using a type-K thermocouple. The reactor was protected against over pressurization by automatically opening an air-actuated valve (High Pressure Company, Erie, Pa.) in case the reactor pressure exceeded a preset limit. A flush-mounted rupture disk located on the side of the reactor provided further protection against catastrophic pressure failure. All product lines from the reactor were heated to approximately 150° C. The reactor body had two heating bands that were controlled by a programmable logic control (PLC). Once the reactor lined out during polymerization, the reactor temperature was controlled manually by adjusting the flow rates of the monomer and catalyst feeds. Since the reaction was highly exothermic, no external heating was necessary in most experiments, i.e., the reactor temperature was maintained by controlling the heat release of polymerization.

Two lock-hopper assemblies were used to manage the flow of the effluent from the reactor to the collection vessels. The lock-hopper consisted of two air-actuated valves bracketing a short piece of high-pressure tubing. The volume of the lock-hopper was adjusted by changing the diameter and/or the length of the tube. One lock-hopper cycle consisted of first opening and closing of the valve between the lock-hopper tube and the reactor followed by opening and closing the downstream valve. The frequency of the lock-hopper cycles determined the effluent flow rate. For a given feed rate, the reactor pressure was controlled by adjusting the effluent flow rate through the lock-hopper. There were two independent lock-hoppers installed: one for waste collection during start up and shut down, and the other one for product collection during the balance periods at lined out, steady state conditions. A drain port on the bottom of the reactor was used to empty the reactor after each experiment.

Condensable monomers or monomer blends, such as propylene, butenes, or their blends with ethylene, were received in low-pressure cylinders equipped with a dip leg for liquid delivery to the reactor. Custom blends were also prepared in house. In both cases, a self-limiting heating blanket (max. temperature 80° F./26.7° C.) provided heat to increase the cylinder head pressure to deliver the monomer to the feed pump at a pressure above the bubble point. The low-pressure monomer feed was also stabilized against bubble formation by cooling the pump head using chilled water running at 10° C. The monomer feed was purified using two separate beds in series: activated copper (reduced in flowing $H_2$ at 225° C. and 1 bar) for $O_2$ removal and molecular sieve (5A, activated in flowing $N_2$ at 270° C.) for water removal. The purified monomer feed was fed by a diaphragm pump (Model MhS 600/11, ProMinent Orlita, Germany) through the axis of the stirrer into the reactor. The monomer flow rate was measured by a Coriolis mass flow meter (Model PROline Promass 80, Endress and Hauser) that was located downstream of the purification traps on the low-pressure side of the feed pump. A pulsation dampener (BALCOH, ~200 ml, maximum pressure 1000 psi/69 bar) was installed between the flow meter and the pump to dampen any oscillation in the flow caused by the membrane pump and to mitigate bubble formation. The same feed system could also deliver liquid monomers, such as hexene-1 or octene-1. The liquid monomer feed, however, was tied in to the monomer feed line downstream of the purifier traps, thus was used as received. The liquid monomer inventory was followed by a differential pressure gauge measuring the hydrostatic pressure of the monomer in the feed vessel.

The catalyst feed solution was prepared inside a $N_2$-filled dry box (Vacuum Atmospheres). The atmosphere in the glove box was purified to maintain <1 ppm $O_2$ and <1 ppm water. All glassware was oven-dried for a minimum of 4 hours at 120° C. and transferred hot to the antechamber of the dry box. Stock solutions of the catalyst precursors and the activators were prepared using purified toluene and stored in amber bottles inside the dry box. Aliquots were taken to prepare fresh activated catalyst solutions before each polymerization experiment.

The activated catalyst solutions were transferred to an oven-dried glass pressure equilibration vessel (drop-in funnel) equipped with a stopcock adapter with a hose connection. This solution was transferred under $N_2$ blanket into the catalyst feed reservoir. After the transfer from the glass drop-in funnel, a 50 psi (3.4 bar) head pressure of $N_2$ was applied to the catalyst feed vessel to maintain inert environment and to provide adequate suction pressure at the pump head. The catalyst solution inventory was followed by a differential pressure gauge measuring the hydrostatic pressure of the catalyst solution in the feed vessel. The activated catalyst solution was fed by a diaphragm pump (Model MhR 150/6, ProMinent Orlita, Germany) to a port on the side of the reactor. The flow rate of the catalyst solution was determined by the rate at which the catalyst solution was used from the feed vessel.

Toluene solvent was used to purge the feed lines and the reactor. The solvent feed was tied in via three-way valves to both the catalyst and the liquid monomer feed lines. The toluene solvent was distilled and stored under nitrogen in a feed vessel that was kept under 50 psi (3.4 bar) head pressure of $N_2$. This feed vessel was also equipped with a differential pressure gauge to monitor the toluene inventory.

In a typical experiment, the reactor was preheated to approximately 10-15° C. below that of the desired reaction temperature. Once the reactor reached the desired preheat temperature, the catalyst pump was turned on to deliver toluene to the reactor from the solvent vessel. After the flow of toluene to the reactor was verified by monitoring the amount of toluene taken from the solvent vessel, the monomer pump was turned on. The reactor was purged when the pressure increased to ~5000 psi (~345 bar) by opening each valve briefly. This reduced the pressure in the reactor and verified that all ports in the reactor were operational. After all valves had been tested and the reactor reached the desired reaction pressure, a three-way valve on the catalyst feed line was actuated to start the catalyst solution flow to the reactor. The arrival of the catalyst to the reactor was indicated by an increase in the reaction temperature caused by the exothermic polymerization reaction. During the line-out period, the catalyst feed and lock-hopper rates were adjusted to reach and maintain the target reaction temperature and pressure. Once the reactor reached steady state at the desired conditions, product collection was switched over from the waste collection to the on-balance product collection vessel. The reactor was typically run on-balance between 30 to 90 min, after which the effluent was redirected to the waste collection vessel and the reactor was shut down. The products were collected from the on-balance vessel. The conversion and reaction rates were determined based on the total feed used and the product yield during the balance period. The products were vacuum-dried overnight at 70° C. before characterization.

Materials

Propylene Grade 2.5 (BOC) was obtained in 100# low-pressure cylinders. Properties are listed in Table 1.

TABLE 1

Propylene properties

| | |
|---|---|
| Propylene | $C_3H_8$ |
| Molecular Weight | 42.078 g/mol |
| Density (@ 25° C., 1 bar) | 1.7229 kg/m$^3$ |
| Density (@ 125° C., 800 bar) | 544.9 kg/m$^3$ |
| Critical Temperature | 91.85° C. |
| Critical Pressure | 679 psi (46.2 bar) |
| Purity | 99.95% |

Activator and scavengers used were Methylaluminoxane (Albermarle Corporation) and Tri-isobutylaluminum (Sigma-Aldrich). Properties listed in Table 2.

TABLE 2

Properties of methylaluminumoxane and tri-isobutylaluminum

| | |
|---|---|
| Methylaluminoxane | $CH_3AlO$ |
| Abbreviation | MAO |
| Solution | 10 wt. % in toluene |
| Molecular Weight | 58.01 g/mol |
| Density (@ 23° C.) | 0.89 g/ml |
| Tri-isobutylaluminum | $(i-C_4H_9)_3Al$ |
| Abbreviation | TIBAL |
| Molecular Weight | 198.33 g/mol |
| Aluminum | 13.0-13.4 wt. % |
| Density (@ 20° C.) | 0.789 g/ml |

The solvent used in catalyst preparation and for reactor flushing was anhydrous toluene from Sigma-Aldrich (see Table 3).

TABLE 3

Toluene properties

| | |
|---|---|
| Toluene | $C_6H_5CH_3$ |
| Molecular Weight | 92.14 g/mol |
| Boiling point | 110.6° C. |
| Density (20° C.) | 0.865 g/ml |

The toluene was used as received (18 l, $N_2$ head pressure) for reactor rinsing and flushing. The toluene used in catalyst preparation (1-l sure-sealed bottles, Aldrich) was further purified: inside the $N_2$-filled dry box, a 2 l round bottom flask was filled with 1.5 l toluene about 500 mg sodium potassium alloy (NaK) was charged, stirred overnight, filtered through dried basic alumina. The alumina (Baker Chemical) was dried under vacuum overnight at 200° C.

Polymerization conditions for examples 1 through 16 are listed in Table A.

TABLE A

| Example | Polym. Temp. (° C.) | Pressure (kPa) | Residence Time (minute) | Catalyst Precursor |
|---|---|---|---|---|
| 1 | 121 | 207,000* | 6.5 | A |
| 2 | 113 | 210,000* | 6.6 | A |
| 3 | 111 | 205,000* | 6.2 | A |
| 4 | 137 | 203,000* | 7.0 | A |
| 5 | 122 | 203,464 | 6.0 | C |
| 6 | 135 | 206,243 | 5.2 | A |
| 7 | 109 | 203,333 | 5.3 | A |
| 8 | 135 | 206,277 | 5.8 | A |
| 9 | 121 | 206,167 | 5.8 | A |
| 10 | 148 | 203,499 | 5.4 | A |
| 11 | 175 | 206,022 | 6.4 | C |
| 12 | 111 | 201,597 | 5.2 | A |
| 13 | 113 | 202,597 | 5.4 | A |
| 14 | 112 | 199,887 | 5.4 | A |
| 15 | 114 | 199,687 | 5.4 | A |
| 16 | 113 | 198,694 | 5.5 | A |

Number rounded up.

Catalyst precursor A: dimethyl rac-dimethylsilyl-bis-(5,6,7,8-tetrahydro-5,5,8,8-tetramethyl-2-methyl-1H-benz(f)indene)hafnium dimethyl;

Catalyst precursor C: dimethylsilyl bis(2-methyl-4-phenyl-indenyl) zirconium dichloride;

Catalyst concentration: 110-610 mol ppb (parts per billion) in the feed to the reactor;

Activator in all runs: MAO; Al/metal (Zr or Hf) ratio: nominal 410:1.

Characterization data for the polymer products are listed in Tables B, C, D and E. Results in Table B, C, and D demonstrate the effect of temperature on product properties. They also show that products made with catalyst A have different properties than products made with catalyst B through a broad range of process conditions. Results in Table E show that the process of the present invention generates products reliably, with excellent reproducibility.

TABLE B

| | Example | | | |
|---|---|---|---|---|
| | 1 | 2 | 3 | 4 |
| Molecular weight (Mw - kg/mol) DRI | 233 | 248 | 225 | 116 |
| Melt Flow Rate (dg/min) | 7.1 | 4.8 | 8.5 | 100 |
| Melting Peak Temperature - 13 $T_m$ (° C.) | 148 | 145 | 125 | 123 |
| Heat of Fusion - $\Delta H_f$ (J/g) | 66 | 53 | 32 | 37 |
| Crystallization Peak Temperature - $T_{cmax}$ (° C.) | 104 | 98 | 82 | 83 |
| Glass Transition Temperature - $T_g$ (° C.) | -8 | -10 | -7 | -8 |
| Haze - (%) (tested on a 4-mil plaque) | | | 6 | 16 |
| DMTA E' (Pa at 23-25° C.) | | | 4.6E8 | |
| DMTA E'' (Pa at 23-25° C.) | | | 5.6E7 | |
| Microstructure (Normalized Population) | | | | |
| Defects (mol %) | 5.9% | 7.8% | 12.4% | 10.1% |
| % rr triads | 6% | 7% | 14% | 11% |
| mmmm | 0.733 | 0.669 | 0.402 | 0.550 |
| mmmr | 0.082 | 0.096 | 0.193 | 0.134 |
| mmrr | 0.072 | 0.100 | 0.148 | 0.129 |
| rmmr | 0.024 | 0.022 | 0.032 | 0.024 |
| mmrm | 0.018 | 0.023 | 0.057 | 0.035 |
| mrrr | 0.015 | 0.019 | 0.038 | 0.028 |
| mrrm | 0.035 | 0.043 | 0.075 | 0.064 |
| rmrm | 0.013 | 0.018 | 0.032 | 0.022 |
| rrrr | 0.008 | 0.010 | 0.023 | 0.014 |
| m derived from m pentads | 0.925 | 0.904 | 0.796 | 0.861 |
| r derived from r pentads | 0.299 | 0.316 | 0.389 | 0.344 |
| 2,1 erythro defects/10,000 $C_3^=$ | 80 | 71 | 62 | 65 |
| 1,3 regio defects/10,000 $C_3^=$ | 2 | 8 | 15 | 30 |

TABLE C

| | Example | | | | |
|---|---|---|---|---|---|
| | 5 | 6 | 7 | 8 | 9 |
| Molecular weight (Mw - kg/mol), DRI | 173 | 156 | 214 | 202 | 200 |
| Melt Flow Rate (dg/min) | 12.4 | 26.1 | | 29.2 | 11.5 |
| g' at $M_w$ | 0.98 | 1.03 | 1.04 | 1.06 | 1.03 |
| Melting Peak Temperature - $T_m$ (° C.) | 148 | 126 | 126 | 125 | 129 |
| Heat of Fusion - $\Delta H_f$ (J/g) | 56 | 42 | 29 | 30 | 46 |
| Crystallization Peak Temperature - $T_{cmax}$ (° C.) | 116 | 91 | 82 | 88 | 90 |
| Glass Transition Temperature - $T_g$ (° C.) | −10 | −9 | −7 | −9 | −8 |
| Microstructure (Normalized Population) | | | | | |
| Defects (mol %) | 2.3% | 10.1% | 12.3% | 10.5% | 8.7% |
| % rr triads | 1% | 11% | 15% | 11% | 9% |
| mmmm | 0.921 | 0.540 | 0.446 | 0.534 | 0.631 |
| mmmr | 0.021 | 0.128 | 0.128 | 0.134 | 0.114 |
| mmrr | 0.017 | 0.121 | 0.127 | 0.127 | 0.111 |
| rmmr | 0.019 | 0.033 | 0.045 | 0.023 | 0.025 |
| mmrm | 0.003 | 0.043 | 0.077 | 0.042 | 0.032 |
| mrrr | 0.001 | 0.025 | 0.061 | 0.033 | 0.020 |
| mrrm | 0.012 | 0.069 | 0.062 | 0.065 | 0.054 |
| rmrm | 0.005 | 0.025 | 0.031 | 0.026 | 0.018 |
| rrrr | 0.001 | 0.016 | 0.022 | 0.015 | 0.013 |
| m not derived from m pentads | 0.974 | 0.796 | 0.737 | 0.789 | 0.833 |
| r not derived from r pentads | 0.026 | 0.204 | 0.263 | 0.211 | 0.167 |
| 2,1 erythro defects/10,000 $C_3^=$ | 93 | 64 | 54 | 68 | 71 |
| 1,3 regio defects/10,000 $C_3^=$ | 13 | 26 | 9 | 25 | 12 |

TABLE D

| | Example | |
|---|---|---|
| | 10 | 11 |
| Molecular weight (Mw - kg/mol) DRI | 100 | 35 |
| Melt Flow Rate (dg/min) | 133 | 10440 |
| g' at $M_w$ | 0.99 | 0.97 |
| Melting Peak Temperature - $T_m$ (° C.) | 148 | 143.3 |
| Heat of Fusion - $\Delta H_f$ (J/g) | 72 | 97 |
| Crystallization Peak Temperature - $T_{cmax}$ (° C.) | 110 | 109 |
| Glass Transition Temperature - $T_g$ (° C.) | −7 | −10 |
| Haze - (%) (tested on a 4-mil plaque) | | |
| Microstructure (Normalized Population) | | |
| Defects (mol %) | 8.7% | 4.7% |
| % rr triads | 9% | 3% |
| mmmm | 0.602 | 0.804 |
| mmmr | 0.128 | 0.076 |
| mmrr | 0.108 | 0.037 |
| rmmr | 0.023 | 0.015 |
| mmrm | 0.031 | 0.018 |
| mrrr | 0.020 | 0.009 |
| mrrm | 0.057 | 0.022 |
| rmrm | 0.020 | 0.015 |
| rrrr | 0.011 | 0.004 |
| m not derived from m pentads | 0.833 | 0.930 |
| r not derived from r pentads | 0.167 | 0.070 |
| 2,1 erythro defects/10,000 $C_3^=$ | 61 | 83 |
| 1,3 regio defects/10,000 $C_3^=$ | 27 | 45 |

TABLE E

| | Example | | | | |
|---|---|---|---|---|---|
| | 12 | 13 | 14 | 15 | 16 |
| Molecular weight (Mw - kg/mol) DRI | 276 | 238 | 266 | 247 | 242 |
| Melt Flow Rate (dg/min) | 4.8 | 8.0 | 6.5 | 7.0 | 5.8 |
| $M_w/M_n$ | 1.96 | 1.91 | 1.92 | 1.81 | 1.91 |
| Melting Peak Temperature - $T_m$ (° C.) | 129 | 128 | 128 | 128 | 128 |
| Heat of Fusion - $\Delta H_f$ (J/g) | 54 | 48 | 48 | 55 | 53 |
| Crystallization Peak Temperature - $T_{cmax}$ (° C.) | 93 | 91 | 92 | 92 | 92 |
| Microstructure (Normalized Population) | | | | | |
| Defects (mol %) | 7.0% | 7.7% | 8.3% | 7.6% | 8.2% |
| % rr triads | 8% | 7% | 8% | 8% | 8% |
| mmmm | 0.666 | 0.654 | 0.632 | 0.670 | 0.612 |
| mmmr | 0.104 | 0.111 | 0.113 | 0.097 | 0.130 |
| mmrr | 0.094 | 0.104 | 0.110 | 0.106 | 0.106 |
| rmmr | 0.025 | 0.022 | 0.025 | 0.017 | 0.028 |
| mmrm | 0.019 | 0.020 | 0.027 | 0.022 | 0.027 |
| mrrr | 0.006 | 0.004 | 0.008 | 0.017 | 0.018 |

TABLE E-continued

|  | Example | | | | |
|---|---|---|---|---|---|
|  | 12 | 13 | 14 | 15 | 16 |
| mrrm | 0.063 | 0.060 | 0.063 | 0.050 | 0.056 |
| rmrm | 0.013 | 0.014 | 0.014 | 0.011 | 0.014 |
| rrrr | 0.010 | 0.009 | 0.009 | 0.009 | 0.009 |
| m derived from m pentads | 0.903 | 0.899 | 0.892 | 0.905 | 0.884 |
| r derived from r pentads | 0.316 | 0.308 | 0.308 | 0.308 | 0.308 |
| 2,1 erythro defects/10,000 $C_3^-$ | 69 | 74 | 78 | 63 | 83 |
| 1,3 regio defects/10,000 $C_3^-$ | 12 | 12 | 14 | 12 | 22 |

Blends

Two of the above polymers were blended with a polyalphaolefin to prepare a plasticized polymer composition. Details are presented in Table F

TABLE F

|  | Example | | | |
|---|---|---|---|---|
|  | 1 | 2 | 3 | 4 |
| Ex. 4 Polymer | 8.5 g |  | 8.0 g |  |
| Ex. 3 Polymer |  | 8.0 g |  | 9.0 g |
| SHF-101 | 1.5 g | 2.0 g | 2.0 g | 1.0 g |

SHF 101 is a polyalphaolefin oligomer formerly available from ExxonMobil Chemical Company having a Viscosity Index of 136, a KV100 of 10 cSt, a pour point of −54° C. and a specific gravity of 0.835 (15.6/15.6° C.). A similar polyalphaolefin is now available under the trade name Spectrasyn™ 10 from ExxonMobil Chemical Company in Houston, Tex.

While certain representative embodiments and details have been shown to illustrate the invention, it will be apparent to skilled artisans that various process and product changes from those disclosed in this application may be made without departing from this invention's scope, which the appended claims define. All cited patents, test procedures, priority documents, and other cited documents are fully incorporated herein by reference to the extent that this material is consistent with this specification and for all jurisdictions in which such incorporation is permitted. Certain features of the present invention are described in terms of a set of numerical upper limits and a set of numerical lower limits. This specification discloses all ranges formed by any combination of these limits. All combinations of these limits are within the scope of the invention unless otherwise indicated. It should be appreciated that ranges from any lower limit to any upper limit are within the scope of the invention unless otherwise indicated.

What is claimed is:

1. A process to polymerize olefins comprising contacting, in a polymerization system, olefin monomers having three or more carbon atoms with:
1) a metallocene catalyst compound,
2) an activator,
3) optionally comonomer, and
4) optionally diluent or solvent,
at a temperature above the cloud point temperature of the polymerization system and a pressure no lower than 10 MPa below the cloud point pressure of the polymerization system and less than 1000 MPa,
where the polymerization system comprises the monomers, any comonomer present, any diluent or solvent present, and the polymer product, and
where the olefin monomers are present in the polymerization system at 40 weight % or more, wherein the metallocene catalyst compound is represented by the formula:

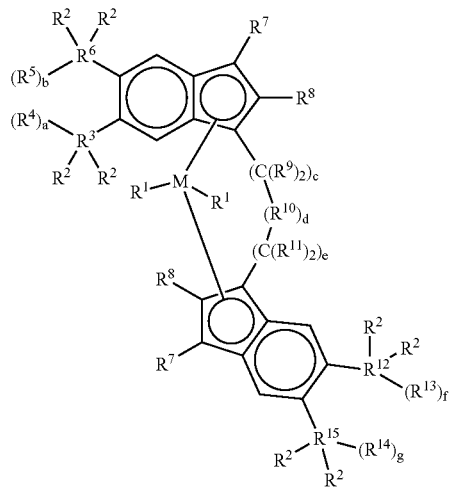

where

M is a transition metal selected from group 4 of the periodic table;

each $R^1$ is independently selected from the group consisting of hydrogen, hydrocarbyl, substituted hydrocarbyl and functional group, and any two $R^1$ groups may be linked, provided that if the two $R^1$ groups are linked, then they do not form a butadiene group when M is Zr;

each $R^2$ is independently selected from the group consisting of hydrogen, hydrocarbyl, substituted hydrocarbyl or a functional group, and two or more $R^2$ groups may be linked together to form an aliphatic or aromatic ring;

$R^3$ is carbon or silicon;

$R^4$ is hydrogen, hydrocarbyl, substituted hydrocarbyl or a functional group;

a is 0, 1 or 2;

$R^5$ is hydrogen, hydrocarbyl, substituted hydrocarbyl or a functional group, $R^4$ and $R^5$ may be bound together to form a ring, and $R^5$ and $R^3$ may be bound together to form a ring;

b is 0, 1 or 2;

$R^6$ is carbon or silicon; and $R^4$ and $R^6$ may be bound together to form a ring;

each $R^7$ is independently selected from the group consisting of hydrogen, hydrocarbyl, substituted hydrocarbyl and a functional group;

each $R^8$ is independently selected from the group consisting of hydrogen, hydrocarbyl, substituted hydrocarbyl and a functional group, and $R^7$ and $R^8$ may be linked together to form an aliphatic or aromatic ring;

each $R^9$ is independently selected from the group consisting of hydrogen, hydrocarbyl, substituted hydrocarbyl and a functional group, and two $R^9$ groups may be linked together to form a ring, $R^9$ and $R^8$ may be linked together to form a ring, $R^9$ and $R^{16}$ may be linked together to form a ring, $R^9$ and $R^{11}$ may be linked together to form a ring;

c is 0, 1 or 2;

$R^{10}$ is $-M^2(R^{16})_h$-where $M^2$ is B, Al, N, P, Si or Ge, h is an integer from 1 to 2, such that the valence of $M^2$ is filled, and $R^{16}$ is hydrogen, hydrocarbyl, substituted hydrocarbyl or a functional group, and two $R^{16}$ groups may be linked together to form a ring;

d is 0, 1, or 2;

each $R^{11}$ is independently selected from the group consisting of hydrogen, hydrocarbyl, substituted hydrocarbyl and a functional group, and two $R^{11}$ groups may be linked together to form a ring $R^{11}$ and $R^8$ may be linked together to form a ring $R^{11}$ and $R^{16}$ may be linked together to form a ring;

e is 0, 1, or 2;

where the sum of c, d, and e is 1, 2 or 3;

$R^{12}$ is carbon or silicon;

$R^{13}$ is hydrogen, hydrocarbyl, substituted hydrocarbyl or a functional group, and $R^{13}$ and $R^{14}$ may be bound together to form a ring, and $R^{13}$ and $R^{15}$ may be bound together to form a ring, when g is 0;

f is 0, 1 or 2;

$R^{14}$ is hydrogen, hydrocarbyl, substituted hydrocarbyl or a functional group, and $R^{14}$ and $R^{12}$ may be bound together to form a ring, when f is 0;

g is 0, 1 or 2; and $R^{15}$ is carbon or silicon.

2. The process of claim 1 wherein $R^3$ is carbon, and or $R^6$ is carbon, and or $R^{12}$ is carbon, and or $R^{15}$ is carbon.

3. The process of claim 1 wherein the process is a continuous process.

4. The process of claim 1 wherein $R^4$ and or $R^5$ is $CH_2$.

5. The process of claim 1 wherein $R^{13}$ is $CH_2$.

6. The process of claim 1 wherein $R^{14}$ is $CH_2$.

7. The process of claim 1 wherein the metallocene catalyst compound is represented by the formula:

where:

M, $R^1$, $R^2$ $R^7$, $R^8$, $R^9$, $R^{10}$, $R^{11}$, c, d, and e are as defined in claim 1.

8. The process of claim 1 wherein M is hafnium or zirconium.

9. The process of claim 7 wherein M is hafnium.

10. The process claim 1 wherein $R^1$ is hydride, amide, a hydrocarbyl, or a halide.

11. The process of claim 7 wherein $R^1$ is selected from the group consisting of methyl, ethyl, trimethylsilylmethyl, trimethylsilyl, phenyl, naphthyl, allyl, and benzyl.

12. The process of claim 1 wherein $R^2$ is methyl, ethyl or propyl.

13. The process of claim 1 wherein $R^7$ is hydrogen, methyl, ethyl or propyl.

14. The process of claim 1 wherein $R^8$ is hydrogen, methyl, ethyl or propyl.

15. The process of claim 1 wherein $R^9$ is hydrogen, methyl, ethyl, propyl or phenyl.

16. The process of claim 1 wherein $R^{10}$ is $SiMe_2$, $Si(CH_2)_3$, $SiPh_2$, $Si(biphenyl)_2$, $Si(o-tolyl)_2$.

17. The process of claim 1 wherein $R^{11}$ is hydrogen, methyl, ethyl, propyl or phenyl.

18. The process of claim 1 wherein the sum of c, d, and e is 1 or 2.

19. The process of claim 1 where the sum of c, d, and e is 1.

20. The process of claim 19 wherein:

M is hafnium, $R^1$ is selected from the group consisting of methyl, ethyl, trimethylsilylmethyl, trimethylsilyl, phenyl, naphthyl, allyl, and benzyl, $R^2$ is methyl, ethyl or propyl, $R^7$ is hydrogen, methyl, ethyl or propyl, $R^8$ is hydrogen, methyl, ethyl or propyl, $R^9$ is hydrogen, methyl, ethyl, propyl or phenyl, $R^{10}$ is $SiMe_2$, $Si(CH_2)_3$, $SiPh_2$, $Si(biphenyl)_2$, $Si(o-tolyl)_2$; and $R^{11}$ is hydrogen, methyl, ethyl, propyl or phenyl.

21. The process of claim 1 wherein the metallocene catalyst compound is represented by the formula:

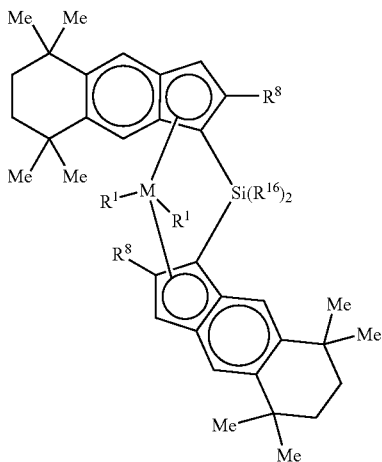

where:
M, $R^1$, $R^8$, and $R^{16}$ are as defined in claim 1, and Me is methyl.

22. The process of claim 21 wherein M is hafnium, $R^1$ is a hydride, methyl, ethyl, trimethylsilylmethyl, trimethylsilyl, phenyl, naphthyl, allyl, or benzyl, $R^8$ is hydrogen, methyl, ethyl or propyl; and $R^{16}$ is methyl, ethyl, phenyl, biphenyl, o-tolyl, or an arene.

23. The process of claim 1 wherein $R^8$ is not a phenyl group.

24. The process of claim 1 wherein the metallocene catalyst compound is represented by the one of the following formulae:

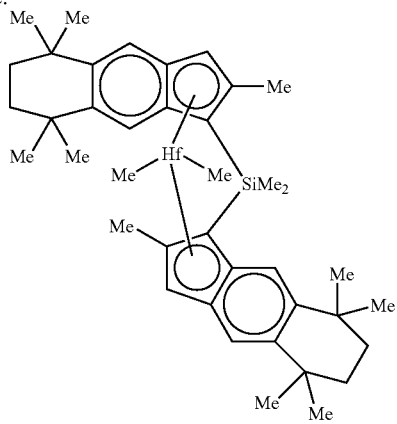

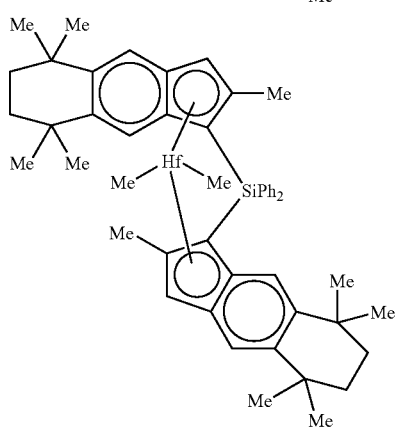

-continued

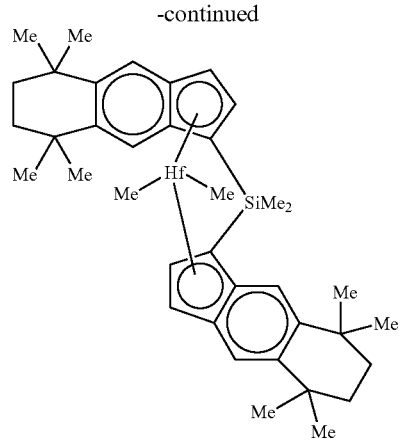

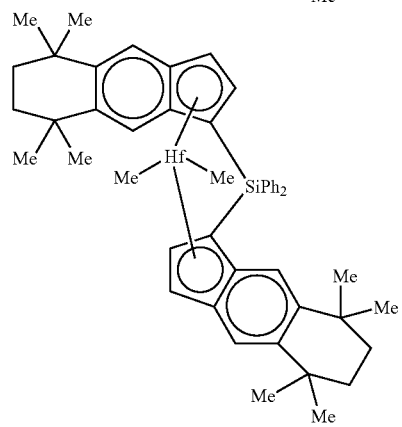

where Me is methyl, Hf is hafnium, Ph is phenyl, and Si is silicon.

25. The process of claim 1 wherein the activator is a Lewis acid that ionizes the bridged metallocene metal center into a cation and provides a counterbalancing noncoordinating ion.

26. The process of claim 1 wherein the activator is represented by the following formula:

$S^{t+}$ is a cation component having the charge t+
$NCA^{v-}$ is a non-coordinating anion having the charge v−
t is an integer from 1 to 3;
v is an integer from 1 to 3;
u and v are constrained by the relationship: (u)×(t)=(v)× (w); where $S^{t+}$ is a Bronsted acid or a reducible Lewis acid capable of protonating or abstracting a moiety.

27. The process of claim 7 wherein the activator is selected from the group consisting of trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl) borate, N,N-dimethylanilinium tetrakis(pentafluorophenyl) borate, N,N-diethylanilinium tetrakis (pentafluorophenyl) borate, N,N-dimethyl-(2,4,6-trimethylanilinium) tetrakis(pentafluorophenyl) borate, trimethylammonium tetrakis(heptafluoronaphthyl)borate, triethylammonium tetrakis(heptafluoronaphthyl)borate, tripropylammonium tetrakis(heptafluoronaphthyl)borate, tri (n-butyl)ammonium tetrakis(heptafluoronaphthyl)borate, tri (sec-butyl)ammonium tetrakis(heptafluoronaphthyl)borate, N,N-dimethylanilinium tetrakis(heptafluoronaphthyl)borate, N,N-diethylanilinium tetrakis(heptafluoronaphthyl)borate, trimethylammonium (2-perfluorobiphenyl)$_3$(perfluorophenylalkynyl)borate, triethylammonium (2-perfluorobiphenyl)$_3$(perfluorophenylalkynyl)borate, tripropylammonium (2-perfluorobiphenyl)$_3$(perfluorophenylalkynyl)borate, tri(n-butyl)ammonium (2-perfluorobiphenyl)$_3$(perfluorophenylalkynyl)borate, tri(sec-butyl)ammonium (2-perfluorobiphenyl)$_3$(perfluorophenylalkynyl) borate, N,N-dimethylanilinium (2-perfluorobiphenyl)$_3$ (perfluorophenylalkynyl)borate, N,N-diethylanilinium (2-perfluorobiphenyl)$_3$(perfluorophenylalkynyl)borate, trimethylammonium tetrakis-(2,3,4,6-tetrafluorophenylborate, triethylammonium tetrakis-(2,3,4,6-tetrafluorophenyl) borate, tripropylammonium tetrakis-(2,3,4,6-tetrafluorophenyl) borate, tri(n-butyl)ammonium tetrakis-(2,3,4,6-tetrafluoro-phenyl) borate, dimethyl(t-butyl)ammonium tetrakis-(2,3,4,6-tetrafluorophenyl) borate, N,N-dimethylanilinium tetrakis-(2,3,4,6-tetrafluorophenyl) borate, N,N-diethylanilinium tetrakis-(2,3,4,6-tetrafluorophenyl) borate, N,N-dimethyl-(2,4,6-trimethylanilinium)tetrakis-(2,3,4,6-tetrafluorophenyl) borate, di-(i-propyl)ammonium tetrakis(pentafluorophenyl) borate, and dicyclohexylammonium tetrakis(pentafluorophenyl) borate, triphenylphosphonium tetrakis(pentafluorophenyl) borate, tri(o-tolyl)phosphonium tetrakis(pentafluorophenyl) borate, and tri(2,6-dimethylphenyl)phosphonium tetrakis(pentafluorophenyl) borate, triphenylcarbenium tetrakis(pentafluorophenyl)borate, triphenylcarbenium tetrakis(heptafluoronaphthyl)borate, triphenylcarbenium (2-perfluorobiphenyl)$_3$(perfluorophenylalkynyl)borate, trisperfluorophenyl borane, and triperfluoronaphthyl borane.

28. The process of claim 1 wherein the activator is selected from the group consisting of N,N-dimethylanilinium tetrakis(perfluorophenyl)borate and triphenylcarbenium tetrakis(perfluorophenyl)borate.

29. The process of claim 1 wherein the activator comprises an alumoxane.

30. The process of claim 7 wherein the activator is a methylalumoxane.

31. The process of claim 1 wherein the activator is N, N-dimethylanilinium tetrakis(perfluorophenyl) borate.

32. The process of claim 1 further comprising a scavenger selected from the group consisting of trimethylaluminum, triethylaluminum, triisobutylaluminum, tri-n-hexylaluminum, and tri-n-octylaluminum.

33. The process of claim 1 wherein the catalyst, the activator or both are supported.

34. The process of claim 1 wherein the pressure of the polymerization system is above the cloud point pressure of the polymerization system.

35. The process of claim 1 wherein the pressure of the polymerization system is 27.5 MPa or more and the temperature is 100° C. or more.

36. The process of claim 7 wherein the pressure of the polymerization system is 27.5 MPa or more and the temperature is 105° C. or more.

37. The process of claim 1 wherein the pressure of the polymerization system is 28.5 MPa or more and the temperature is 110° C. or more.

38. The process of claim 1 wherein the pressure of the polymerization system is between 25 and 200 MPa.

39. The process of claim 1 wherein the temperature of the polymerization system is between 105 and 140° C.

40. The process of claim 1 wherein solvent and or diluent is present in the polymerization system at 0 to 25 wt %.

41. The process of claim 7 wherein solvent and or diluent is present in the polymerization system at 0 to 10 wt %.

42. The process of claim 1 wherein the olefin monomers having three or more carbon atoms are present in the polymerization system at 55 wt % or more.

43. The process of claim 1 wherein the olefin monomers having three or more carbon atoms are present in the polymerization system at 75 wt % or more.

44. The process of claim 1 wherein the olefin monomer having three or more carbon atoms comprises propylene.

45. The process of claim 1 wherein comonomer is present at 1 to 45 mole %.

46. The process of claim 1 wherein the polymerization medium of the monomer, comonomers, solvents and diluents comprises from 55-100 wt % propylene monomer; from 0 to 45 wt % of a comonomer mixture comprising at least one comonomer selected from ethylene, but-1-ene, hex-1-ene, 4-methylpent-1-ene, dicyclopentadiene, norbornene, $C_4$-$C_{2000}$ α-olefins, $C_4$-$C_{2000}$ α,internal-diolefins, and $C_4$-$C_{2000}$ α,ω-diolefins.

47. The process of claim 46 wherein the comonomer comprises one or more of ethylene, butene, hexene, or octene.

48. The process of claim 1 wherein the polymerization takes place in a tubular reactor.

49. The process of claim 48 wherein the tubular reactor has a length-to-diameter ratios of 1:1 to 20:1.

50. The process of claim 48 wherein the tubular reactor has a length-to-diameter ratio of 4:1 to 20:1.

51. The process of claim 48 wherein the tubular reactor has a length-to-diameter ratio of 1:1 to 500:1.

52. The process of claim 48 wherein the tubular reactor has a length of 100-2000 meters and an internal diameter of less than 10 cm.

53. The process of claim 48 wherein the tubular reactor contains up to six different injection positions.

54. The process of claim 48 wherein the tubular reactor is operated in multiple zones.

55. The process of claim 1 wherein the polymerization takes place in an autoclave reactor.

56. The process of claim 55 wherein the autoclave reactor has a length-to-diameter ratio of 1:1 to 20:1.

57. The process of claim 55 wherein the autoclave reactor has a length-to-diameter ratio of less than 4.

58. The process of claim 55 wherein the autoclave reactor contains up to six different injection positions.

59. The process of claim 55 wherein the autoclave reactor is operated in multiple zones.

60. The process of claim 1 wherein the process comprises (a) continuously feeding olefin monomers, metallocene catalyst compound, and activator to the reactor; (b) continuously polymerizing the monomers in a polymerization zone reactor under elevated pressure; (c) continuously removing the polymer/monomer mixture from the reactor; (d) continuously separating monomer from molten polymer; (e) reducing pressure to form a monomer-rich and a polymer-rich phase; and (f) separating monomer from the polymer.

61. The process of claim 1 wherein the polymerization takes place in a loop reactor.

62. The process of claim 61 wherein the loop reactor has a diameter of 41 to 61 cm and a length of 100 to 200 meters.

63. The process of claim 61 wherein the loop reactor is operated at pressures of 25 to 30 MPa.

64. The process of claim 61 wherein an in-line pump continuously circulates the polymerization system through the loop reactor.

65. The process of claim 61 wherein the process comprises (a) continuously feeding olefin monomers, catalyst compound, and activator to the loop reactor; (b) continuously polymerizing the monomers in a polymerization zone reactor under elevated pressure; (c) continuously removing the polymer/monomer mixture from the reactor; (d) continuously separating monomer from molten polymer; (e) reducing pressure to form a monomer-rich and a polymer-rich phase; and (f) separating monomer from the polymer.

66. The process of claim 1 wherein the polymerization system comprises multiple reactors.

67. The process of claim 66 wherein the polymerization system comprises a tubular reactor and autoclave reactor.

68. The process of claim 66 wherein the polymerization system comprises a tubular reactor and then a loop reactor.

69. The process of claim 1 wherein the residence time is less than 5 minutes.

* * * * *